US011854708B2

(12) United States Patent
Streat et al.

(10) Patent No.: US 11,854,708 B2
(45) Date of Patent: Dec. 26, 2023

(54) HEALTHCARE SERVICE PLATFORM

(71) Applicant: DexCare, Inc., Renton, WA (US)

(72) Inventors: Derek Alan Streat, Seattle, WA (US); William Bryant Larson, Seattle, WA (US); James Michael Heim, Lynwood, WA (US); Jeffrey Alan Herold, Kirkland, WA (US); Stephanie Michelle Deter, Seattle, WA (US); Chad Garrett Waldman, Kirkland, WA (US); Christopher Chase Carruthers, Issaquah, WA (US)

(73) Assignee: DexCare, Inc., Seattle, WA (US)

( * ) Notice: Subject to any disclaimer, the term of this patent is extended or adjusted under 35 U.S.C. 154(b) by 0 days.

(21) Appl. No.: 17/551,084

(22) Filed: Dec. 14, 2021

(65) Prior Publication Data
US 2023/0187086 A1 Jun. 15, 2023

(51) Int. Cl.
*G16H 80/00* (2018.01)
*G16H 40/20* (2018.01)

(52) U.S. Cl.
CPC ............. *G16H 80/00* (2018.01); *G16H 40/20* (2018.01)

(58) Field of Classification Search
CPC ............................... G16H 40/20; G16H 80/00
(Continued)

(56) References Cited

U.S. PATENT DOCUMENTS 8,145,726 B1 3/2012 Roche et al.
9,372,731 B1 6/2016 Marr et al.
(Continued)

FOREIGN PATENT DOCUMENTS

CN 113923441 A 1/2022
JP 2016-167676 A 9/2016
(Continued)

OTHER PUBLICATIONS

Tan, J. et al. (2002). From telemedicine to e-health: Uncovering new frontiers of biomedical research, clinical applications & public health services delivery. The Journal of Computer Information Systems, 42(5), 7-18. Retrieved from https://dialog.proquest.com/professional/docview/ (Year: 2002).*
(Continued)

*Primary Examiner* — Christopher L Gilligan
*Assistant Examiner* — Bennett Stephen Erickson
(74) *Attorney, Agent, or Firm* — John W. Branch; Branch Partners PLLC

(57) ABSTRACT

Embodiments are directed to managing the provisioning of healthcare services. A visit profile that includes a reason for the visit and patient demographic information may be provided by a patient requesting a visit to obtain healthcare services. Match scores for providers may be generated based on matching models and the visit profile. A provider may be assigned to the visit based on the match scores. A virtual waiting room may be provided for the patient based on the visit profile. The visit profile may be updated with supplemental information based on the interactions between the patient and the virtual waiting room, patient information, or visit information. Updated match scores may be provided for the providers based on the updated visit profile. If an updated match score exceeds a previously determined higher match score, another provider associated with a higher match score may be assigned to the visit.

30 Claims, 20 Drawing Sheets

(58) Field of Classification Search
USPC .......................................................... 705/2
See application file for complete search history.

(56) References Cited

U.S. PATENT DOCUMENTS

| | | | |
|---|---|---|---|
| 9,380,268 | B2 | 6/2016 | Weber et al. |
| 9,402,054 | B2 | 7/2016 | Aaron et al. |
| 9,497,412 | B1 | 11/2016 | Rosenberg |
| 2004/0185785 | A1 | 9/2004 | Mir et al. |
| 2006/0271400 | A1* | 11/2006 | Clements ............... G16H 10/60 600/301 |
| 2014/0180715 | A1* | 6/2014 | Phillips ................ G06Q 10/103 705/2 |
| 2014/0313282 | A1 | 10/2014 | Ma et al. |
| 2016/0308737 | A1 | 10/2016 | Liu et al. |
| 2017/0272485 | A1 | 9/2017 | Gordon et al. |
| 2019/0122760 | A1* | 4/2019 | Wang ..................... G16H 10/60 |
| 2019/0333613 | A1* | 10/2019 | Zaidi ...................... G16H 20/40 |
| 2020/0222813 | A1 | 7/2020 | Baszucki |
| 2020/0357494 | A1* | 11/2020 | Kadri ..................... G16H 40/20 |
| 2021/0076001 | A1 | 3/2021 | Periyannan et al. |
| 2021/0314526 | A1 | 10/2021 | Astarabadi et al. |
| 2021/0319914 | A1* | 10/2021 | Roh ....................... G16H 40/67 |
| 2021/0358618 | A1* | 11/2021 | Crocker ................. G16H 40/67 |
| 2021/0399911 | A1 | 12/2021 | Jorasch et al. |
| 2021/0400142 | A1 | 12/2021 | Jorasch et al. |
| 2021/0406841 | A1* | 12/2021 | Chen ...................... G16H 40/20 |
| 2022/0165401 | A1* | 5/2022 | Levitt .................... G16H 40/20 |
| 2022/0215970 | A1* | 7/2022 | Trpkovski .......... G07C 9/00182 |

FOREIGN PATENT DOCUMENTS

| | | |
|---|---|---|
| WO | 2014018012 A1 | 1/2014 |
| WO | 2016019227 A1 | 2/2016 |

OTHER PUBLICATIONS

Office Communication for U.S. Appl. No. 17/837,218 dated Mar. 9, 2023, pp. 1-7.
Office Communication for U.S. Appl. No. 17/837,218 dated Mar. 15, 2023, pp. 1-2.
Office Communication for U.S. Appl. No. 18/114,916 dated May 23, 2023, pp. 1-9.
Office Communication for U.S. Appl. No. 17/837,218 dated Nov. 17, 2022, pp. 1-20.
Office Communication for U.S. Appl. No. 17/692,738 dated Jan. 5, 2023, pp. 1-8.
Office Communication for U.S. Appl. No. 17/837,218 dated Feb. 9, 2023, pp. 1-5.
Office Communication for U.S. Appl. No. 17/692,738 dated Jun. 13, 2022, pp. 1-9.
Office Communication for U.S. Appl. No. 18/130,660 dated Jun. 14, 2023, pp. 1-16.
International Search Report and Written Opinion for International Patent Application No. PCT/US2023/013531 dated Jun. 6, 2023, pp. 1-7.
Office Communication for U.S. Appl. No. 17/837,218 dated Aug. 12, 2022, pp. 1-17.
Office Communication for U.S. Appl. No. 17/692,738 dated Oct. 4, 2022, pp. 1-10.

* cited by examiner

HEALTHCARE SERVICE PLATFORM

TECHNICAL FIELD

The present invention relates generally to managing healthcare services, and more particularly, but not exclusively, to coordinating patient and provider allocations.

BACKGROUND

Providing healthcare services often require complex relationships between disparate stakeholders, including, patients, patient guardians, providers, provider organizations, third-party payors, or the like. In some case, providing effective service may require responsive communication among and between the various stakeholders. Further, provider organizations may expend significant resources managing the fluid communication or shared responsibilities among the various parties associated with providing healthcare services. In some cases, determining the service requirements for patients or allocating appropriate provider resources to meet the service requirements may be hindered by communication breakdowns or other hard-to-see issues related to the complexity of relationship between involved parties. In some cases, an absence of actionable information may cause various issues that may impact the cost or efficiency of providing healthcare services. For example. in some cases: patients may be assigned more (or more costly) resources than they actually require; some providers may be over utilized while others may be under utilized; resource or providers may be miss-allocated; or the like. Thus, it is with respect to these considerations and others that the present invention has been made.

BRIEF DESCRIPTION OF THE DRAWINGS

Non-limiting and non-exhaustive embodiments of the present innovations are described with reference to the following drawings. In the drawings, like reference numerals refer to like parts throughout the various figures unless otherwise specified. For a better understanding of the described innovations, reference will be made to the following Detailed Description of Various Embodiments, which is to be read in association with the accompanying drawings, wherein:

FIG. 9 illustrates a representation of a display panel for providing user interfaces for healthcare service platforms in accordance with one or more of the various embodiments;

FIG. 12 illustrates a logical representation of a user interface for providing visit detail user interfaces for healthcare service platforms in accordance with one or more of the various embodiments;

DETAILED DESCRIPTION OF VARIOUS EMBODIMENTS

Figure 1:
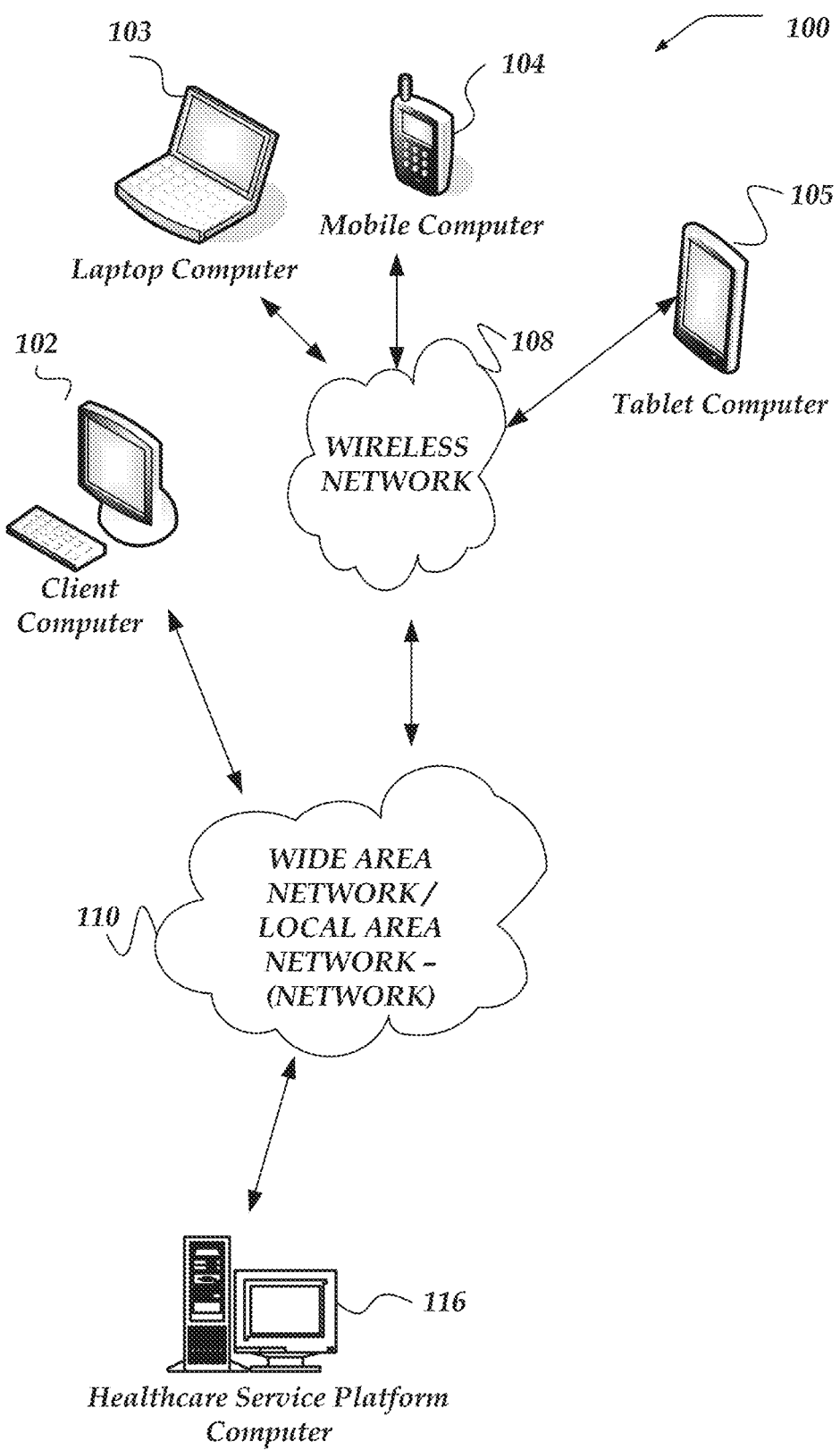
FIG. 1 illustrates a system environment in which various embodiments may be implemented.

Various embodiments now will be described more fully hereinafter with reference to the accompanying drawings, which form a part hereof, and which show, by way of illustration, specific exemplary embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media or devices. Accordingly, the various embodiments may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

For example embodiments, the following terms are also used herein according to the corresponding meaning, unless the context clearly dictates otherwise.

As used herein the term, "engine" refers to logic embodied in hardware or software instructions, which can be written in a programming language, such as C, C++, Objective-C, COBOL, Java™, PHP, Perl, Python, R, Julia, JavaScript, Ruby, VBScript, Microsoft .NET™ languages such as C#, or the like. An engine may be compiled into executable programs or written in interpreted programming languages. Software engines may be callable from other engines or from themselves. Engines described herein refer to one or more logical modules that can be merged with other engines or applications, or can be divided into sub-engines. The engines can be stored in non-transitory computer-readable medium or computer storage device and be stored on and executed by one or more general purpose computers, thus creating a special purpose computer configured to provide the engine.

As used herein, the term "provider" refers to a professional care provider that may be assigned to provide care services for a patient visit. Providers may include physicians, physician assistants, nurse practitioners, nurses, medical assistants, nursing assistants, physical therapists, or the like. In many cases, providers may be individual service providers. In some cases, providers may be third party organizations rather than individuals.

As used herein, the term "provider organization" refers to an organization that provided professional care services to patients. Provider organizations may include large nationwide healthcare networks, state-wide networks, private clinics, independent hospitals, urgent care networks, or the like. Generally, provider organizations represent one or more providers and provide the facilities or administrative support that enable care services to be provided to patients. In some cases, one large provider organization may be comprised of a federation of other smaller provider organizations.

As used herein, the term "patient" refers to person seeking care services from a provider organization or provider. In some cases, a guardian may be providing information or authorizing care for a patient.

As used herein, the term "patient visit profile" refers to one or more data structures that include one or more fields that represent characteristics of a patient and a visit. Patient visit profiles may include fields for patient identity, patient demographics, payor information, or the like. Also, patient visit profiles may include visit information, such as, reason for visit, assigned provider, date of visit, duration of visit, visit resolution information, or the like. Patient visit profiles may provide regularized input to matching engines that may match patient visit profiles with providers. Some or all of the attributed included patient visit profiles may be vectorized of otherwise formatted to be suitable for evaluating with matching models to generate matching scores for matching providers with visits.

As used herein, the term "matching model" refers to one or more data structures, data, instructions, or the like, that may be employed to match providers with visits based on various provided inputs including patient visit profiles. In some cases, matching models may be comprised of one or more sub-models, that may include one or more heuristics, filters, rules, trained machine learning models, or the like.

As used herein, the terms "electronic medical record," or "EMR" refer to digital records that includes health information of an individual.

As used herein, the term, "configuration information" refers to information that may include rule based policies, pattern matching, scripts (e.g., computer readable instructions), or the like, that may be provided from various sources, including, configuration files, databases, user input, built-in defaults, or the like, or combination thereof. In some cases, configuration information may include or reference information stored in other systems or services, such as, configuration management databases, Lightweight Directory Access Protocol (LDAP) servers, name services, public key infrastructure services, or the like.

The following briefly describes embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed to managing the provisioning of healthcare services over a network.

In one or more of the various embodiments, a visit profile may be provided by a patient requesting a visit to obtain healthcare services from a provider organization such that the visit profile includes one or more of a reason for the visit, patient demographic information, or the like.

In one or more of the various embodiments, one or more providers that are associated with the provider organization may be determined.

In one or more of the various embodiments, one or more match scores for the one or more providers may be generated based on one or more matching models and the visit profile such that each match score represents a quality of a match for assigning the one or more providers to the visit requested by the patient.

In one or more of the various embodiments, a provider may be assigned to the visit based on the one or more match scores.

In one or more of the various embodiments, a virtual waiting room may be provided for the patient based on the visit profile such that one or more user interfaces in the virtual waiting room enable one or more interactions between the patient and the virtual waiting room.

In one or more of the various embodiments, the visit profile may be updated with supplemental information based on one or more of interactions between the patient and the virtual waiting room, patient information from one or more data stores, visit information from the one or more data stores, or the like.

In one or more of the various embodiments, one or more updated match scores may be provided for the one or more providers based on the one or more matching models and the updated visit profile.

In one or more of the various embodiments, in response to an updated match score exceeding a previously determined higher match score, another provider may be assigned to the visit based on the other provider being associated with the updated match score such that the visit may be conducted by the other provider.

In one or more of the various embodiments, the one or more interactions between the patient and the virtual waiting room, may include: exchanging text chat messages with the patient and the provider organization to collect data that may represent an improved understanding of patient needs; providing the data to improve or update matching models to improve matching; verifying that the patient has a technical capability to virtually conduct the visit; collecting one or more audio samples from the patient; employing one or more survey questions to collect one or more responses from the patient; or the like.

In one or more of the various embodiments, providing the one or more match scores for the one or more providers may include: determining one or more of the one or more providers that may be qualified based on the visit profile, historical performance and one or more matching models to predict the likelihood of achieving a future performance target such as delivering care with better outcomes or lower costs; determining an availability of each qualified provider based on the visit profile and schedule information; providing the match score for each available qualified provider; or the like.

In one or more of the various embodiments, in response to a conclusion of the visit, further actions may be performed, including: providing one or more user interfaces to the patient; employing the one or more user interfaces to collect patient satisfaction information from the patient; generating novel structured data by mining unstructured information provider by providers or patients; updating the one or more matching models based on the patient satisfaction information; or the like.

In one or more of the various embodiments, in response to a conclusion of the visit, further actions may be performed, including: providing one or more user interfaces to the provider; employing the one or more user interfaces to collect visit resolution information from the provider; updating the one or more matching models based on the visit resolution information. And, in some embodiments, in response to the visit remaining unresolved, further actions may be performed including, reducing a fee associated with the visit; updating the updated visit profile based on the resolution information; providing a referral to a specialist or scheduling another visit based on the updated visit profile, or the like.

In one or more of the various embodiments, generating the one or more match scores for the one or more providers may include: determining one or more first partial match scores based on a utilization metric associated with each provider; determining one or more second partial match scores based on outcome information associated with the one or more providers and an equivalent visit type as the visit; determining one or more third partial match scores based on one or more metrics associated with the visit and one or more policies of the provider organization; providing the one or more match scores based on one or more of the one or more first partial match scores, the one or more second partial match scores, or the one or more third partial match score; or the like.

In one or more of the various embodiments, the patient may be added to one or more visit queues. In some embodiments, a duration that the patient is in the one or more visit queues may be monitored. In some embodiments, in response to the duration that the patient may be in the one or more visit queues exceeds a threshold value, further actions may be performed, including: generating one or more notifications to notify one or more representatives of the provider organization that the queue duration may be exceeding the threshold value; updating the visit profile based on the queue duration exceeding the threshold value; assigning the visit to another provider based on the updated visit profile; placing the patient in a virtual queue and notifying them when the best provider is available to see them; or the like.

Illustrated Operating Environment

FIG. 1 shows components of one embodiment of an environment in which embodiments of the invention may be practiced. Not all of the components may be required to practice the invention, and variations in the arrangement and type of the components may be made without departing from the spirit or scope of the invention. As shown, system 100 of FIG. 1 includes local area networks (LANs)/wide area networks (WANs)—(network) 110, wireless network 108, client computers 102-105, healthcare service platform computer 116, or the like.

At least one embodiment of client computers 102-105 is described in more detail below in conjunction with FIG. 2. In one embodiment, at least some of client computers 102-105 may operate over one or more wired or wireless networks, such as networks 108, or 110. Generally, client computers 102-105 may include virtually any computer capable of communicating over a network to send and receive information, perform various online activities, offline actions, or the like. In one embodiment, one or more of client computers 102-105 may be configured to operate within a business or other entity to perform a variety of services for the business or other entity. For example, client computers 102-105 may be configured to operate as a web server, firewall, client application, media player, mobile telephone, game console, desktop computer, or the like. However, client computers 102-105 are not constrained to these services and may also be employed, for example, as for end-user computing in other embodiments. It should be recognized that more or less client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or the like. In some embodiments, client computers 102-105 may include virtually any portable computer capable of connecting to another computer and receiving information such as, laptop computer 103, mobile computer 104, tablet computers 105, or the like. However, portable computers are not so limited and may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or the like. As such, client computers 102-105 typically range widely in terms of capabilities and features. Moreover, client computers 102-105 may access various computing applications, including a browser, or other web-based application.

A web-enabled client computer may include a browser application that is configured to send requests and receive responses over the web. The browser application may be configured to receive and display graphics, text, multimedia, and the like, employing virtually any web-based language. In one embodiment, the browser application is enabled to employ JavaScript, HyperText Markup Language (HTML), eXtensible Markup Language (XML), JavaScript Object Notation (JSON), Cascading Style Sheets (CS S), or the like, or combination thereof, to display and send a message. In one embodiment, a user of the client computer may employ the browser application to perform various activities over a network (online). However, another application may also be used to perform various online activities.

Client computers 102-105 also may include at least one other client application that is configured to receive or send content between another computer. The client application may include a capability to send or receive content, or the like. The client application may further provide information that identifies itself, including a type, capability, name, and the like. In one embodiment, client computers 102-105 may uniquely identify themselves through any of a variety of mechanisms, including an Internet Protocol (IP) address, a phone number, Mobile Identification Number (MIN), an electronic serial number (ESN), a client certificate, or other device identifier. Such information may be provided in one or more network packets, or the like, sent between other client computers, healthcare service platform computer 116, or other computers.

Client computers 102-105 may further be configured to include a client application that enables an end-user to log into an end-user account that may be managed by another computer, such as healthcare service platform computer 116, or the like. Such an end-user account, in one non-limiting example, may be configured to enable the end-user to manage one or more online activities, including in one non-limiting example, project management, software development, system administration, configuration management, search activities, social networking activities, browse various websites, communicate with other users, or the like. Also, client computers may be arranged to enable users to display reports, interactive user-interfaces, results provided by healthcare service platform computer 116, or the like. Wireless network 108 is configured to couple client computers 103-105 and its components with network 110. Wireless network 108 may include any of a variety of wireless sub-networks that may further overlay stand-alone ad-hoc networks, and the like, to provide an infrastructure-oriented connection for client computers 103-105. Such sub-networks may include mesh networks, Wireless LAN (WLAN) networks, cellular networks, and the like. In one embodiment, the system may include more than one wireless network.

Wireless network 108 may further include an autonomous system of terminals, gateways, routers, and the like connected by wireless radio links, and the like. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G) 5th (5G) generation radio access for cellular systems, WLAN, Wireless Router (WR) mesh, and the like. Access technologies such as 2G, 3G, 4G, 5G, and future access networks may enable wide area coverage for mobile computers, such as client computers 103-105 with various degrees of mobility. In one non-limiting example, wireless network 108 may enable a radio connection through a radio network access such as Global System for Mobile communication (GSM), General Packet Radio Services (GPRS), Enhanced Data GSM Environment (EDGE), code division multiple access (CDMA), time division multiple access (TDMA), Wideband Code Division Multiple Access (WCDMA), High Speed Downlink Packet Access (HSDPA), Long Term Evolution (LTE), and the like. In essence, wireless network 108 may include virtually any wireless communication mechanism by which information may travel between client computers 103-105 and another computer, network, a cloud-based network, a cloud instance, or the like.

Network 110 is configured to couple network computers with other computers, including, healthcare service platform computer 116, client computers 102-105 through wireless network 108, or the like. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, Ethernet port, other forms of computer-readable media, or any combination thereof. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including without limit, for example, DS-0, DS-1, DS-2, DS-3, DS-4, OC-3, OC-12, OC-48, or the like. Furthermore, remote computers and other related electronic devices could be remotely connected to either LANs or WANs via a modem and temporary telephone link. In one embodiment, network 110 may be configured to transport information using one or more network protocols, such Internet Protocol (IP).

Additionally, communication media typically embodies computer readable instructions, data structures, program modules, or other transport mechanism and includes any information non-transitory delivery media or transitory delivery media. By way of example, communication media includes wired media such as twisted pair, coaxial cable, fiber optics, wave guides, and other wired media and wireless media such as acoustic, RF, infrared, and other wireless media.

One embodiment of healthcare service platform computer 116 is described in more detail below in conjunction with FIG. 3. Although FIG. 1 illustrates healthcare service platform computer 116 as a single computer, the innovations or embodiments are not so limited. For example, one or more functions of healthcare service platform computer 116, or the like, may be distributed across one or more distinct network computers. Moreover, in one or more embodiments, healthcare service platform computer 116 may be implemented using a plurality of network computers. Further, in one or more of the various embodiments, healthcare service platform computer 116 may be implemented using one or more cloud instances in one or more cloud networks. Accordingly, these innovations and embodiments are not to be construed as being limited to a single environment, and other configurations, and other architectures are also envisaged.

Illustrative Client Computer

Figure 2:
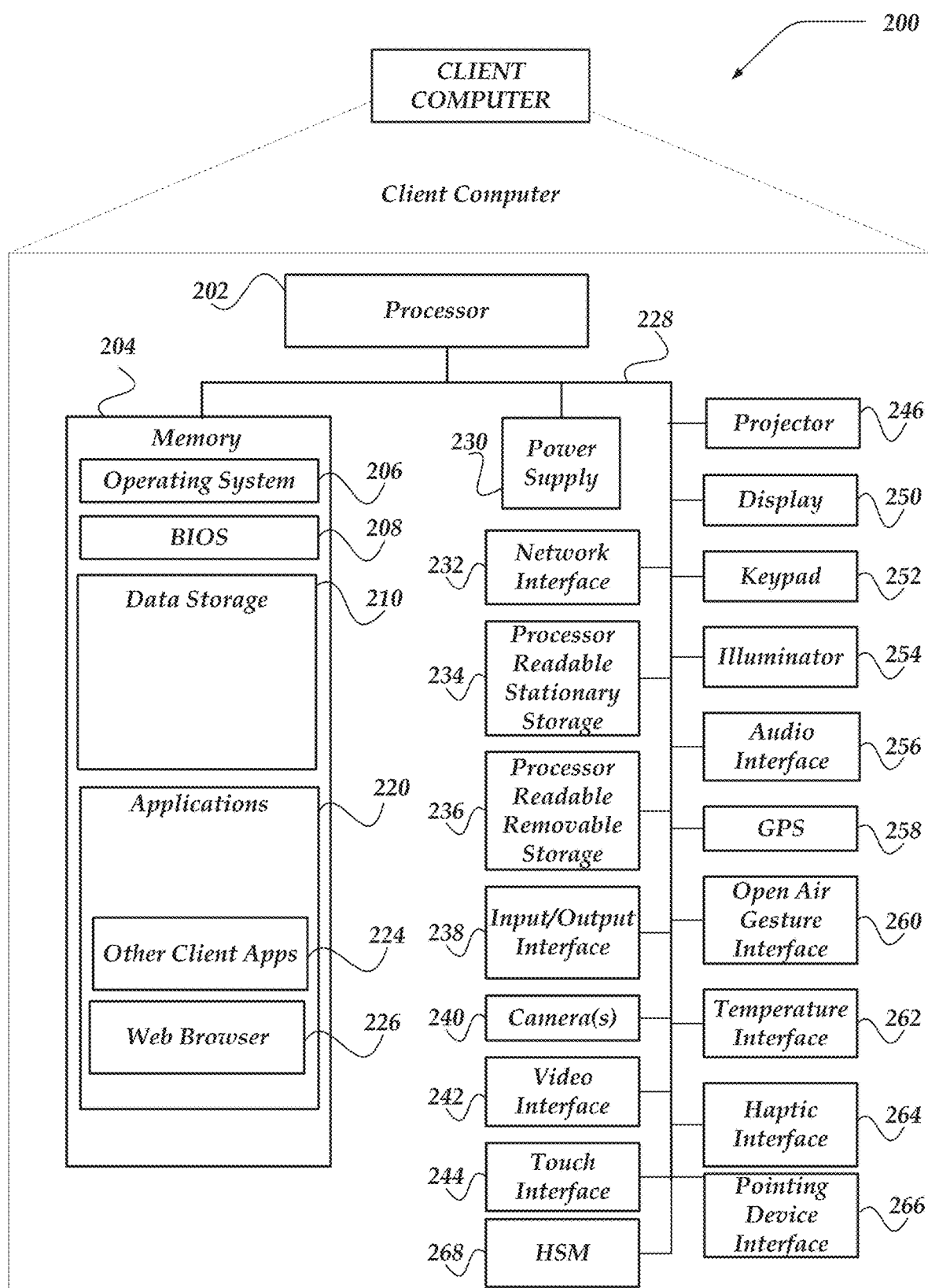
FIG. 2 illustrates a schematic embodiment of a client computer.

FIG. 2 shows one embodiment of client computer 200 that may include many more or less components than those shown. Client computer 200 may represent, for example, at least one embodiment of mobile computers or client computers shown in FIG. 1.

Client computer 200 may include processor 202 in communication with memory 204 via bus 228. Client computer 200 may also include power supply 230, network interface 232, audio interface 256, display 250, keypad 252, illuminator 254, video interface 242, input/output interface 238, haptic interface 264, global positioning systems (GPS) receiver 258, open air gesture interface 260, temperature interface 262, camera(s) 240, projector 246, pointing device interface 266, processor-readable stationary storage device 234, and processor-readable removable storage device 236. Client computer 200 may optionally communicate with a base station (not shown), or directly with another computer. And in one embodiment, although not shown, a gyroscope may be employed within client computer 200 for measuring or maintaining an orientation of client computer 200.

Power supply 230 may provide power to client computer 200. A rechargeable or non-rechargeable battery may be used to provide power. The power may also be provided by an external power source, such as an AC adapter or a powered docking cradle that supplements or recharges the battery.

Network interface 232 includes circuitry for coupling client computer 200 to one or more networks, and is constructed for use with one or more communication protocols and technologies including, but not limited to, protocols and technologies that implement any portion of the OSI model for mobile communication (GSM), CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (NIC).

Audio interface 256 may be arranged to produce and receive audio signals such as the sound of a human voice. For example, audio interface 256 may be coupled to a speaker and microphone (not shown) to enable telecommunication with others or generate an audio acknowledgement for some action. A microphone in audio interface 256 can also be used for input to or control of client computer 200, e.g., using voice recognition, detecting touch based on sound, and the like.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication or provide light. Illuminator 254 may remain active for specific periods of time or in response to event messages. For example, when illuminator 254 is active, it may backlight the buttons on keypad 252 and stay on while the client computer is powered. Also, illuminator 254 may backlight these buttons in various patterns when particular actions are performed, such as dialing another client computer. Illuminator 254 may also cause light sources positioned within a transparent or translucent case of the client computer to illuminate in response to actions.

Further, client computer 200 may also comprise hardware security module (HSM) 268 for providing additional tamper resistant safeguards for generating, storing or using security/cryptographic information such as, keys, digital certificates, passwords, passphrases, two-factor authentication information, or the like. In some embodiments, hardware security module may be employed to support one or more standard public key infrastructures (PKI), and may be employed to generate, manage, or store keys pairs, or the like. In some embodiments, HSM 268 may be a stand-alone computer, in other cases, HSM 268 may be arranged as a hardware card that may be added to a client computer.

Client computer 200 may also comprise input/output interface 238 for communicating with external peripheral devices or other computers such as other client computers and network computers. The peripheral devices may include an audio headset, virtual reality headsets, display screen glasses, remote speaker system, remote speaker and microphone system, and the like. Input/output interface 238 can utilize one or more technologies, such as Universal Serial Bus (USB), Infrared, WiFi, WiMax, Bluetooth™, and the like.

Input/output interface 238 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect or measure data that is external to client computer 200.

Haptic interface 264 may be arranged to provide tactile feedback to a user of the client computer. For example, the haptic interface 264 may be employed to vibrate client computer 200 in a particular way when another user of a computer is calling. Temperature interface 262 may be used to provide a temperature measurement input or a temperature changing output to a user of client computer 200. Open air gesture interface 260 may sense physical gestures of a user of client computer 200, for example, by using single or stereo video cameras, radar, a gyroscopic sensor inside a computer held or worn by the user, or the like. Camera 240 may be used to track physical eye movements of a user of client computer 200.

GPS transceiver 258 can determine the physical coordinates of client computer 200 on the surface of the Earth, which typically outputs a location as latitude and longitude values. GPS transceiver 258 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of client computer 200 on the surface of the Earth. It is understood that under different conditions, GPS transceiver 258 can determine a physical location for client computer 200. In one or more embodiments, however, client computer 200 may, through other components, provide other information that may be employed to determine a physical location of the client computer, including for example, a Media Access Control (MAC) address, IP address, and the like.

Human interface components can be peripheral devices that are physically separate from client computer 200, allowing for remote input or output to client computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Zigbee™ and the like. One non-limiting example of a client computer with such peripheral human interface components is a wearable computer, which might include a remote pico projector along with one or more cameras that remotely communicate with a separately located client computer to sense a user's gestures toward portions of an image projected by the pico projector onto a reflected surface such as a wall or the user's hand.

A client computer may include web browser application 226 that is configured to receive and to send web pages, web-based messages, graphics, text, multimedia, and the like. The client computer's browser application may employ virtually any programming language, including a wireless application protocol messages (WAP), and the like. In one or more embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, and the like.

Memory 204 may include RAM, ROM, or other types of memory. Memory 204 illustrates an example of computer-readable storage media (devices) for storage of information such as computer-readable instructions, data structures, program modules or other data. Memory 204 may store BIOS 208 for controlling low-level operation of client computer 200. The memory may also store operating system 206 for controlling the operation of client computer 200. It will be appreciated that this component may include a general-purpose operating system such as a version of UNIX®, or Linux®, or a specialized client computer communication operating system such as Windows Phone™, or the Symbian® operating system. The operating system may include, or interface with a Java virtual machine module that enables control of hardware components or operating system operations via Java application programs.

Memory 204 may further include one or more data storage 210, which can be utilized by client computer 200 to store, among other things, applications 220 or other data. For example, data storage 210 may also be employed to store information that describes various capabilities of client computer 200. The information may then be provided to another device or computer based on any of a variety of methods, including being sent as part of a header during a communication, sent upon request, or the like. Data storage 210 may also be employed to store social networking information including address books, buddy lists, aliases, user profile information, or the like. Data storage 210 may further include program code, data, algorithms, and the like, for use by a processor, such as processor 202 to execute and perform actions. In one embodiment, at least some of data storage 210 might also be stored on another component of client computer 200, including, but not limited to, non-transitory processor-readable removable storage device 236, processor-readable stationary storage device 234, or even external to the client computer.

Applications 220 may include computer executable instructions which, when executed by client computer 200, transmit, receive, or otherwise process instructions and data. Applications 220 may include, for example, other client applications 224, web browser 226, or the like. Client computers may be arranged to exchange communications, such as, queries, searches, messages, notification messages, event messages, alerts, performance metrics, log data, API calls, or the like, combination thereof, with healthcare service platforms. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Additionally, in one or more embodiments (not shown in the figures), client computer 200 may include one or more embedded logic hardware devices instead of CPUs, such as, an Application Specific Integrated Circuit (ASIC), Field Programmable Gate Array (FPGA), Programmable Array Logic (PAL), or the like, or combination thereof. The embedded logic hardware devices may directly execute embedded logic to perform actions. Also, in one or more embodiments (not shown in the figures), client computer 200 may include one or more hardware microcontrollers instead of CPUs. In one or more embodiments, the microcontrollers may directly execute their own embedded logic to perform actions and access their own internal memory and their own external Input and Output Interfaces (e.g., hardware pins or wireless transceivers) to perform actions, such as System On a Chip (SOC), or the like.

Illustrative Network Computer

Figure 3:
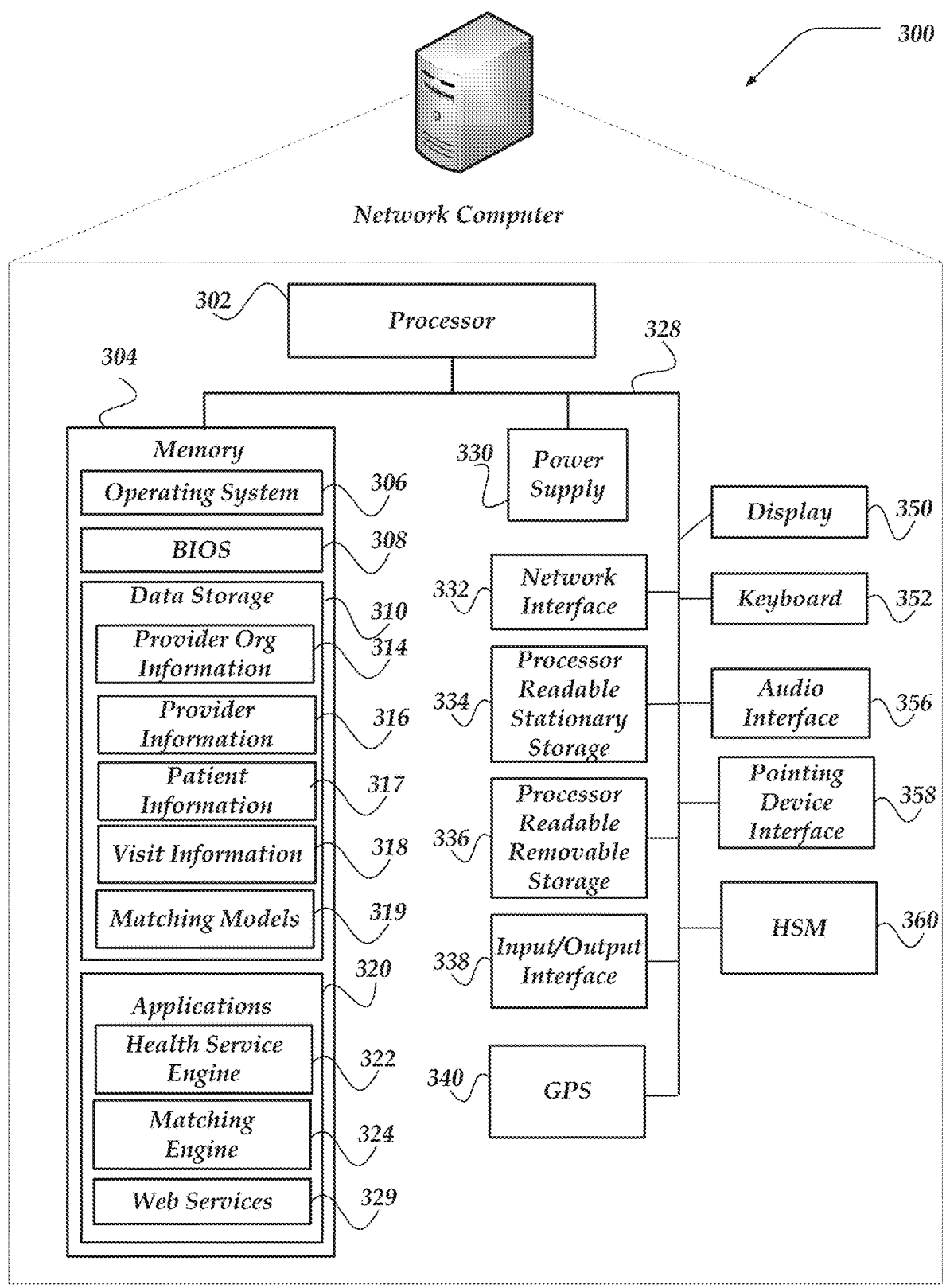
FIG. 3 illustrates a schematic embodiment of a network computer.

FIG. 3 shows one embodiment of network computer 300 that may be included in a system implementing at least one of the various embodiments. Network computer 300 may include many more or less components than those shown in FIG. 3. However, the components shown are sufficient to disclose an illustrative embodiment for practicing these innovations. Network computer 300 may represent, for example, one embodiment of healthcare service platform computer 116 of FIG. 1.

As shown in the figure, network computer 300 includes a processor 302 that may be in communication with a memory 304 via a bus 328. In some embodiments, processor 302 may be comprised of one or more hardware processors, or one or more processor cores. In some cases, one or more of the one or more processors may be specialized processors designed to perform one or more specialized actions, such as, those described herein. Network computer 300 also includes a power supply 330, network interface 332, audio interface 356, display 350, keyboard 352, input/output interface 338, processor-readable stationary storage device 334, and processor-readable removable storage device 336. Power supply 330 provides power to network computer 300.

Network interface 332 includes circuitry for coupling network computer 300 to one or more networks, and is constructed for use with one or more communication protocols and technologies including, but not limited to, protocols and technologies that implement any portion of the Open Systems Interconnection model (OSI model), global system for mobile communication (GSM), code division multiple access (CDMA), time division multiple access (TDMA), user datagram protocol (UDP), transmission control protocol/Internet protocol (TCP/IP), Short Message Service (SMS), Multimedia Messaging Service (MMS), general packet radio service (GPRS), WAP, ultra-wide band (UWB), IEEE 802.16 Worldwide Interoperability for Microwave Access (WiMax), Session Initiation Protocol/Realtime Transport Protocol (SIP/RTP), or any of a variety of other wired and wireless communication protocols. Network interface 332 is sometimes known as a transceiver, transceiving device, or network interface card (NIC). Network computer 300 may optionally communicate with a base station (not shown), or directly with another computer.

Audio interface 356 is arranged to produce and receive audio signals such as the sound of a human voice. For example, audio interface 356 may be coupled to a speaker and microphone (not shown) to enable telecommunication with others or generate an audio acknowledgement for some action. A microphone in audio interface 356 can also be used for input to or control of network computer 300, for example, using voice recognition.

Display 350 may be a liquid crystal display (LCD), gas plasma, electronic ink, light emitting diode (LED), Organic LED (OLED) or any other type of light reflective or light transmissive display that can be used with a computer. In some embodiments, display 350 may be a handheld projector or pico projector capable of projecting an image on a wall or other object.

Network computer 300 may also comprise input/output interface 338 for communicating with external devices or computers not shown in FIG. 3. Input/output interface 338 can utilize one or more wired or wireless communication technologies, such as USB™, Firewire™, WiFi, WiMax, Thunderbolt™, Infrared, Bluetooth™, Zigbee™, serial port, parallel port, and the like.

Also, input/output interface 338 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or the like), or the like. Sensors may be one or more hardware sensors that collect or measure data that is external to network computer 300. Human interface components can be physically separate from network computer 300, allowing for remote input or output to network computer 300. For example, information routed as described here through human interface components such as display 350 or keyboard 352 can instead be routed through the network interface 332 to appropriate human interface components located elsewhere on the network. Human interface components include any component that allows the computer to take input from, or send output to, a human user of a computer. Accordingly, pointing devices such as mice, styluses, track balls, or the like, may communicate through pointing device interface 358 to receive user input.

GPS transceiver 340 can determine the physical coordinates of network computer 300 on the surface of the Earth, which typically outputs a location as latitude and longitude values. GPS transceiver 340 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of network computer 300 on the surface of the Earth. It is understood that under different conditions, GPS transceiver 340 can determine a physical location for network computer 300. In one or more embodiment, however, network computer 300 may, through other components, provide other information that may be employed to determine a physical location of the client computer, including for example, a Media Access Control (MAC) address, IP address, and the like.

In at least one of the various embodiments, applications, such as, operating system 306, healthcare service engine 322, matching engine 324, web services 329, or the like, may be arranged to employ geo-location information to select one or more localization features, such as, time zones, languages, currencies, calendar formatting, or the like. Localization features may be used when scheduling/visit information, provider availability, patient preferences, user-interfaces, generating reports, as well as internal processes or databases. In at least one of the various embodiments, geo-location information used for selecting localization information may be provided by GPS 340. Also, in some embodiments, geolocation information may include information provided using one or more geolocation protocols over the networks, such as, wireless network 108 or network 111.

Memory 304 may include Random Access Memory (RAM), Read-Only Memory (ROM), or other types of memory. Memory 304 illustrates an example of computer-readable storage media (devices) for storage of information such as computer-readable instructions, data structures, program modules or other data. Memory 304 stores a basic input/output system (BIOS) 308 for controlling low-level operation of network computer 300. The memory also stores an operating system 306 for controlling the operation of network computer 300. It will be appreciated that this component may include a general-purpose operating system such as a version of UNIX, or Linux®, or a specialized operating system such as Microsoft Corporation's Windows® operating system, or the Apple Corporation's IOS® operating system. The operating system may include, or interface with a Java virtual machine (JVM) or other run-time engines that enable control of hardware components or operating system operations via application programs executed the JVM or other run-time execution engines.

Memory 304 may further include one or more data storage 310, which can be utilized by network computer 300 to store, among other things, applications 320 or other data. For example, data storage 310 may also be employed to store information that describes various capabilities of network computer 300. The information may then be provided to another device or computer based on any of a variety of methods, including being sent as part of a header during a communication, sent upon request, or the like. Data storage 310 may also be employed to store social networking information including address books, buddy lists, aliases, user profile information, or the like. Data storage 310 may further include program code, data, algorithms, and the like, for use by a processor, such as processor 302 to execute and perform actions such as those actions described below. In one embodiment, at least some of data storage 310 might also be stored on another component of network computer 300, including, but not limited to, non-transitory media inside processor-readable removable storage device 336, processor-readable stationary storage device 334, or any other computer-readable storage device within network computer 300, or even external to network computer 300. Data storage 310 may include, for example, provider organization information, 314, provider information 316, patient information 317, visit information 318, matching models 319, or the like.

Applications 320 may include computer executable instructions which, when executed by network computer 300, transmit, receive, or otherwise process messages (e.g., SMS, Multimedia Messaging Service (MMS), Instant Message (IM), email, or other messages), audio, video, and enable telecommunication with another user of another mobile computer. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth. Applications 320 may include healthcare service engine 322, matching engine 324, web services 329, or the like, that may be arranged to perform actions for embodiments described below. In one or more of the various embodiments, one or more of the applications may be implemented as modules or components of another application. Further, in one or more of the various embodiments, applications may be implemented as operating system extensions, modules, plugins, or the like.

Furthermore, in one or more of the various embodiments, healthcare service engine 322, matching engine 324, web services 329, or the like, may be operative in a cloud-based computing environment. In one or more of the various embodiments, these applications, and others, that comprise a healthcare service platform may be executing within virtual machines or virtual servers that may be managed in a cloud-based based computing environment. In one or more of the various embodiments, in this context the applications may flow from one physical network computer within the cloud-based environment to another depending on performance and scaling considerations automatically managed by the cloud computing environment. Likewise, in one or more of the various embodiments, virtual machines or virtual servers dedicated to healthcare service engine 322, matching engine 324, web services 329, or the like, may be provisioned and de-commissioned automatically.

Also, in one or more of the various embodiments, healthcare service engine 322, matching engine 324, web services 329, or the like, may be located in virtual servers running in a cloud-based computing environment rather than being tied to one or more specific physical network computers. Likewise, in some embodiments, one or more of healthcare service platform 322, matching engine 324, web services 329, or the like, may be configured to execute in a container-based environment.

Further, network computer 300 may also comprise hardware security module (HSM) 360 for providing additional tamper resistant safeguards for generating, storing or using security/cryptographic information such as, keys, digital certificates, passwords, passphrases, two-factor authentication information, or the like. In some embodiments, hardware security modules may be employed to support one or more standard public key infrastructures (PKI), and may be employed to generate, manage, or store keys pairs, or the like. In some embodiments, HSM 360 may be a stand-alone network computer, in other cases, HSM 360 may be arranged as a hardware card that may be installed in a network computer.

Additionally, in one or more embodiments (not shown in the figures), network computer 300 may include one or more embedded logic hardware devices instead of CPUs, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. Also, in one or more embodiments (not shown in the figures), the network computer may include one or more hardware microcontrollers instead of CPUs. In one or more embodiments, the one or more microcontrollers may directly execute their own embedded logic to perform actions and access their own internal memory and their own external Input and Output Interfaces (e.g., hardware pins or wireless transceivers) to perform actions, such as System On a Chip (SOC), or the like.

Illustrative Logical System Architecture

Figure 4:
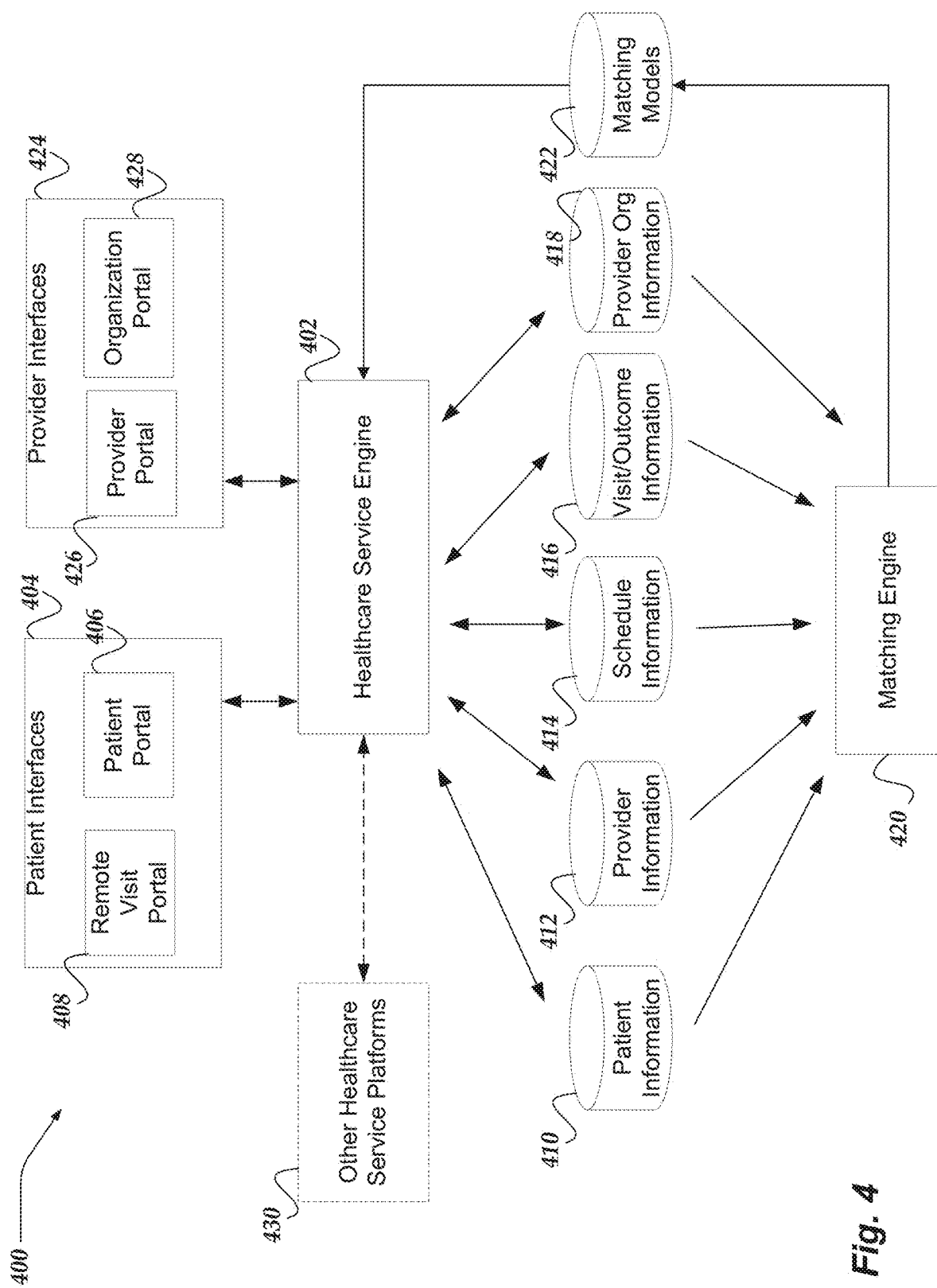
FIG. 4 illustrates a logical architecture of a system for healthcare service platform in accordance with one or more of the various embodiments.

FIG. 4 illustrates a logical architecture of system 400 for healthcare service platform in accordance with one or more of the various embodiments. In one or more of the various embodiments, healthcare service platforms may be comprised of various elements, including, healthcare service engine 402, patient interfaces 404, remote visit portal 406, patient portal 408, patient information data store 410, provider information data store 410, schedule information data store 410, visit/outcome information data store 410, matching engine(s) 420, learned models data store 422, provider interfaces 424, provider portal 426, provider organization portal 428, or the like.

Also, in some cases, for some embodiments, one or more healthcare service platforms may be configured to communicate/coordinate with one or more other healthcare service platforms, such as, other healthcare service platforms 424.

In one or more of the various embodiments, healthcare service engines, such as, healthcare service engine 402 may be arranged to process various requests from patients, providers, or provider organizations. In some embodiments, healthcare service engines may be arranged to process requests from one or more authorized third-party services, such as, insurance providers, or the like. In some embodiments, healthcare service engines may be arranged to exchange information with other third-party services, such as, EHR systems, hospital management systems, billing services, or the like. In some embodiments, healthcare service engines may be arranged to enable patients to schedule visits with providers. Also, in some embodiments, healthcare service engines may be arranged to enable provider organizations to manage patients, providers, visits, or the like.

In one or more of the various embodiments, healthcare service platforms may be arranged to provide one or more patient interfaces, such as patient interfaces 404. In some embodiments, patient interfaces 404 represent one or more user interfaces or APIs that may employed by patients or services on behalf of patients to access healthcare services.

In some embodiments, patient interfaces may provide one or more patient portals, such as, patient portal 406. In one or more of the various embodiments, patient portals may be arranged to provide interactive reports, user interfaces, or the like, that enable patients to view or interact with their healthcare providers. In some embodiments, patient portals may be arranged to enable patients to review upcoming appointments, past appointments, request new appointments, or the like. Further, in some embodiments, patient portals may be arranged to enable to patients to view some or all of their electronic health records (EHRs). In some embodiments, patient portals may be communicatively coupled with healthcare service engine 402 using one or more networks. Accordingly, in some embodiments, healthcare service engines may be arranged to provide the information that may be presented in the patient portal.

In one or more of the various embodiments, provider organizations may be enabled to customize user interfaces or reports that may be provided to their patients, including the care settings, providers and modalities that may be best for them based upon their interests, motivations and clinical needs. In some embodiments, portions of patient portals may be customized by patients. In some embodiments, healthcare service engines may be arranged to determine the user interfaces or reports that may be presented or accessed from patient portals based on rules, instructions, or the like, provided via configuration information to account for local circumstances or local requirements.

In one or more of the various embodiments, patient portals may be comprised of one or more mobile applications, desktop applications, web-based applications, or the like.

In one or more of the various embodiments, patient interfaces 404 may be arranged to provide remote visit portals, such as, remote visit portal 408. In one or more of the various embodiments, remote visit portals may be arranged to enable patients and providers to conduct scheduled visits using video conferencing, teleconferencing, or the like, or combination thereof. In some embodiments, remote visit portals may be arranged to include virtual waiting rooms that enable providers/provider organizations to request or collect pertinent information from patients that may be queued for scheduled visits.

In some embodiments, remote visit portals may be arranged to provide user interfaces for chat services that enable incoming patients to describe symptoms, submit questions, or the like. In some embodiments, healthcare service engines may be arranged to provide both computer automated chat systems (e.g., chat bots) as well as human monitored chat services.

In one or more of the various embodiments, healthcare service engines, such as, healthcare service engine 402 may be arranged to employ one or more data stores to collect or organize some or all of the information associated with providing healthcare services. In some embodiments, the one or more data stores may include data stores, such as, patient information data store 410, provider information data store 412, schedule information data store 414, visit/outcome information data store 416, provider organization information data store 418, or the like. Accordingly, in some embodiments, healthcare service engines may be enabled to store various information associated patients, providers, or provider organizations, such as, vital information, administrative information, billing/payment information, insurance information, visit history, scheduled appointments, medical history, financial information, performance tracking information, resource utilization information, or the like. In some embodiments, healthcare service engine may be arranged to provide EHRs for patients.

Alternatively, in some embodiments, healthcare service engines may integrate with one or more authorized EHR providers rather than acting as a repository for EHRs. Accordingly, in some embodiments, healthcare service engines may be arranged to exchange some information with authorized EHRs rather than storing EHR information in local data stores.

Likewise, in some embodiments, healthcare service engines may be enabled to store various information associated with providers, such as, availability information, utilization information, specialty information, training/education information, compensation information, visit outcome information, scheduled appointments, or the like.

Also, in one or more of the various embodiments, healthcare service platforms may include one or more matching engines, such as, matching engine 420, or the like. In some embodiments, matching engines may be arranged to employ information collected by healthcare service engines for training or generating one or more machine learning models, including one or more predictive models, one or more classification models, or the like. In some embodiments, matching engine 420 may be enabled to access the various data stores to train one or more matching models that may be stored in matching model data stores, such as, matching data store 422.

In one or more of the various embodiments, healthcare service platforms may be arranged to include matching engines that may apply different machine learning techniques to train models for a variety of applications. Accordingly, in some embodiments, healthcare service engines or matching engines may be arranged to employ configuration information to determine which actions to perform for machine learning. For example, matching engine 420 may be arranged to dynamically load or instantiate one or more machine learning trainers based on configuration information to account for local circumstances or local requirements. In some embodiments, one or more machine learning engines may be hosted in computing environments that may be separate from healthcare service engines. For example, in some embodiments, healthcare service platforms may be arranged to employ one or more off-site machine learning compute clusters hosted in a cloud computing environment to train matching models for the healthcare service platform.

Also, in some embodiments, healthcare service engines may be arranged to provide one or more provider interfaces, such as, provider interfaces 424 that enable providers or provider organizations (e.g., administrative personnel, or the like) to engage with the healthcare service engines. Accordingly, in some embodiments, provider interfaces may include one or more provider portals, such as, provider portal 426 that may enable providers to review practice related information, such as, upcoming appointments, or the like. In some embodiments, provider portals may be arranged to enable providers to communicate with patients (e.g., secure messaging), review past visits, accept/decline visit requests, approve/disapprove treatment requests, approve/disapprove prescription requests, or the like.

Also, in one or more of the various embodiments, provider interfaces may be arranged to provide provider organization portals that enable provider organization representatives to review or interact with practice related information. In some embodiments, provider organization portals may include some information or user interfaces that may be similar to provider portals, except rather than being limited to one provider, provider portals may include information (e.g., patient queues, schedules, visit history, or the like) associated with more than one or more provider. For example, in some embodiments, provider portals may include scheduling/visit information for an entire healthcare network, hospital, clinic, specialty group, or the like.

In one or more of the various embodiments, healthcare service engines may be arranged to restrict access to the information included in provider portal based on the organizational structure of the provider organizations. Accordingly, in some embodiments, one or more users of a provider portal may have access to different information. For example, in some embodiments, a healthcare service engine may provide a provider portal scoped to multiple clinic/hospital locations in a healthcare network while other provider portals may be scoped to one location or one group within the same healthcare network.

Further, in some embodiments, healthcare service engines may be arranged to integrate with one or more other healthcare service platforms, such as, other healthcare service platforms 430. In some embodiments, healthcare service engine may be arranged to rely on other healthcare service platforms to store some or all patient information, provider information, scheduling information, or the like. For example, healthcare service engines may be arranged to communicate with the other healthcare service platforms to access or update patient information.

Figure 5:
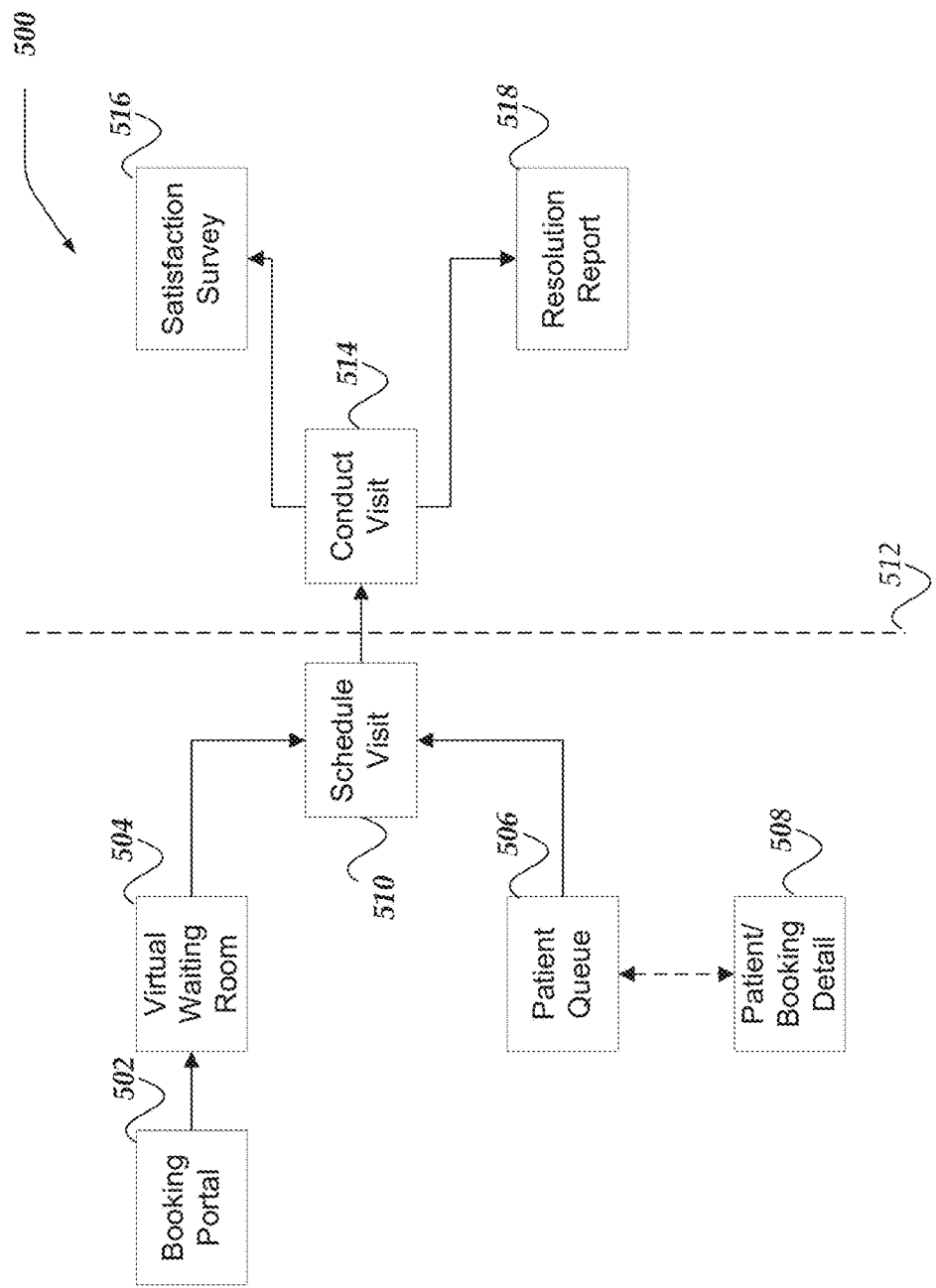
FIG. 5 illustrates a logical schematic of a workflow for patient/provider interactions via a healthcare service platform in accordance with one or more of the various embodiments.

FIG. 5 illustrates a logical schematic of workflow 500 for patient/provider interactions via a healthcare service platform in accordance with one or more of the various embodiments. In one or more of the various embodiments, healthcare service engines may be arranged to provide one or more user interfaces that enable patients to request or receive various healthcare services from one or more providers. In one or more of the various embodiments, healthcare service engines may be arranged to collect information from patients, providers, provider administrators, or the like, to facilitate efficient or effective utilization of provider resources and patient time.

Accordingly, in this example, workflow 500 represents some of the major stages for providing healthcare services via a healthcare service platform. One of ordinary skill in the art will appreciate that there may be more or less stages than shown here without departing from the scope of these innovations. However, workflow 500 is at least sufficient for disclosing features of the disclosed innovations.

In some embodiments, healthcare service engines may be arranged to provide one or more user interfaces represented by booking portal stage 502. In one or more of the various embodiments, these user interfaces may enable patients to submit various demographic information or sociographic (e.g., name, age, contact information, or the like). Also, in some embodiments, booking portals may include user interfaces that enable patients to provide insurance information, patient identifiers (for known/registered patients), location preferences, time/day preferences, or the like. Further, in some embodiments, booking portals may include user interfaces that enable patients to provide information associated with the reason for their visit request, including symptom description, perceived illness description, medical history, or the like.

In some embodiments, if the patient proceeds through the initial booking user interfaces, they may be provided one or more user interfaces represented by virtual waiting room stage 504. In some embodiments, virtual waiting room stage 504 may be user interfaces that a patient may access while waiting for their visit to be scheduled, provider to be assigned, or visit to be conducted. In some embodiments, virtual waiting rooms may provide interactive chat services, additional user interfaces to collect further supplemental patient/visit information, or the like.

In some embodiments, if a patient is seeking a remote or virtual visit, a technical capability check may be conducted to ensure that they have hardware/software sufficient to participate in a virtual visit. In some cases, healthcare service engines may be arranged to provide one or more web-based or downloadable software agents that may collect some or all of the metrics for conducting the technical capability check.

Further, in some embodiments, even though a patient's hardware/software system has the capability to conduct virtual visits, the patient may be unfamiliar with how to activate/enable the software or peripherals that may be necessary for conducting virtual visits. Accordingly, in some embodiments, healthcare service engines may be arranged to enable representatives of the provider organization to communicate with the patient to help configure their hardware/software for the virtual visit. For example, in some embodiments, a provider organization may monitor how pending patients are progressing through a booking process. And, in this example, if necessary, the representative may communicate with the patient via chat, voice telephone, text/SMS, or the like, to help the patient configure their hardware or software for a virtual visit.

In one or more of the various embodiments, healthcare service engines may be arranged to provide one or more user interfaces for providers or provider organizations that enable them to observe or monitor patients that may be booking visits. Accordingly, in this example, at patient queue stage 506 the one or more user interfaces may be provided for observing or monitoring patients.

In one or more of the various embodiments, healthcare service engines may be arranged to provide user interfaces for the patient queue stage that include one or more lists of patients, providers, pending visits, upcoming visits, completed visits, or the like.

Further, as discussed above, patient queue stages may include user interfaces that indicate if a patient is "stuck" at a particular step. Thus, in some embodiments, a provider organization representative may be enabled to intervene or otherwise investigate why the patient may be having difficulty completing the booking process.

Also, in some embodiments, patient queue user interfaces may include visual or audio alarms or notifications that may indicate if a patient may require immediate attention. For example, in some cases, a patient may have self-reported symptoms that indicate the possibility that they may be experiencing a medical emergency, or the like. Accordingly, in this example, for some embodiments, the patient/visit details user interface may activate an alarm or notification to enable a provider or provider organization representative to perform the appropriate emergency response (e.g., contact emergency services on behalf of the patient).

In one or more of the various embodiments, healthcare service engines may be arranged to provide one or more user interfaces represented by patient/booking detail stage 508 that may enable providers or provider organizations to view details of a patient that may be in a virtual waiting room. In some embodiments, patient/booking detail user interfaces may include demographic or sociographic information collected/known about the patient, chat interfaces, wait timers, status information, type of visit request, reason(s) for visit, patient self-reported symptoms, or the like. In some embodiments, patient/booking detail user interfaces may include visual or audio alarms or notifications that may indicate if the patient may require immediate attention. For example, in some cases, the patient may have self-reported symptoms that indicate the possibility that they may be experiencing a medical emergency, or the like. Accordingly, in this example, for some embodiments, the patient/booking detail user interface may activate an alarm to enable a provider or provider representative to perform the appropriate emergency response (e.g., call 911 on behalf of the patient), or automatically present, route to and book for the patient care options appropriate for the level of care required.

In one or more of the various embodiments, patient queue user interfaces may include a list of patients that are queued for visits or scheduling. Also, in some embodiments, patient queue user interfaces directed to provider organizations may include one or more list of providers. Such lists may indicate if a provider may be available, currently conducting a visit, unavailable/absent, or the like. In some embodiments, healthcare service engines may be arranged to provide patient lists or provider lists that include additional information, such as, wait time, geographical location, provider utilization information, match scores, or the like.

In one or more of the various embodiments, at stage 510, a visit may be scheduled for the patient. In some embodiments, healthcare service engines may be arranged to automatically schedule the patient for a visit based on matching models that includes heuristics, rules, machine learning models, or the like. In some embodiments, healthcare service engines may be arranged to employ the matching models to associate a patient with a specific time period, provider, care setting, or visit modality. In some embodiments, in some cases, healthcare service engines may be arranged to enable a provider or provider organization administrator to approve, confirm, modify, or override the scheduling decision before it becomes final.

Likewise, in some embodiments, healthcare service engines may be arranged to present a list of recommended visit options, including care modalities, care settings or care providers, to the patient, enabling the patient to select a preferred visit. Furthermore, in some embodiments, the recommended visit options may be arranged across care settings, modalities, or providers such that, for example, the available appointments for a specific time may be aggregated and displayed as a single appointment booking opportunity for that time rather than displaying the same appointment time repeatedly for each provider or care setting. This may enable a cleaner, less confusing and more actionable care search, display and booking experience for the consumer while also enabling the provider organization to match the best provider for a visit based upon the match score derived from our predictive algorithms and rules-engines.

In one or more of the various embodiments, healthcare service engines may automatically recommend different visit modalities depending on the various factors, including, patient history, reason(s) for visit, information learned from patient's time in a virtual waiting room, provider preferences, provider organization preferences, patient preferences, clinic/provider utilization, clinic specialties, cost, insurance provider preferences, or the like. In some embodiments, healthcare service engines may be arranged to employ rules, heuristics, machine learning models, or the like, that may be included or incorporated in matching models. Accordingly, in some embodiments, healthcare service engines may be arranged to employ rules, models, instructions, conditions, or the like, provided via configuration information to account for local circumstances or local requirements.

In one or more of the various embodiments, healthcare service engines may be arranged to enable intelligent routing, resource optimization and data driven intelligence across disparate provider organizations rather than being limited to one provider organization. Accordingly, in some embodiments, healthcare service engines may be configured to enable provider organizations to route and share patients to other provider organizations depending on local circumstances, such as, during off hour scheduling, provider utilization, or patient location (e.g., travelling patients).

In this example, line 512 represents a division between booking workflow and visit workflow. Accordingly, in some embodiments, if a visit may be scheduled and confirmed, the booking portion of the workflow may be considered complete.

At stage 514, for some embodiments, a visit may be conducted. In some embodiments, the details with how the visit may be conducted may depending on various factors, including, visit modality, provider preference, provider organization preference, purpose of visit, or the like. In some embodiments, visit modalities may include remote video visits, remote telephonic visits, in-person visits, or the like. In some embodiments, healthcare service engines may be arranged employ one or more third-party services to provide the communication (e.g., video, audio, chat, or the like) for remote modality visits.

In one or more of the various embodiments, at the conclusion of the visit, the patient may be enabled to provide information at stage 516 regarding their subjective view of the visit, as well as objective information. In some embodiments, healthcare service engines may be arranged to provide immediate online surveys at the conclusion of remote visits. Alternatively, in some embodiments, healthcare service engines may contact the patient a later time to collect the information for the satisfaction survey or for other patient or visit information. For example, healthcare service engines may be arranged to provide user interfaces that enable patients to delay/defer submitting survey information. Also, in some embodiments, healthcare service engines may be arranged to provide user interfaces to collect survey information after in-person visits. For example, healthcare service engines may be arranged to provide emails, texts, notifications, or the like, to patients via the mobile phone applications, web-based applications, desktop applications, or the like, that invite the patients to provide satisfaction or other patient or visit information.

Similarly, in one or more of the various embodiments, healthcare service engines may be arranged to provide one or more user interfaces that enable providers to provide information for a visit resolution report. In some embodiments, healthcare service engines may be configured to require providers to complete the report to formally close/finish the visit. In some embodiments, provider portals may include user interface components (e.g., alerts, notification badges, or the like) that indicate one or more resolution reports requiring submission. Also, similar to notification for patients, healthcare service engines may be arranged to be configured to provide notifications or alerts regarding incomplete resolution reports to providers via mobile applications, email, SMS/texts, web/desktop applications (e.g., provider portals), or the like. In some embodiments, visit resolution reports may be structured, saved, shared, or sent to other providers, care teams or provider organizations, as well as being provided to electronic medical records and other systems used by provider organizations.

In one or more of the various embodiments, healthcare service engines may be arranged to provide user interfaces collecting visit resolution information that enable providers to perform various actions, such as, waiving visit fees, recommending or scheduling referrals, scheduling followup visits, providing or confirming prescriptions, or the like. For example, in some embodiments, if the provider determines that a remote visit was not appropriate for the visit/patient, the provider may waive the visit fees because a in-person visit for the same patient may be required.

In one or more of the various embodiments, user interfaces provided collecting information for resolution reports may include an option for the provider to delay or defer providing the information. Accordingly, in some embodiments, if a provider is pulled into an emergency/priority event, they may return later to provide the information for the visit resolution report.

In one or more of the various embodiments, healthcare service engines may be arranged to enable provider organizations to establish policies with regard to the type of information that should be collected for patient satisfaction reports or visit resolution reports. Accordingly, in some embodiments, healthcare service engines may be arranged to employ templates, rules, instructions, validation instructions, default entries, or the like, provided via configuration information to account for local circumstances or local requirements.

In one or more of the various embodiments, healthcare service engines may be arranged to collect various metrics associated with each stage of workflow 500 as well as information associated with the visit as a whole. In some embodiments, this information may include, wait times, duration of visit, resolution information, patient satisfaction information, services rendered (e.g., charged or uncharged actions), supplies consumed, modality information, or the like. Also, in some embodiments, healthcare service engines may be arranged to associate metrics of subsequent visits or subsequent treatment outcomes with past visits.

Further, in some embodiments, healthcare service engines may be arranged to collect various community metrics from servicing multiple provider organizations, Accordingly, in some embodiments, healthcare service engines may be arranged to provide visibility across provider organizations regarding the efficiency of their digital care operations. For example, in some cases, patient satisfaction, wait times, visit durations, issue resolution, or the like may be benchmarked for comparative purposes that enable provider organizations to improve their operations by continuously learning from one and other.

Also, in some embodiments, healthcare services engines may be arranged to enable provider organizations to employ new on-demand or convenient care models within existing services or as new lines of business to expand access to care. For example, in some embodiments, a primary care provider who typically schedule patients weeks or months in advance may be enabled to employ the healthcare service engine to schedule on-demand patient if they are not service other patients or if a scheduled patient has canceled their appointment. Accordingly, in some embodiments, healthcare service engines may further improve visibility across all provider resources so they can be best optimized.

Also, in one or more of the various embodiments, healthcare service engines may be arranged to automatically improve the discoverability of provider availability within provider organizations by continually harvesting real time availability from the EMR and connecting it with digital properties, including online search engines, websites, online marketplaces, mobile apps, communication platforms, or the like that may extend beyond the provider organizations' own website. Accordingly, in some embodiments, healthcare service engines may be arranged to dynamically modify the content and messaging of provider organizations that may be shared on the various digital properties about their availability, to intelligently direct advertisement expenditures and promotional efforts of specific clinics or providers, and to syndicate their availability to these digital properties. In some embodiments, these activities may enable the collection of additional information regarding patient intent and motivation that may be helpful for routing and matching patients to providers.

Figure 6:
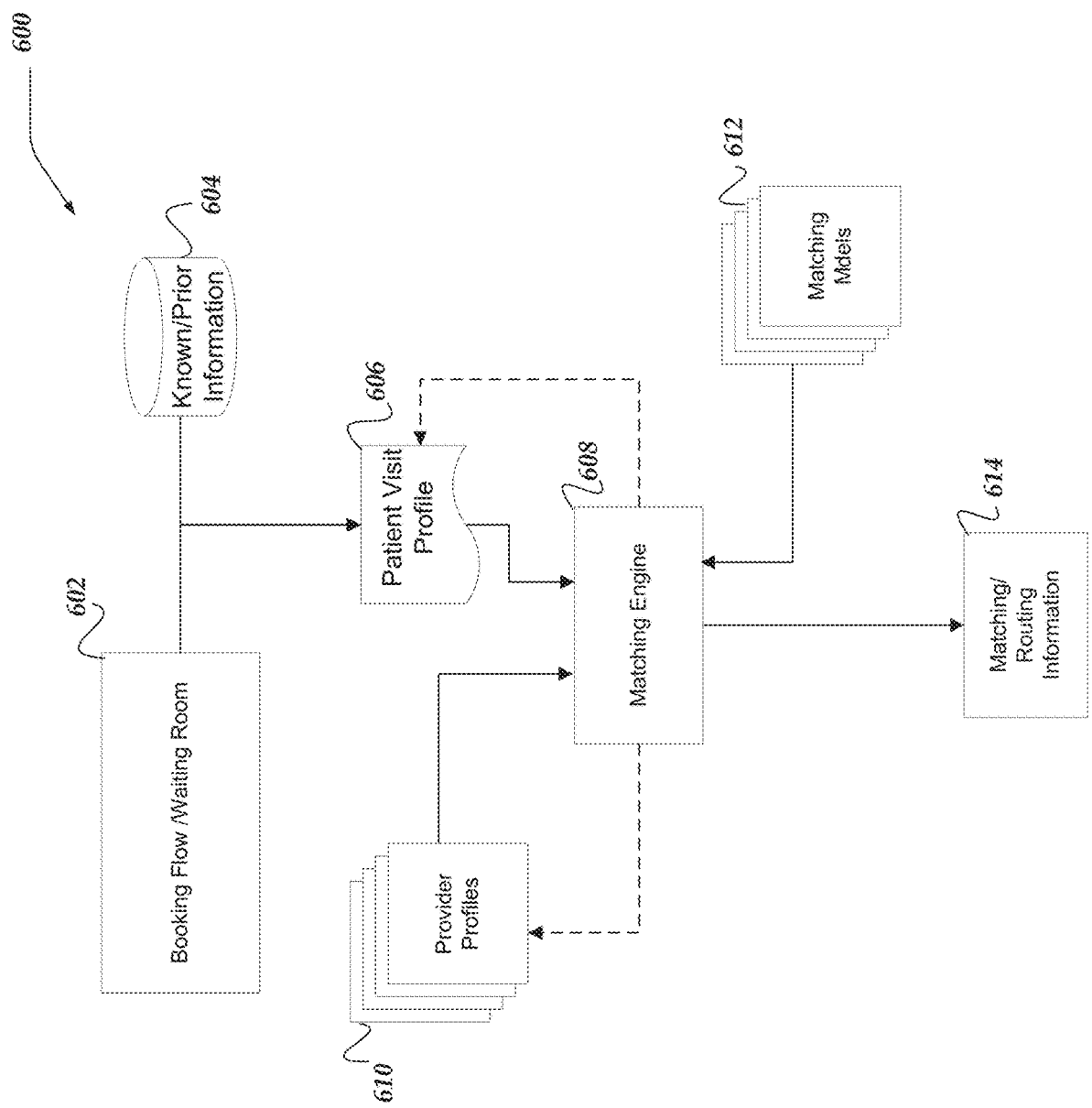
FIG. 6 illustrates a logical schematic of a portion of a healthcare service platform for matching patients with providers in accordance with one or more of the various embodiments.

FIG. 6 illustrates a logical schematic of a portion of healthcare service platform 600 for matching patients with providers in accordance with one or more of the various embodiments. As described above, in some embodiments, healthcare service engines may be arranged to employ one or more rules, machine learning models, or the like, or combination thereof, for matching patients with providers.

In some embodiments, the process that enables patients to request healthcare services from the provider organization may be referred to as the booking flow.

In one or more of the various embodiments, healthcare service platforms, such as, healthcare service platform 600 may be arranged to provide user interfaces that incoming patients may employ to request a visit. In some embodiments, such user interfaces may include one or more user interface forms that enable pertinent information to be collected from the incoming patients.

In one or more of the various embodiments, healthcare service engines may be arranged to employ information collected from booking flow/waiting room user interfaces to generate a patient visit profile, such as, patient visit profile 606. In some embodiments, patient visit profiles may be data structures that collect or store various information about patients that may be collected during a booking flow or via virtual waiting rooms. Further, in some embodiments, healthcare service engines may be arranged to augment patient visit profiles with other information that may be available. In some embodiments, the other information may be provided from various data stores or third-party information services, here represented by known/prior information data store 604.

Accordingly, in some embodiments, healthcare service engines may be arranged to provide patient visit profiles to matching engines. In some embodiments, matching engines may be arranged to match or attempt to match patients to one or more visits or providers based on patient visit profile 606, provider profiles 610, or matching models 612. In this example, matching/routing information 614 represents the output of matching engine 608. For example, for some embodiments, if patient profile 606 is matched with a provider, the matching/routing information may include the identity of the matched provider. In some embodiments, matching information may include matching scores for more than one or more provider such that that matching score corresponds to the quality of the match, as defined by the combination of a) alignment with stated or predicted patient profile information or preferences, such as location, language, ethnicity, gender or other preferences; and b) greatest likelihood of achieving a particular goal such as definitive issue resolution, positive clinical outcome, high patient and provider satisfaction, reduced visit duration, reduced costs, greater efficiency of delivering care in the visit, greater or more balanced provider utilization or other goals.

In some embodiments, healthcare service engines may be arranged to provide one or more user interfaces that lead a patient through a booking flow that may result in an instant/ on-demand virtual/remote visit, a scheduled virtual/remote visit, an on-demand instant in-person visit, a scheduled in-person visit, an asynchronous scheduled virtual/remote visit or the like.

In some embodiments, healthcare service engines may be arranged to automatically match patients with providers. In some cases, for some embodiments, healthcare service engines may be configured to generate match scores for recommended matches. In some embodiments, if match scores meet one or more defined conditions, healthcare service engines may be arranged to automatically assign patients to providers based on the match score. Also, in some embodiments, if match scores fail to meet one or more conditions, healthcare service engines may be arranged to provide a list of recommended providers to patients or provider organization administrators to enable them to select a provider for a visit. Similarly, in some embodiments, healthcare service engines may be configured provide lists of recommended providers sorted based on their corresponding match scores. In some embodiments, match scores may be tuple or vector of one or more values, including a match score, confidence scores, or the like. In some cases, if more than one matching model contributed to a match score, sub-scores associated with each matching model may be include in the match score.

In one or more of the various embodiments, matching engines may be arranged to employ matching models for matching patients/visits with providers. In some embodiments, matching models, such as, matching models 612 may be comprised of heuristics, rules, machine learning models, or the like, that may be employed to generate one or more matching scores. In some embodiments, healthcare service engines may be arranged to enable different matching models to be employed depending on local circumstances or local requirements. For example, in some embodiments, historical data for training machine learning models may be absent for an initial deployment of a healthcare service platform, so during the initial operational period the healthcare service engine may be arranged to rely on matching models based on rules, heuristics, generalized machine learning models, or the like. Then, in some embodiments, if sufficient operational data may be collected to enable specialized machine learning models to be trained based on data/metrics generated locally, healthcare service platforms may be arranged to employ matching models that include trained machine learning models as they become available.

In some cases, different provider organizations may have different matching criteria to support different organizational policies, business models, regulatory requirements, insurance/payor requirements, or the like. Accordingly, in some embodiments, healthcare service engines may be arranged to determine matching models or portions of matching models based on configuration information to account for local circumstances or local requirements.

In one or more of the various embodiments, provider organizations may be enabled to customize the priority and weighting of the rules and algorithms that comprise matching models for determining how patients may be routed and matched to care modalities, settings, or providers. In some embodiments, this may enable provider organizations to achieve their own unique objectives. For example, if one provider organization prioritizes patient satisfaction while another prioritizes cost reduction, they may configure one or more matching models to generate match scores in accordance with those preferences.

In one or more of the various embodiments, healthcare service engines may be arranged to continuously update patient visit profiles as data/metrics about patients, visits, or providers may be provided or determined. For example, as patients go through booking flows, information about the patient or the reason for the visit request may be collected. Thus, as additional information may be collected, patient visit profiles may be updated.

Accordingly, in some embodiments, healthcare service engines may be arranged to submit updated patient visit profiles to matching engines. In some embodiments, matching engines may be arranged to update matching/routing information in accordance with the updated patient visit profiles. For example, while a patient is in a virtual waiting room, additional information may be learned about the reason for the patient visit request via chat, audio, or other supplemental submissions by the patient. Thus, in this example, as updated/additional information is included in the patient visit profile, the matching engine may update its recommendations.

In some cases, for some embodiments, matching engines may cancel a match or assignment to one provider in favor of another provider based on the updated patient visit profile. For example, if the initial visit reason provided by the patient resulted in an initial match with Provider A, additional information collected during a live chat with the patient may provider information that indicates that the patient may be better matched with Provider B.

Further, in some embodiments, healthcare service engines may be arranged to generate provider profiles, such as, provider profiles 610 that may be included as inputs to matching engines. In some embodiments, provider profiles may include one or more real-time metrics related to current utilization of the provider. For example, if the provider associated with an upcoming visit is in another visit that is running long, the matching engine may re-assign the visit/patient to another qualified provider that may be available sooner.

Further, in some embodiments, healthcare service engines may be arranged to include one or more metrics associated with longer term information in provider profiles, such as, experience, specialties, provider preferences, additional/supplemental training certifications, cost/value information, outcome history, visit duration metrics, referral history, visit resolution history, patient satisfaction information, or the like. In some embodiments, provider profiles may be arranged to reference other data stores rather than duplicating information that may be stored or collected elsewhere.

In some embodiments, healthcare service engines may be arranged to update provider profiles in real-time as visits may be requested and patients may be queued. Accordingly, in some embodiments, as circumstances associated with a patient, provider, or visit may change, matching engines may be arranged to modify/update provider assignments or visit scheduling.

Figure 7:
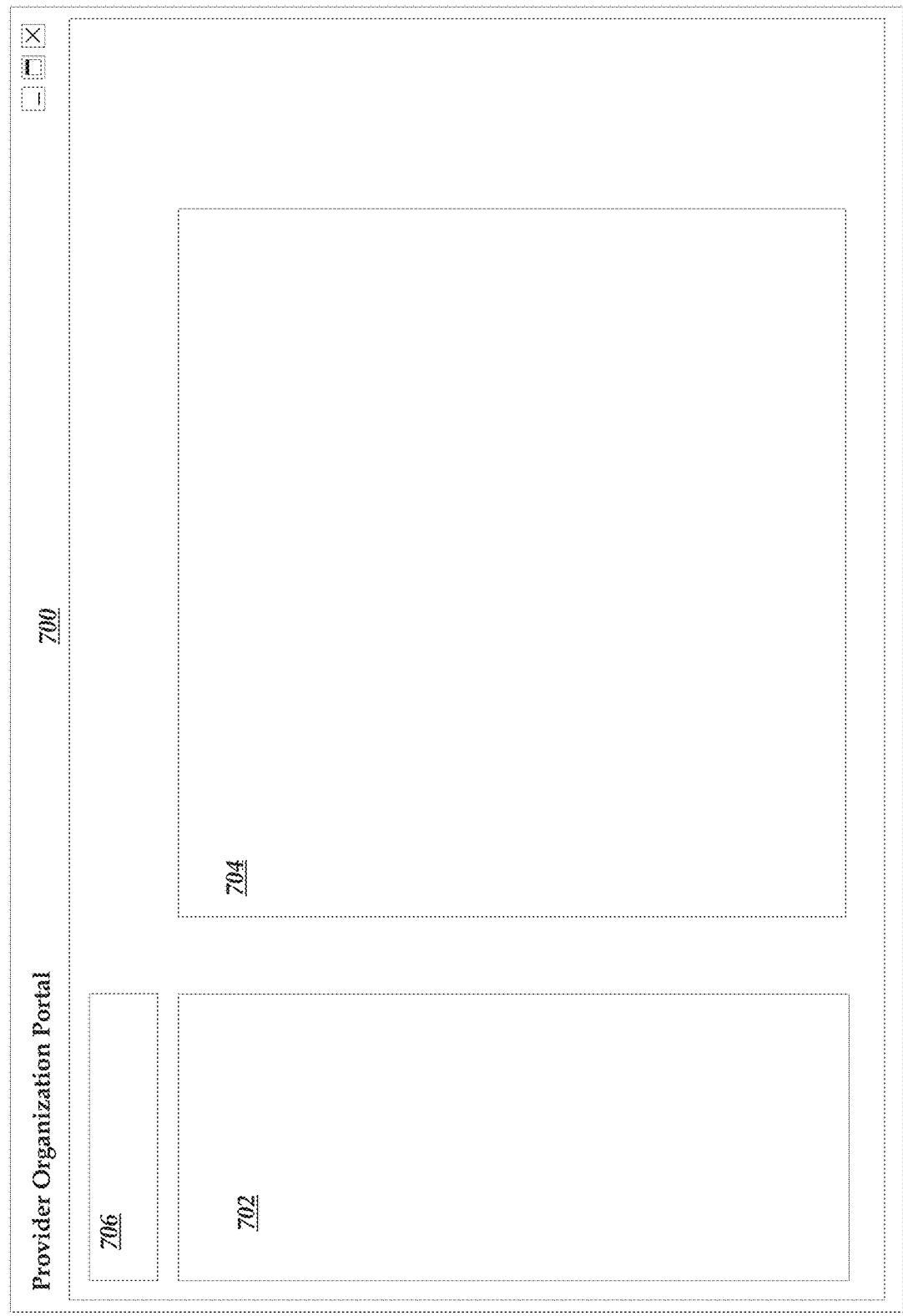
FIG. 7 illustrates a logical representation of a user interface for a provider organization portal for healthcare service platform in accordance with one or more of the various embodiments.

FIG. 7 illustrates a logical representation of user interface 700 for a provider organization portal for healthcare service platform in accordance with one or more of the various embodiments. In one or more of the various embodiments, healthcare service engines may be arranged to generate user interfaces, such as, user interface 700 for presenting comprehensive view of queued patients, pending visits, assigned/available providers, or the like. Accordingly, in some embodiments, healthcare service engines may be arranged to provide provider organization administrator a single view that shows patients that may be waiting for visits to occur, providers currently conducting visits, providers available to be assigned to visits, or the like.

In some embodiments, display panel 702 may represent a user interface that lists queued patients, patients in visits, patients in the booking flow, and so on. In some embodiments, healthcare service engines may be arranged to sort the patients based on one or more conditions or criteria. In some embodiments, sorting criteria may be based on the length time a patient is waiting for a visit, type of visit, new information determined via interactions in a virtual waiting room, or the like.

Similarly, in some embodiments, display panel 704 may be arranged to display a sorted list of providers. In some embodiments, providers may be sorted based on various criteria, including, availability, over-length visit time, visit type, number of assigned/schedule visits, or the like.

In some embodiments, display panels for showing sorted lists may include one or more user interface controls to enable users to interactively select sorting criteria, or the like.

Further, in some embodiments, healthcare service engines may be arranged to provide user interfaces that include display panel 706 for providing user interface controls for additional filters, or the like. For example, in some embodiments, a display panel, such as, display panel 706 may be configured display controls for selecting or limiting geographical ranges, time/day ranges, visit types, patient types, or the like.

Also, in one or more of the various embodiments, healthcare service engines may be arranged to provide user interfaces for provider portals that may include one or more display panels some of which may be similar to display panels included in provider organization portal. However, in some embodiments, provider portals may be automatically filtered to shown information for one provider that may be logged into the provider portal. Accordingly, in some embodiments, providers may be enabled to view which patients may be queued for visits. Likewise, in some embodiments, if a provider is preparing to conduct a visit with a patient, the provider may access patient or visit details using their provider portal.

In some embodiments, users or provider organization portals or provider portals may be enabled to visit detail views of the queued patients, providers, visit information, or the like. In some embodiments, healthcare service engines may be arranged to provider user interfaces that enable users to access virtual waiting room user interfaces. Accordingly, in some embodiments, providers may observe or review interactions or metrics that may have been collected for the patient in the virtual waiting room. In some embodiments, healthcare service engines may be arranged to enable providers or their representatives to interact with patients while they are in the virtual waiting room. For example, a provider may request clarification or more information from a patient based on a review of the reasons for the visit.

One of ordinary skill in the art will appreciate that user interfaces for healthcare service platforms may include more or fewer display panels than shown here. Accordingly, for brevity and clarity user interface 700 is illustrated as having the three panels shown. However, one of ordinary skill in the art will appreciate that user interface 700 as illustrated is at least sufficient for disclosing these innovations.

Figure 8:
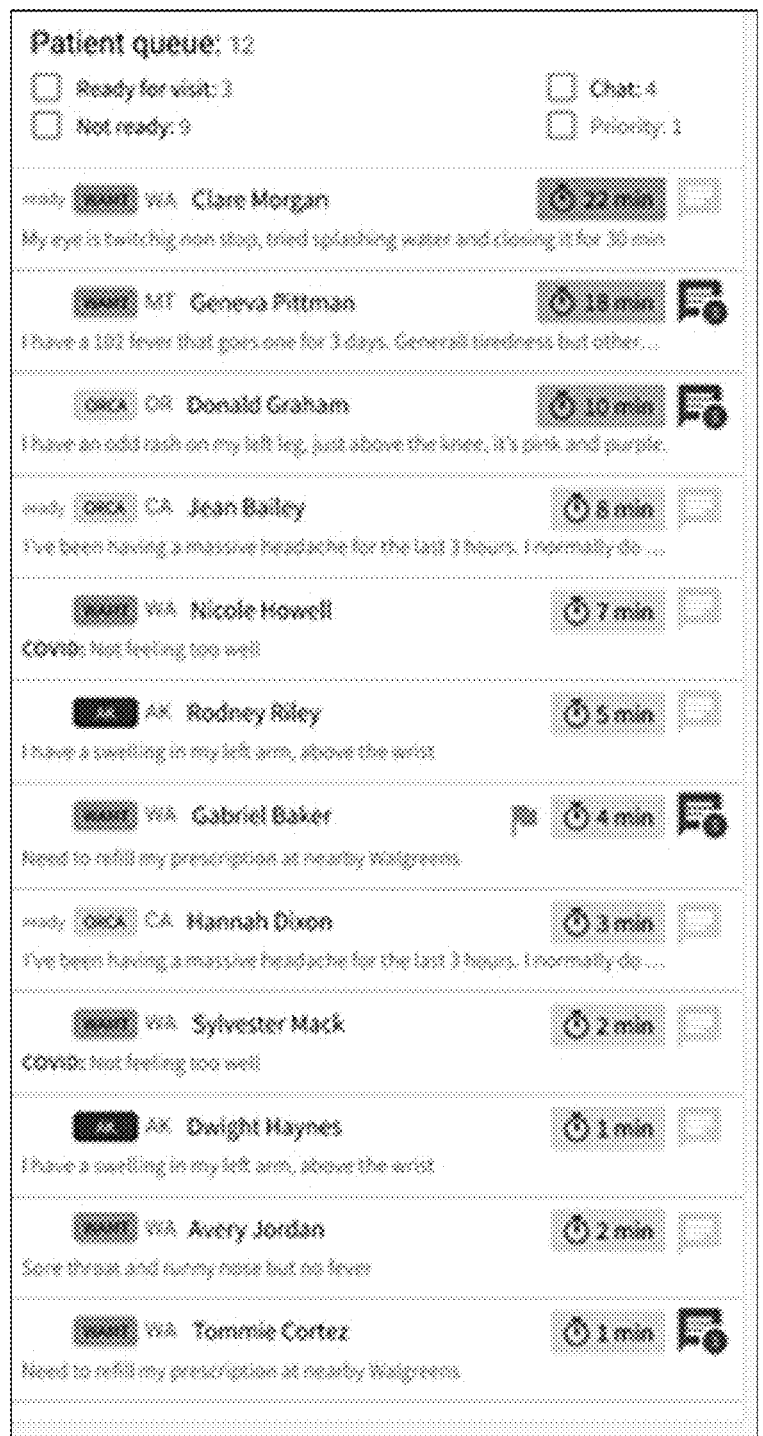
FIG. 8 illustrates a representation of a display panel for providing user interfaces for healthcare service platforms in accordance with one or more of the various embodiments.

FIG. 8 illustrates a representation of display panel 800 for providing user interfaces for healthcare service platforms in accordance with one or more of the various embodiments. As described above, in some embodiments, user interfaces provided by healthcare service engines may include one or more display panels, such as, display panel 800 for displaying patients that may be queued for visits. In this example, display panel 800 may be considered to represent a patient display panel for a provider organization portal. Accordingly, in some embodiments, display panel 800 includes a list of records that correspond to patients that may be queued for visits.

In some embodiments, each record may include information, such as, patient name, patient location, status information, queue/waiting time, reason for visit, or the like. Note, in some embodiments, the representation of the information in each record may vary in terms of style, order, or the like, among provider organizations. In some embodiments, one or more portions of the information of a record may be color coded to represent various conditions or circumstances. For example, patients that have a wait time that exceeds a threshold value may be indicated using different colored wait-times that patients that have recently joined the visit queue.

Note, in this example (FIG. 8), the details of each record may be difficult to discern. However, at least for clarity it is useful to illustrate how to display multiple records at the expense of showing the detail of any one record. A detailed example of a record may be found below.

Figure 9:
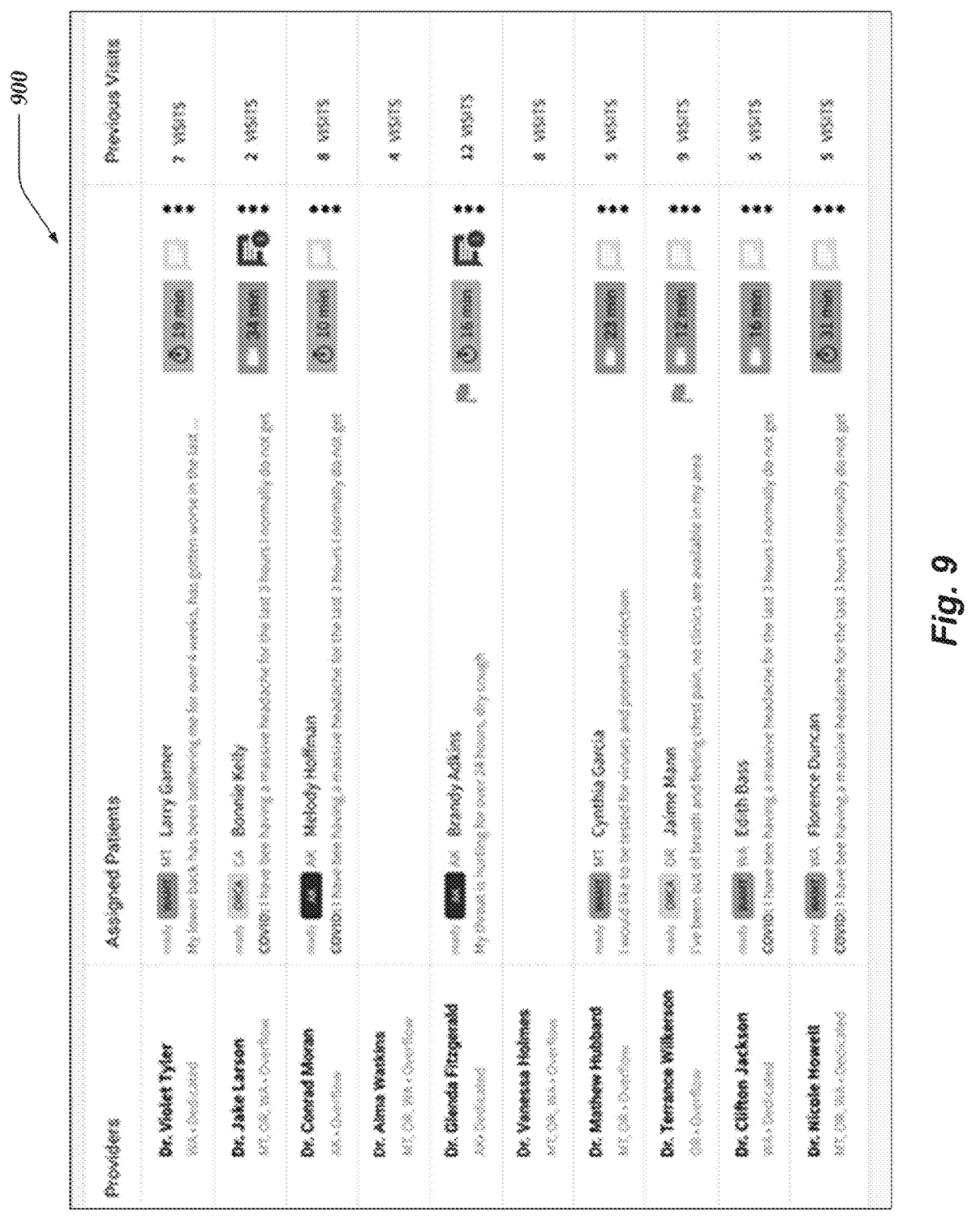

FIG. 9 illustrates a representation of display panel 900 for providing user interfaces for healthcare service platforms in accordance with one or more of the various embodiments. As described above, in some embodiments, user interfaces provided by healthcare service engines may include one or more display panels, such as, display panel 900 for displaying provider information that may be associated with a provider organization. In this example, display panel 900 may be considered to represent a provider display panel for a provider organization portal. Accordingly, in some embodiments, display panel 900 includes a list of records that correspond to providers that may be associated with a provider.

Similar to queued patients lists described above, provider display panels may include one or more records that each may include, provider name, assigned patients, in/out visit status, available/unavailable status, duration of current visit (if conducting a visit), or the like.

In some embodiments, provider records may be sorted based on one or more factors, including availability, status, utilization, match preferences, or the like.

Note, in this example (FIG. 9), the details of each record may be difficult to discern. However, at least for clarity it is useful to illustrate how to display multiple records at the expense of showing the detail of any one record. A detailed example of a record may be found below.

Figure 10:
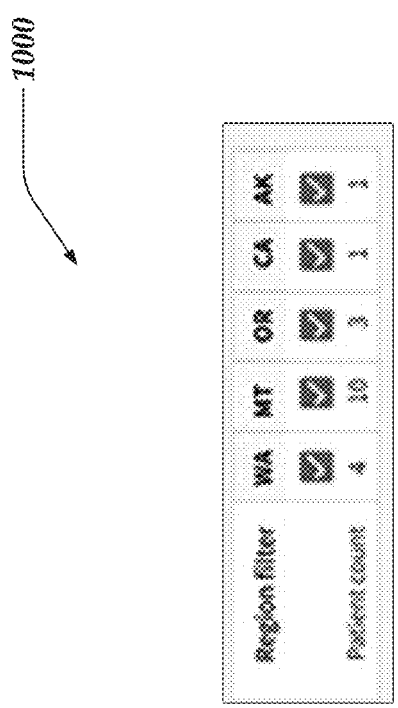
FIG. 10 illustrates an example of a display panel for providing user interfaces for healthcare service platform in accordance with one or more of the various embodiments.

FIG. 10 illustrates an example of display panel 1000 for providing user interfaces for healthcare service platform in accordance with one or more of the various embodiments. As described in the description for user interface 700, healthcare service engines may be arranged to display panels, such as, display panel 1000 for providing interactive controls that enable users to apply, filters associated with data ranges, geographic regions, or the like.

For example, in some embodiments, provider organizations may have clinics or other care facilities spread across a wide geographic area. Accordingly, in some embodiments, a display panel, such as display panel 1000 may enable users of provider organization portals to set one or more filter conditions. In this example, display panel 1000 may be limited to geographic region filtering, however, one of ordinary skill in the art will appreciate that other filters based on other characteristics or features of patients, providers, visits, or the like, may be provided. Accordingly, in some embodiments, healthcare service engines may be arranged to employ templates, stylesheets, rules, instructions, or the like, provided via configuration information to account for local circumstances or local requirements in the various user interfaces provided for healthcare service platforms.

In this example, display panel 1000 represents inclusive filters that would enable records associated with the 'checked' geographic regions to be included in a result set for display or inclusion in one or more reports.

Figure 11:
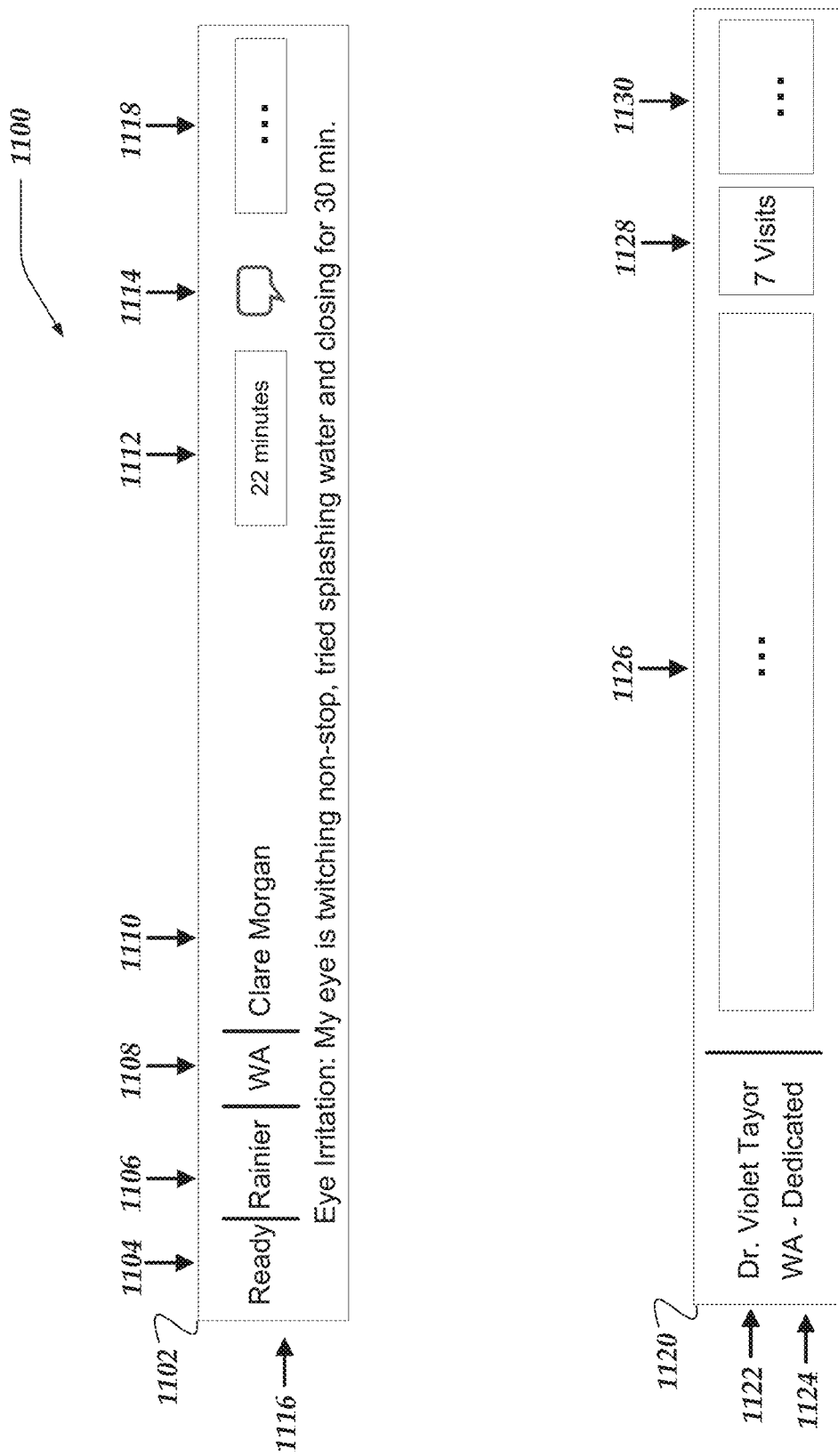
FIG. 11 illustrates logical schematic of portions of a user interface for display queued patient records or provider records in accordance with one or more of the various embodiments.

FIG. 11 illustrates logical schematic of portions of user interface 1100 for display queued patient records or provider records in accordance with one or more of the various embodiments.

As described above, healthcare service engines may be arranged to provide user interfaces such as provider organization portals, provider portals, or the like, that may display records for patients queued for visits, available/unavailable providers, or the like.

In this example, for some embodiments, record 1102 represents a user interface that may be employed to display patient records. In this example, for some embodiments, record 1102 may display various fields, including status field 1104, clinic location field 1106, geographic region field 1108, patient name field 1110, current wait time field 1112, chat active/available field 1114, reason for visit field 1116, additional fields 1118, or the like.

Similarly, for example, for some embodiments, record 1120 may represent a user interface for displaying provider records. Accordingly, in this example, record 1120 may display various fields associated with a provider, including, provider name field 1122, provider location/status field 1124, assigned patient/visit information field 1126, number of visits for patient field 1128, additional fields 1130, or the like.

In some embodiments, the set of fields included in records such as, record 1102 or record 1120 may vary depending on local circumstances or local requirements. Accordingly, in some embodiments, healthcare service engines may be arranged to determine the fields to include in records based on one or more templates, rules, stylesheets, or the like, provided by configuration information to account for local circumstances or local requirements. Likewise, in some embodiments, healthcare service engines may be arranged to determine to order of fields or other styling of records based on templates, rules, stylesheets, or the like, provided by configuration information to account for local circumstances or local requirements.

In some embodiments, status fields, such as, status field 1104 may be employed to indicate if a patient is ready for a visit to commence. In some embodiments, for remove/virtual visit this may indicate that the patient has provided sufficient information for the visit as well as successfully completed a technology system check. In some cases, if the status indicates that the patient is not ready, users may be enabled to interact (e.g., hover, click, or the like) to reveal one or more reasons that may cause the patient to be considered not ready.

In some embodiments, location fields, such as, location field 1106 may be employed to indicate which clinic the patient may be associated with. In some case, provider organizations may register patients with a specific clinic/care location to act as the patient's 'home' location. In some embodiments, the location field may represent a patient's preference for particular location. Alternatively, in some embodiments, the location field may show the clinic that may be closest to the patient. In some embodiments, client location fields may be color coded to enable rapid confirmation of location information.

In some embodiments, geographic location fields, such as, geographic location field 1108 may include a physical region (e.g., city, state, or the like) where the patient may be located. In some embodiments, geographic location fields may be color coded to enable rapid confirmation of location information.

In some embodiments, patient name fields, such as, patient name field 1110 may identify the patient that may be queued for a visit. In some embodiments, patient name fields may be color code to indicate age cohorts, priority, or the like.

In some embodiments, wait time fields, such as, wait time field 1112 may be arranged to show a running timer/clock that indicates how a long a patient has been waiting in a waiting room. In some embodiments, wait time field may be color coded to indicate priority such that if a wait time exceeds a threshold value its color may be changed to indicate that there has been some delay. Also, in some embodiments, color coding or other styling may be employed to indicate if the patient is waiting for an in-person visit or a virtual visit.

In some embodiments, chat fields, such as, chat field 1114 may be employed to indicate if a patient has submitted chat or other feedback/interactions that may need to be responded to. In some embodiments, a user may interact with the chat field to open a virtual waiting room or other user interface that may enable the user to respond/react to the patient's communications/actions.

In one or more of the various embodiments, reason for visit fields, such as, reason for visit field 1116 may employ to capture a patient's description for the reason for the visit. In some embodiments, this field may be intended to capture free-text/free-form comments from the patient regarding the reason for their visit. In some embodiments, one or more portions of the information included in a reason field may be provided from picklists/defaults, or the like, with a remainder of the information provided free-form by the patient. In this example, field 1116 includes two portions, the first of which (Eye Irritation) may be used to grossly categorize the reason for visit while the remainder (My eye . . . ) may represent information entered by a patient.

In some embodiments, additional fields, such as, additional field 1118 represent one or more additional fields that may be included to account for local circumstances or local requirements. In some embodiments, various provider organizations may require records to include one or more field unique to their practice or operations. Accordingly, in some embodiments, healthcare service engines may be arranged to employ templates, or the like, associated with instructions (e.g., queries, API calls, or the like) that obtain the information for display in the additional field. Also, in some embodiments, healthcare service engines may be arranged to provide one or more optional interactive fields that provider organizations may decide to include in records, such as, opening calendars, navigating to other user interfaces, contacting supervisors, raising alarms, or the like.

In some embodiments, provider name fields, such as, provider name field 1122 may be employed to display the name of a provider. In some embodiments, for some cases, the provider may be a business or other organization rather than an individual person. In those cases, the provider name field may show a business name rather than a person's name.

provider location/status field 1124, assigned patient/visit information field 1126, number of visits for patient field 1128, additional fields 1130, or the like.

In some embodiments, provider location/status fields, such as, provider location/status field 1124 may be employed to display information associated with the jurisdiction the provider may be licensed to operate in. In some embodiments, the provider location may represent a region that the provider organization has assigned a provider. Further, in some cases, a provider location field may indicate the physical location of the provider. Likewise, in some cases, the provider location field may represent the location of the clinic that the provider may be assigned to.

Also, in some embodiments, provider status fields may include information related to the provider's professional relationship with the provider organization. In other cases, a provider status field may indicate if the provider may be dedicated to a particular practice/treatment area, line of business, or the like. In some embodiments, records, such as, record 1120 may include more than one provider status field each indicating different status information for the provider.

In some embodiments, assigned patient fields, such as, assigned patient field 1126 may be considered to include that may be similar or the same as the information included in record 1102. In some cases, if the provider is unassigned, field 1126 may indicate that the provider may be available.

In some embodiments, visit information fields, such as, visit information field 1128 may be employed to show additional information about the assigned patient or the visit. In this example, field 1128 indicates that this is the 7th visit the provider has conducted this shift.

In one or more of the various embodiments, one or more additional fields, such as, additional field 1130 may be considered similar to field 1118 in that provider organization may be enabled to configured additional field to be included in provider/visit records.

One of ordinary skill in the art will appreciate that user interfaces for healthcare service platforms may include more or fewer record types with fields that may be the same or different than shown here. In some embodiments, healthcare service engines may be arranged to employ templates, rules, instructions, or the like, provided via configuration information to determine the included fields or field order for records, such as, record 1102, record 1120, or the like.

Figure 12:
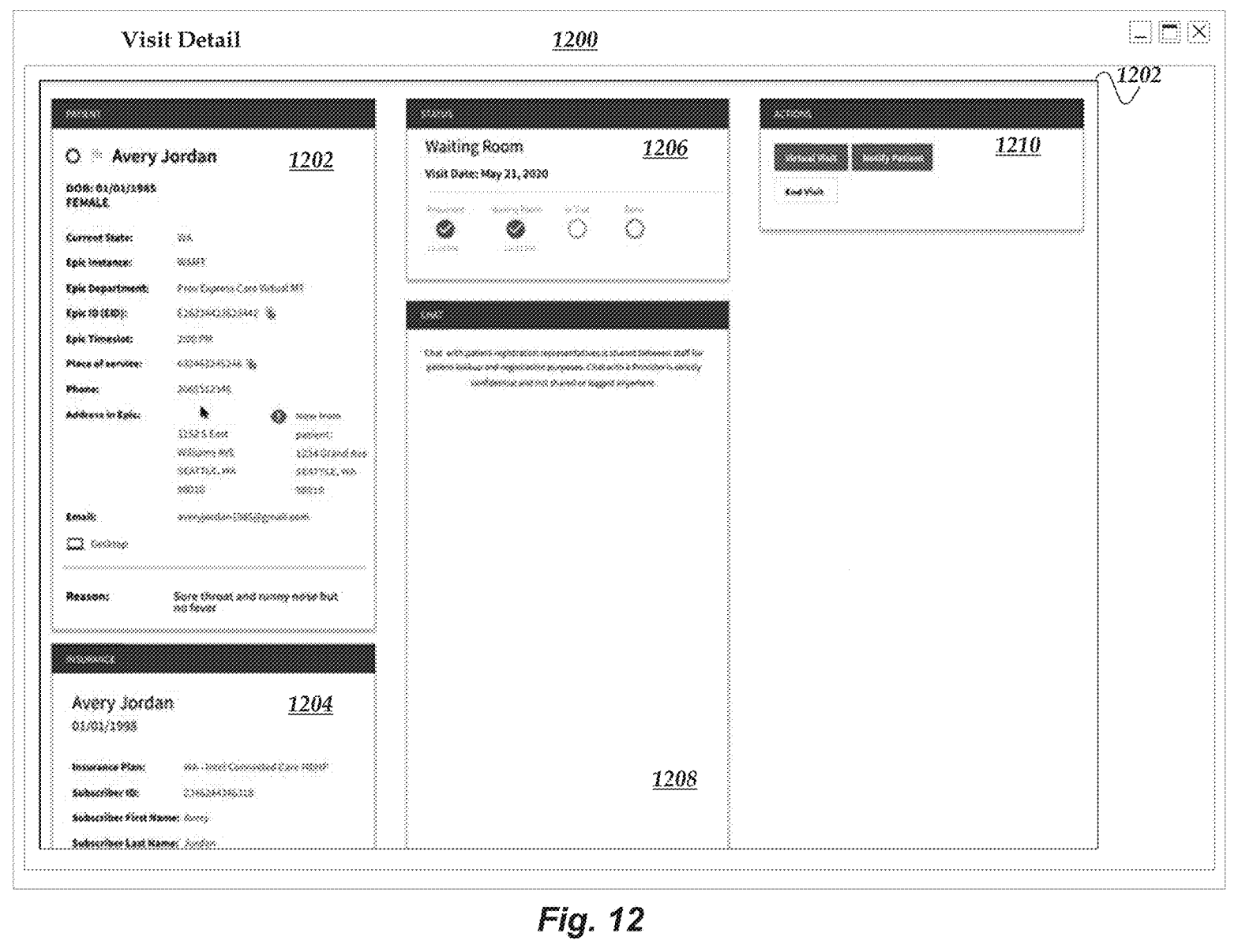

FIG. 12 illustrates a logical representation of user interface 1200 for providing visit detail user interfaces for healthcare service platforms in accordance with one or more of the various embodiments.

In one or more of the various embodiments, healthcare service engines may be arranged to provide one or more user interfaces, such as, user interface 1200 that enable users (e.g., providers, provider organization representatives, or the like) to view details that may be associated with queued or pending patient visits. In some embodiments, visit detail user interfaces may be arranged to include various display panels that may be determined to be useful for various activities, including, reviewing patient provided information, interacting with patients (e.g., chat), canceling or rescheduling visits, or the like.

In this example, for some embodiments, display panel 1202 may be arranged to show general patient information, including, demographic information, sociographic information, address information, or the like. In some embodiments, display panels may be arranged to highlight one or more discrepancies between information provided by the patient and one or more other patient records. For example, if the mailing address provided by patient is different than a mailing address stored in another data store, this may be highlighted/emphasized in the user interface to bring it to the attention of a user. Similarly, in this example, for some embodiments, display panel 1204 may include insurance information for the patient.

Also, in this example, for some embodiments, display panel 1206 may display visit information, display panel 1208 may enable users to chat with patients or view previous chat that may have occurred. For example, if the patient engaged in a chat with a medical assistant before the primary provider conducts the visit, the prior chat history may be shown in a display panel such as display panel 1208.

Also, in this example, for some embodiments, one or more display panels, such as, display panel 1210 may enable users to execute one or more actions. In some embodiments, healthcare service engines may be arranged to dynamically display/enable actions depending on the patient, the visit reason, the user, or the like. In some embodiments, healthcare service engines may be arranged to employ one or more models similar to (or part of) matching models described above to determine if action controls should be enabled in display panel 1210.

Further, in some embodiments, healthcare service engines may be arranged to determine the one or more display panels to display in user interfaces, such as, user interface 1200 based on templates, rules, instructions, or the like, provided via configuration information to account for local circumstances or local requirements. Also, in some embodiments, healthcare service engines may be arranged to employ one or more models similar to or included in matching models to dynamically determine the display panel for display in a visit detail user interface. Likewise, in some embodiments, healthcare service engines may be arranged to dynamically determine the positioning of the various display panels based on configuration information, models, or the like, or combination thereof.

Figure 13:
FIG. 13 illustrates a logical representation of a user interface representing a portion of a booking flow for healthcare service platforms in accordance with one or more of the various embodiments.
Figure 13:

FIG. 13 illustrates a logical representation of user interface 1300 representing a portion of a booking flow for healthcare service platforms in accordance with one or more of the various embodiments. As described above, healthcare service engines may be arranged to provide one or more user interfaces that walk/guide patients through a booking flow. Accordingly, user interface 1300 represents an example of one of the user interfaces that may be employed as part of a booking flow. In this example, a patient may be offered to choose between in-person or virtual visits. In some embodiments, healthcare service engines may be configured to automatically guide or encourage patients to conform to one or more care settings or modalities that align with their interests and needs as well as the business/operation policies of the provider organization.

In this example, the prices of the different types of visits are shown to ensure that the patient realizes that (in this example) virtual visits may be less expensive than in-person visits. In some cases, healthcare service engines may be configured to include or omit information, options, or the like, based on provider organization preferences or policies.

Generalized Operations

FIGS. 14-20 represent generalized operations for healthcare service platform in accordance with one or more of the various embodiments. In one or more of the various embodiments, processes 1400, 1500, 1600, 1700, 1800, 1900, and 2000 described in conjunction with FIGS. 14-20 may be implemented by or executed by one or more processors on a single network computer, such as network computer 300 of FIG. 3. In other embodiments, these processes, or portions thereof, may be implemented by or executed on a plurality of network computers, such as network computer 300 of FIG. 3. In yet other embodiments, these processes, or portions thereof, may be implemented by or executed on one or more virtualized computers, such as, those in a cloud-based or containerized environment. However, embodiments are not so limited and various combinations of network computers, client computers, or the like may be utilized. Further, in one or more of the various embodiments, the processes described in conjunction with FIGS. 14-20 may be used for healthcare service platforms in accordance with at least one of the various embodiments or architectures such as those described in conjunction with FIGS. 4-13. Further, in one or more of the various embodiments, some or all of the actions performed by processes 1400, 1500, 1600, 1700, 1800, 1900, and 2000 may be executed in part by healthcare service engine 322, matching engine 324, or the like, running on one or more processors of one or more network computers.

Figure 14:
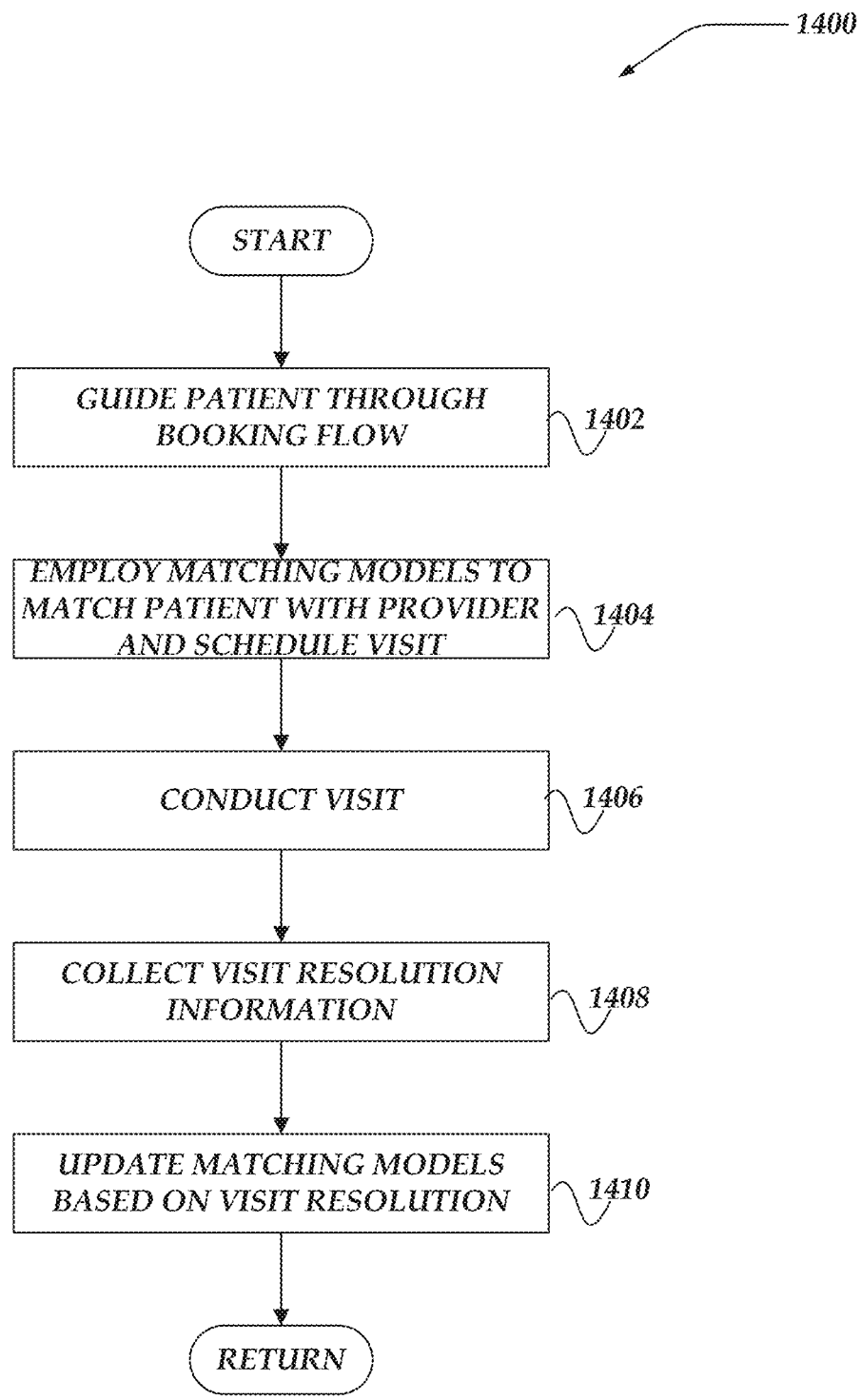
FIG. 14 illustrates an overview flowchart of a process for healthcare service platform in accordance with one or more of the various embodiments.

FIG. 14 illustrates an overview flowchart of process 1400 for healthcare service platform in accordance with one or more of the various embodiments. After a start block, at block 1402, in one or more of the various embodiments, healthcare service engines may be arranged to guide patients through a booking flow.

In one or more of the various embodiments, as described above, and in more detail below, healthcare service engines may provide a sequence of user interfaces that enable patients to provide information that may be collected in a patient visit profile.

At block 1404, in one or more of the various embodiments, healthcare service engines may be arranged to match patients with providers and schedule visits.

As described above, and in more detail below, healthcare service engines may be arranged to employ matching models to generate match scores that may be used to determine or recommend providers to a visit at a scheduled time.

At block 1406, in one or more of the various embodiments, healthcare service engines may be arranged to conduct visits with patients. In one or more of the various embodiments, healthcare service engines may be arranged to provide one or more user interfaces that facilitate virtual visits or in-person visits between a patients and providers.

In one or more of the various embodiments, healthcare service engines may be arranged to provide provider organizations user interfaces that enable provider organization representatives monitor or interact patients queued for virtual visits.

Also, in some embodiments, healthcare service engine may be arranged to collect a variety of metrics associated virtual visits, including, visit duration, modality/technology, level of interaction, other telemetry, or the like, that may be employed to subsequently evaluate the efficacy of a given visit or types of visits.

At block 1408, in one or more of the various embodiments, healthcare service engines may be arranged to collect visit resolution information, including referrals and subsequent visits, from the conducted visits. In one or more of the various embodiments, healthcare service engines may be arranged to one or more user interfaces to collect patient satisfaction information, provider resolution information, or the like.

At block 1410, in one or more of the various embodiments, healthcare service engines may be arranged to update one or more matching models based on visit resolution information.

In one or more of the various embodiments, healthcare service engines may be arranged to matching models to select or recommend providers, locations, visit types, or the like. Accordingly, in some embodiments, as information or metrics associated with past visits may be collected, one or more matching models may be modified (e.g., re-trained, tuned, discarded, or the like) based on the results of the past visits.

Next, in one or more of the various embodiments, control may be returned to a calling process.

Figure 15:
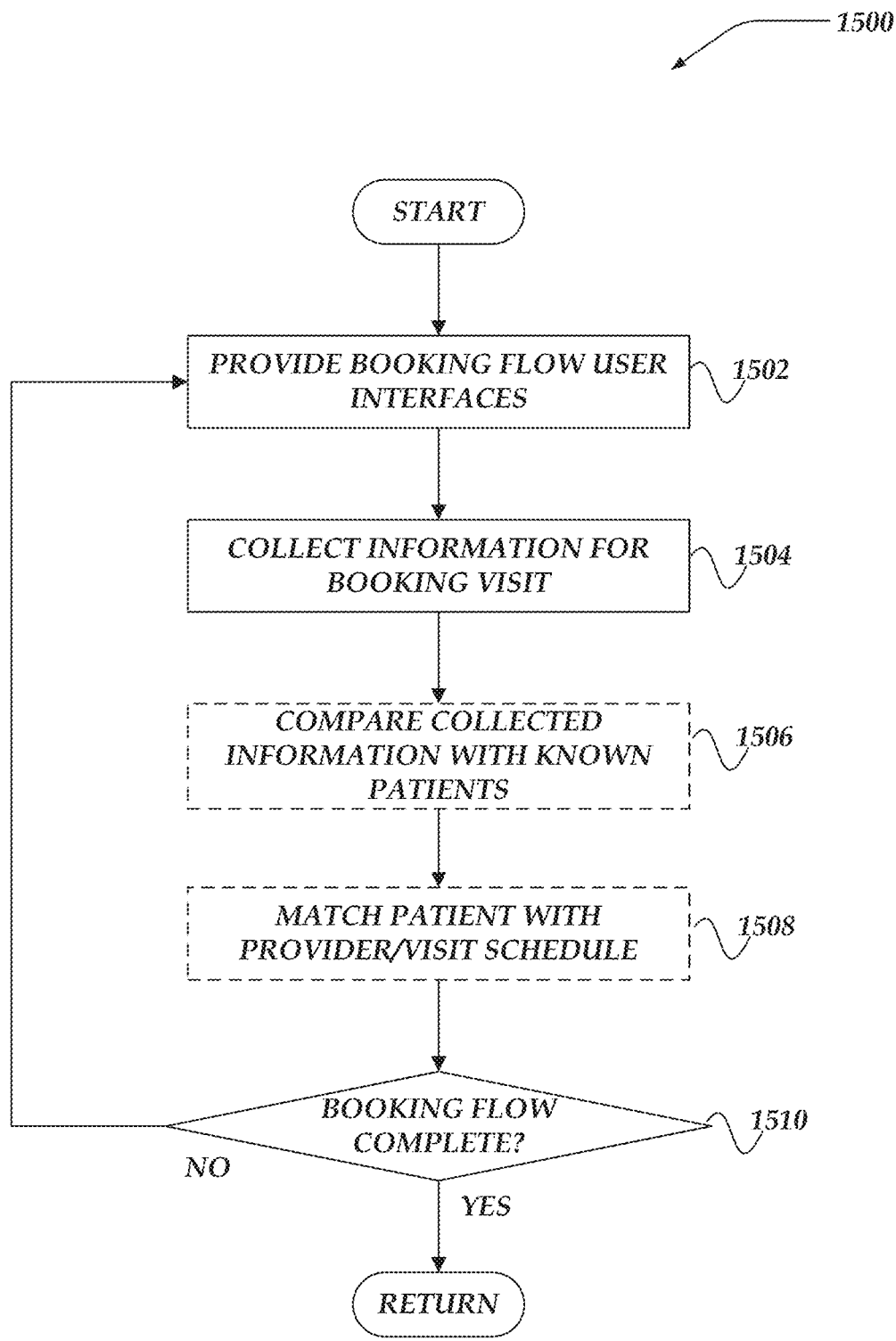
FIG. 15 illustrates a flowchart of a process for healthcare service platform in accordance with one or more of the various embodiments.

FIG. 15 illustrates a flowchart of process 1500 for healthcare service platform in accordance with one or more of the various embodiments. After a start block, at block 1502, in one or more of the various embodiments, healthcare service engines may be arranged to provide one or more booking flow user interfaces to patients. As described above, in some embodiments, healthcare service engines may be arranged to provide a sequence of user interfaces that may be configured to interactively collect information from the patient in preparation for a visit.

In one or more of the various embodiments, healthcare service engines may be arranged to present the user interfaces to patients via a variety of applications, including mobile applications, websites, web-based applications, desktop applications, or the like.

In some embodiments, healthcare service engines may be arranged to store partial or incomplete booking flow information as patients work through the booking process. Accordingly, in one or more of the various embodiments, healthcare service engines may be arranged to enable patients to begin a booking process on one application and then continue or complete the booking process on one or more other applications. For example, in some embodiments, if a patient begins a booking flow using a healthcare service platform client application on their mobile phone, they may be enabled pick up the same booking flow on a desktop application or website hosted application.

In one or more of the various embodiments, healthcare service engines may be arranged to enable provider organizations to customize individual user interfaces as well as customize which user interfaces may be presented during booking flows. Likewise, in some embodiments, healthcare service engines may be arranged to enable provider organizations to configure which entries may be optional or required. Also, in some embodiments, provider organizations may be enabled to configure validation rules for specific or particular fields or entries.

For example, for some embodiments, one provider organization may require some information collected in booking flow that others provider organizations may consider optional or eligible for later collection. Accordingly, in some embodiments, healthcare service engines may be arranged to employ templates, validation rules, or the like, provided via configuration information that enable provider organizations to customize booking flows to account for local circumstances or local requirements.

In one or more of the various embodiments, healthcare service engines may be arranged to dynamically select user interfaces to present in the booking flow based on previously provided information. In some embodiments, booking flows may be configured to branch in different 'directions' depending on patient information collected. For example, portions of a booking for a patient seeking an emergency visit for a non-life-threatening injury may be different than patients scheduling an annual physical, or the like.

Also, in some embodiments, booking flows may vary depending on the information that may be known about the patient. In some embodiments, as patients work through a booking flow, healthcare service engines may be arranged to look up data from patient data stores, EMR services, or the like, that may provide additional context that can drive the direction of the booking flow.

At block 1504, in one or more of the various embodiments, healthcare service engines may be arranged to collect information for booking the visit.

In some embodiments, information may be collected using various user interface controls, such as, text fields, selection/picklists, check boxes, radio buttons, or the like. In some embodiments, the particular control may vary across provider organizations based on local preferences or customization. For example, in some embodiments, for the same type of information, one provider may customize their booking flow user interface to use check boxes user interface controls while another provider organization may customize their booking flow interface to us a drop-down list. Likewise, in some embodiments, healthcare service platforms may be arranged to enable patients to set user interface preferences that may be applied to booking flows. For example, some patients may require different accessibility features than others which may determine how one or more booking flows collect user information.

In one or more of the various embodiments, healthcare service engines may be arranged to generate a patient visit profile that may be comprised of data structures for storing the information collected or inferred during the booking flows. Accordingly, in some embodiments, as new information may be collected, the patient visit profile may be updated.

In one or more of the various embodiments, healthcare service engines may be arranged to associate the collected information with either a permanent patient identifier or a temporary patient identifier. Accordingly, in some embodiments, new or unrecognized patients may be enabled to create incomplete booking flows that they may return to complete at a later time.

At block 1506, in one or more of the various embodiments, optionally, healthcare service engines may be arranged to compare collected information with known patient information.

In one or more of the various embodiments, as information may be collected during the booking flow, healthcare service engines may be arranged to automatically attempt to identify the patient based on known information that may be held in provider organization records, or the like.

In some embodiments, healthcare service engines may be arranged to ask if a patient is a returning patient or new patient. Accordingly, in some embodiments, if a patient is a returning patient, booking flows may collect patient identifiers, such as, patient numbers, birth date, telephone number, usernames, or the like, for returning patients.

Also, in some embodiments, healthcare service engines may be arranged to attempt to infer if patient may be a returning patient based on information collected during a booking flow.

In some embodiments, healthcare service engines may be arranged to execute one or more challenge-response actions to confirm if a patient in a booking flow is a returning patient.

In some embodiments, patients may not indicate that they are returning patient. However, in some embodiments, if a healthcare service engine infers that the patient is a returning patient, the healthcare service engine may indicate to the provider organization representatives that the patient may be a returning patient while not sharing any additional to the patient. Accordingly, in some embodiments, sensitive or personal patient information will not be inadvertently shared with the booking patient until the patient may be confirmed to be a returning patient.

In one or more of the various embodiments, healthcare service engines may be arranged to determine discrepancies between "known" returning patient information and information supplied during the booking floe. For example, if the booking patient provides a different mailing address or insurance information, healthcare service engines may be arranged to provider user interfaces to the provider organization representatives that highlight the discrepancies enabling them to resolve the discrepancies with the patient.

Note, this block is indicated as being optional because in some cases for some embodiments, healthcare service engines may not have access to information of known patients.

At block 1508, in one or more of the various embodiments, optionally, healthcare service engines may be arranged to match patients with providers to schedule a visit.

In one or more of the various embodiments, healthcare service engines may be arranged to employ matching engines to evaluate the information collected or inferred during a booking flow to schedule a visit for a patient. In some embodiments, in some cases, scheduling a visit may include automatically assigning a provider for the visit. Alternatively, in some embodiments, the visit may be automatically scheduled by the healthcare service engine while the provider organization may select/assign a provider to the visit.

In one or more of the various embodiments, healthcare service engines may be arranged to enable provider organizations to configure the level of automation for scheduling or provider assignment based on various features of the visit. In some embodiments, healthcare service engines may be arranged to recommend one or more visit times or provider assignments that a patient or provider organization may select from.

Likewise, in some embodiments, healthcare service engines may be arranged to enable patients to request visit times or request providers that provider organizations or providers may be enabled to confirm, modify, or reject upon review.

Note, this block is indicated as being optional because in some circumstances healthcare service engines may be unable to schedule visits for a patient depending on various circumstances that may arise.

At decision block 1510, in one or more of the various embodiments, if the book flow may be complete, control may be returned to a calling process; otherwise, control may loop back to block 1502.

In one or more of the various embodiments, healthcare service engines may be configured to establish one or more conditions that indicate that the booking flow may be complete. In some embodiments, healthcare service engines may be configured to consider a booking flow complete even though important information may be missing from the patient visit profiles. Accordingly, in some embodiments, healthcare service engines may be arranged to flag the patient visit profile to indicate there may be missing information.

In some embodiments, healthcare service engines may be configured to notify a provider organization representative that a patient may attempting to submit an incomplete booking flow. Accordingly, in one or more of the various embodiments, the provider organization representative may be enabled to intervene in the booking flow via chat, voice, telephone, or the like, to provide an immediate resolution to the incomplete booking flow. For example, if patient may be having difficulty supplying required information, a provider organization representative may initiate an online chat session to resolve the difficulty.

Also, in some embodiments, healthcare service engines may be configured to allow patients to submit incomplete booking information. Accordingly, in some embodiments, healthcare service engines enable patients to partially complete the patient visit profile rather than encouraging patients to completely back-out of the booking process if they encounter problems. Thus, in some embodiments, healthcare service engines may be arranged to notify one or more provider organization representatives that an incomplete/insufficient patient visit profile has been provided so they may take steps to contact the patient to collect the missing information.

Accordingly, in some embodiments, healthcare service engines may be arranged to employ rules, conditions, or the like, provided via configuration information to determine if a booking flow may be completed to account for local circumstances or local requirements.

Figure 16:
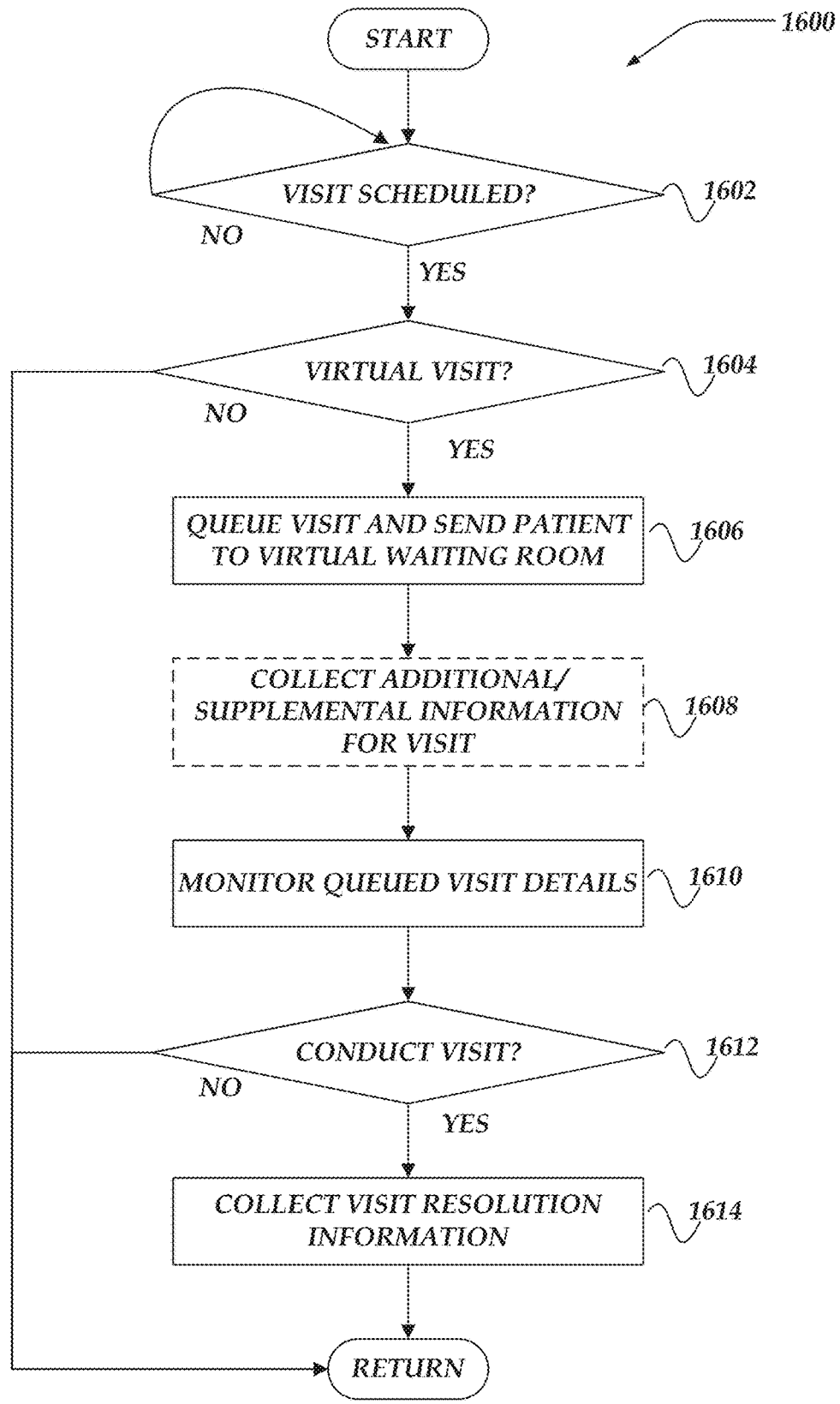
FIG. 16 illustrates a flowchart of a process for healthcare service platform in accordance with one or more of the various embodiments.

FIG. 16 illustrates a flowchart of process 1600 for healthcare service platform in accordance with one or more of the various embodiments. After a start block, at decision block 1602, in one or more of the various embodiments, if a visit is scheduled, control may flow to decision block 1604; otherwise, control may loop back to decision block 1602.

In some embodiments, healthcare service engines may be arranged to enable patient to schedule via the booking flow. In some cases, for some embodiments, healthcare service engines may enable one or more patients to schedule visit that may occur at a future time. Also, in some embodiments, healthcare service engines may be arranged to enable patients to schedule on-demand visits that may occur soon after the booking flow.

In one or more of the various embodiments, healthcare service engines may be configured to offer on-demand or other (e.g., scheduled) virtual visits to patients that may be a better match for their interests and needs while they are in the booking flow. For example, in some embodiments, a healthcare service engine may determine that a patient scheduling an in-person visit is eligible and better fit for an on-demand virtual visit given their interests and preferences, such as a preference for shorter wait times. Thus, in this example, a patient booking a conventional in-person visit may be provided an opportunity to have an on-demand virtual visit.

Otherwise, in some embodiments, patients may be enabled to engage with the healthcare service platform at or near the time of their scheduled visit time.

In one or more of the various embodiments, if a patient may be logged into the healthcare service platform for a visit, the healthcare service engines may be arranged to provide one or more user interfaces to collect any last-minute information or to confirm one or more relevant details of the patient visit profile before preceding.

At decision block 1604, in one or more of the various embodiments, if the scheduled visit is a virtual visit, control may flow to block 1606; otherwise, control be returned to a calling process.

In some embodiments, in-person visits may benefit from patient visit profiles, or the like, collected during booking flows. For example, healthcare service engines may be arranged to forward some or all of the information collected during a booking flow to a patient EMR, or the like, the provider may review as part of the in-person visit. Likewise, in some embodiments, providers or provider organization representatives may enabled to update patient visit profiles based on information learned or collected during the in-person visit.

At block 1606, in one or more of the various embodiments, healthcare service engines may be arranged to queue the visit and transfer the patient associated with the queued visit to a virtual waiting room.

In one or more of the various embodiments, healthcare service engines may be arranged to add the patient to a queue that may be visible to provider organization representatives in provider organization portals described above.

In one or more of the various embodiments, healthcare service engines may be arranged to provide more than queue, each directed to different types of visits, or the like. In some embodiments, healthcare service engines may be arranged to maintain a global queue of patients as well as one or more specialized queued.

In some embodiments, specialized queues may be designated based on various characteristics of the visit, such as, assigned provider, visit type, location, patient type, visit reason, clinic priorities, other triage factors, or the like. In some embodiments, healthcare service engines may be arranged to provide a priority or emphasis queue that may list queued patients (patient visit profiles) that meet one or more conditions, such as, excessive wait time, urgent needs, or the like.

As described above, in some embodiments, healthcare service engines may be arranged to generate user interfaces to provide a virtual waiting room for the patient.

At block 1608, in one or more of the various embodiments, optionally, healthcare service engines may be arranged to collect additional or supplemental information that may be associated with the queued visit. In one or more of the various embodiments, healthcare service engines may be arranged to provide user interfaces that enable provider organization representatives to interact with queued patients while they are in a virtual waiting room. In some embodiments, one or more interactions, such as, technology/system checks may be conducted to verify that the patient has the technical capability to conduct a virtual visit.

Also, in some embodiments, healthcare service engines may be arranged to automatically prompt patients for information to supplement the patient visit profile. For example, in some embodiments, queued patients may be prompted to provide additional reason-for-visit information. In some embodiments, healthcare service engines may be arranged to employ decision trees or natural language processing to identify ambiguous statements that may be clarified by automatically asking one or more questions.

Likewise, in some embodiments, healthcare service engines may be arranged to ask one or more questions associated with symptoms that may be described by the patient or inferred from the patient visit profile. In some embodiments, if the patient visit profile was initially generated sometime ago, healthcare service engines may be arranged to provide questions to patients to determine if the reported symptoms have changed.

In one or more of the various embodiments, healthcare service engines may be arranged to prompt provider organization representatives to ask one or more questions via chat, video, telephone, or the like, to update/clarify symptoms.

Note, this block is indicated as being optional because in some cases for some embodiments additional or supplemental information may not be available or otherwise provided.

At block 1610, in one or more of the various embodiments, healthcare service engines may be arranged to monitor visit details for the queued visit.

As described above, in some embodiments, healthcare service engines may be arranged to monitor one or more metrics associated with queued visits, including wait time, chats, or the like. In some embodiments, healthcare service engines may be arranged to occasionally generate user interfaces to interact with queued patients while they wait.

In some embodiments, healthcare service engines may be arranged to enable provider organization representatives to conduct one or more pre-visit actions to prepare for the visit. In some embodiments, this may include collecting or confirming information in the patient visit profile. For example, in some embodiments, if the mailing address provided by the patient mismatches the mailing address currently on record at the provider organization, a provider organization representatives may be enabled to confirm which mailing address is correct. Likewise, other information, such as, insurance information, payment information, or the like, may be confirmed if it may not be consistent with previously collected information.

In one or more of the various embodiments, healthcare service engines may be arranged to infer if queued patients may be away from their computer. For example, in some embodiments, if a patient may be determined to away from the keyboard when it is time for a visit, healthcare service engines may be arranged to automatically text or call the patient with automated messages to notify them that it is time for the visit. Likewise, in some embodiments, healthcare service engines may be arranged to notify provider organization representatives or providers that a patient is away from their computer and may need a reminder call to bring them to the virtual visit.

At decision block 1612, in one or more of the various embodiments, if the visit may be conducted, control may flow to block 1614; otherwise, control may be returned to a calling process. In some cases, visits may be canceled or rescheduled. In some embodiments, healthcare service engines may be arranged to automatically cancel visits if supplemental information indicates that the visit should be canceled. Likewise, in some embodiments, provider organizations may be enabled to cancel visits based on patient visit profiles or other interactions with queued patients. In some cases, technical problems with patient computers, network connections, or the like, may cause one or more queued patients to drop out of the queue. Also, in some embodiments, queued patients may drop out of the queue on their own volition.

In some embodiments, if a patient unexpectedly drops out of the queue, healthcare service engines may be arranged to record the event to enable provider organization representatives to followup with patients that may be unable to complete the visit. Additionally, in some embodiments, in such situations, providers may be automatically or manually matched with and assigned to new patient visits.

At block 1614, in one or more of the various embodiments, healthcare service engines may be arranged to collect various information associated with the resolution of the visit.

In one or more of the various embodiments, healthcare service engines may be arranged to provide user interfaces to collect satisfaction surveys from the patients. Likewise, user interfaces may be provided to providers or other provider organization representatives to collect information about the visit.

In some embodiments, visit resolution information may be collected in data stores. Accordingly, in some embodiments, healthcare service platforms may be enabled to perform subsequent data mining, machine learning training, or the like, to determine insights that may be incorporated in matching models, or the like.

Next, in one or more of the various embodiments, control may be returned to a calling process.

Figure 17:
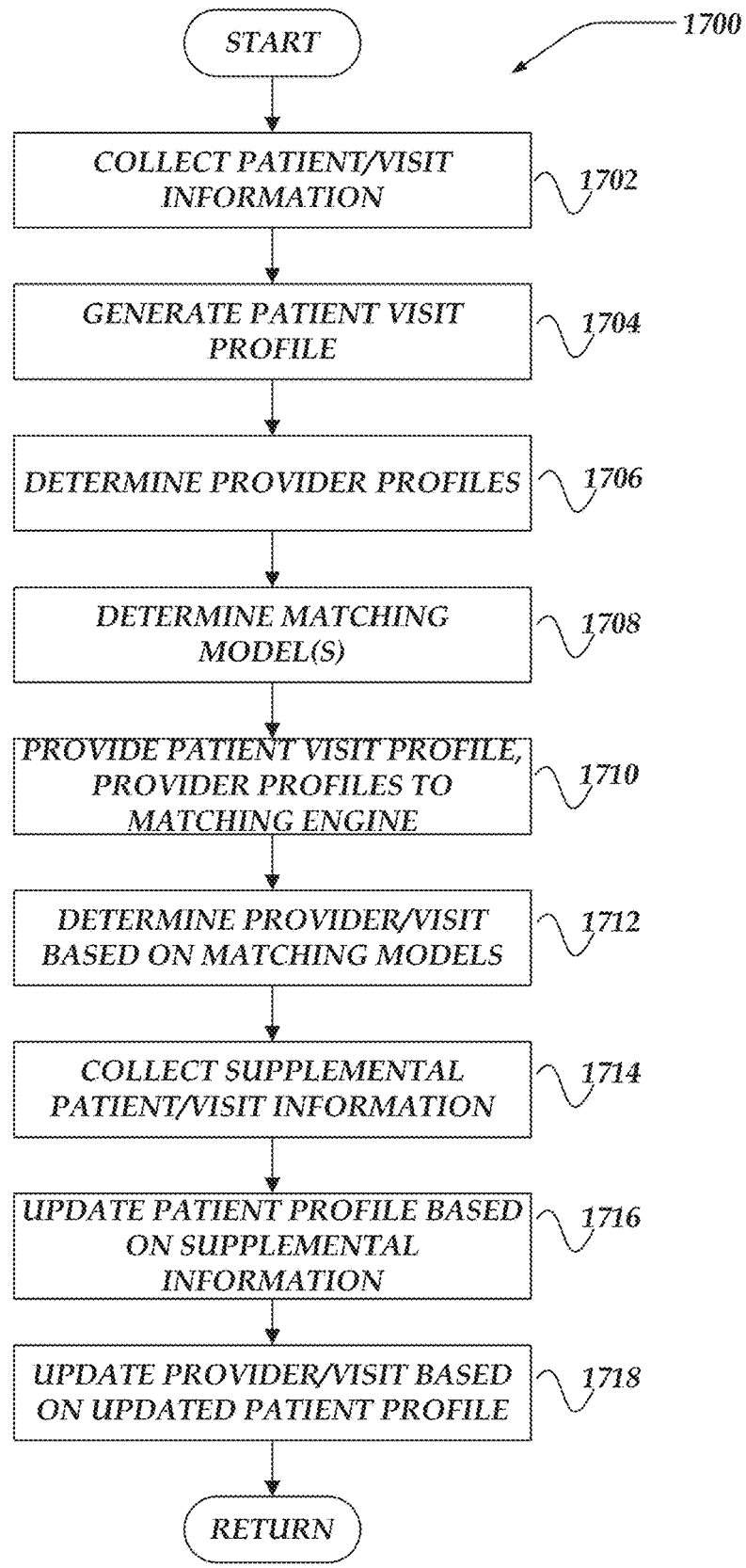
FIG. 17 illustrates a flowchart of a process for healthcare service platform in accordance with one or more of the various embodiments.

FIG. 17 illustrates a flowchart of process 1700 for healthcare service platform in accordance with one or more of the various embodiments. After a start block, at block 1702, in one or more of the various embodiments, healthcare service engines may be arranged to collect patient/visit information. As described above, healthcare service engines may be arranged to employ booking flow user interfaces to collect information about the patient, reasons for requesting a visit, or the like. Also, in some embodiments, information provided directly by patients may be supplemented by information collected from other sources, such as, EMR services, third party data stores, or the like.

At block 1704, in one or more of the various embodiments, healthcare service engines may be arranged to generate a patient visit profile for the patient associated with the visit. In one or more of the various embodiments, patient visit profiles may be data structures employed to collect or manage information about the patient or visit relevant to a visit. In some embodiments, patient visit profiles may include references/pointers that enable access to information from other data stores that may be associated with a visit.

In one or more of the various embodiments, patient visit profiles may include fields for patient information, visit information, scheduling information, or the like, that may be relevant for matching patient visits with providers or schedule times.

In one or more of the various embodiments, patient visit profiles may be arranged to include one or more core fields, such as, patient name, age, birth date, payor information, address information, or the like.

In one or more of the various embodiments, healthcare service engines may be arranged to enable provider organizations to customize patient visit profiles. Accordingly, in some embodiments, healthcare service engines may be arranged to enable provider organizations to define or declare one or more fields to include in the patient visit profiles.

In some embodiments, one or more of the fields selected to customize a patient visit profile may be selected from a set of fields provided by the healthcare service platforms. Accordingly, in some embodiments, such fields may be associated with other built-in features of the healthcare service platforms.

Also, in some embodiments, healthcare service engines may be arranged to enable provider organizations to define one or more custom fields that may be populated by other services or system (e.g., EMR services, clinic management applications, or the like). Accordingly, such fields may enable provider organizations to associate information with patient visit profiles that may not be associated directly with healthcare service platforms.

Further, in some embodiments, healthcare service engines may be arranged to enable provider organizations to customize patient visit profiles to include one or more 'dumb' fields that may store values, support validations rules, displayed in user interfaces, or the like, but otherwise are not associated with actions enabled or supported by the healthcare service engines.

At block 1706, in one or more of the various embodiments, healthcare service engines may be arranged to be determined one or more provider profiles associated with the visit.

In one or more of the various embodiments, provider profiles may be data structures that include fields that store values corresponding to a given provider. In some embodiments, provider profiles may include various information about a provider, such as, name, specialization, years of experience, cost, utilization, compensation type (e.g., salary, commission/production based, or the like), one or more grades, location, one or more provider preferences, case type preferences, case type experience, or the like. In some embodiments, provider information may include provider specific information derived from the history of the visits performed by the provider, including patient satisfaction, duration, issue resolution, treatments, referrals, or the like.

Also, in some embodiments, provider profiles may be arranged to include one or more references to other data sources that may store additional information associated with providers. Accordingly, in some embodiments, provider profiles may be associated with raw historical records, visit resolution information, patient history, visit history, or the like.

In one or more of the various embodiments, healthcare service engines may be arranged to filter provider profiles based on one or more field values of patient visit profiles. Accordingly, in some embodiments, healthcare service engines may be arranged to enable provider organizations to establish one or more filter rules that may be applied to include or exclude provider profiles from consideration before submitting them to matching engine. For example, providers that may be on vacation or otherwise unavailable may be initially filtered from consider. Alternatively, in some embodiments, healthcare service engines may be arranged to rely on matching engines to perform some or all preliminary filtering, At block 1708, in one or more of the various embodiments, healthcare service engines may be arranged to determine one or more matching models.

As described above, in some embodiments, healthcare service platforms may be arranged to have one or more matching models that may be stored in a matching model data store.

In some embodiments, healthcare service engines may be arranged to filter matching models based on one or more characteristics of the patient visit profile, both interests and preferences, as well as clinical history and needs. Accordingly, in some embodiments, one or more matching models may be excluded from consideration early. In some embodiments, this may improve performance by excluding one or more irrelevant matching models from being executed for a given patient visit profile.

In one or more of the various embodiments, healthcare service engines may be arranged to employ one or more matching models to filter or select one or more matching models that may be considered for a given patient visit profile. Accordingly, in some embodiments, healthcare service engines may be arranged to enable one or more matching models to be organized hierarchically such that one or more matching models arranged for high level filtering or for high level matching model selection may be executed to select other matching models that may perform actions that may require more compute or memory resources.

At block 1710, in one or more of the various embodiments, healthcare service engines may be arranged to provide the patient visit profile and provider profiles to a matching engine.

In one or more of the various embodiments, healthcare service engines may be arranged to provide the patient visit profiles and provider profiles as inputs to a matching engine.

At block 1712, in one or more of the various embodiments, healthcare service engines may be arranged to determine provider/visit based on the matching models and the matching engine.

In one or more of the various embodiments, matching engines may be arranged to employ one or more matching models to score matches between the patient visit profile and provider profiles. As mentioned above, one or more matching models may be organized into hierarchies that provide a reverse funnel to reduce the number of providers under consideration as evaluations/classification cascade through one or more subsequent matching models.

Also, in one or more of the various embodiments, some or all matching models may be comprehensive models that may be arranged to evaluate each provider profile for a given patient visit profile.

In some embodiments, matching models may be arranged to include one or more sub-models that may be comprised or filter, heuristics, machine learning models, or the like. Thus, in some embodiments, one or more matching models may be arranged to generate a comprehensive match score absent support from other matching models.

In one or more of the various embodiments, matching engines may be arranged to generate scores that represent a quality of match for one or more providers and the patient visit profile. In some cases, one or more providers may be automatically excluded or issued 'zero' scores based on filtering, availability, or the like, that may be unrelated to a matching model.

In one or more of the various embodiments, healthcare service engines may be arranged to automatically select a provider for a visit based on the match scores. In some embodiments, if a provider match score exceeds a threshold value, the corresponding provider may be automatically assigned to the visit.

Also, in some embodiments, if the none of the providers have a match score that exceeds an automatic assignment threshold value, healthcare service engines may provide a list of providers orders based on their corresponding match scores.

In one or more of the various embodiments, healthcare service engines may be arranged to enable provider organizations to configure rules for automatic assignment, such as, threshold score values, or the like. For example, if matching models are arranged to provide matching score that range from 0-100, scores greater than 90 may be considered for automatic assignment while score less than 90 but greater than 65 may be considered to recommend to assign rather than automatic assignment. Also, in some embodiments, healthcare service engines may be arranged to employ other statistical metrics to identify recommended providers.

Likewise, in some embodiments, matching engine may be arranged to provide matching scores that comprise vectors or tuples rather than being reduced to a single scalar value to allow more nuanced selection/recommendation criteria.

In some embodiments, to support modification, upgrades, experiments, or the like of matching models, healthcare service engines may be arranged to employ one or more rules, instructions, software libraries, or the like, provided (or identified) by configuration information to account for local circumstances or local requirements.

At block 1714, in one or more of the various embodiments, healthcare service engines may be arranged to collect supplemental information associated with the patient or visit.

As described above, supplemental information may be collected from a variety of sources. In some embodiments, patients may be enabled to provide additional information while they are in the virtual waiting room. In some cases, patients may be enabled to provide information for the visit sometime after they book the visit and when it is scheduled. For example, for some embodiments, if a virtual visit is scheduled in five days, a patient may employ the healthcare service platform to provide additional information that may be employed to update the patient visit profile.

At block 1716, in one or more of the various embodiments, healthcare service engines may be arranged to update the patient visit profile based on the supplemental information. As information supplemental information may be collected, healthcare service engines continuously update related patient visit profiles.

At block 1718, in one or more of the various embodiments, healthcare service engines may be arranged to update the provider or visit based on the updated patient visit profile. In some embodiments, if patient visit profiles may be updated, healthcare service engines may be arranged to go through some or all of the steps to determine match scores for providers based on the updated patient visit profile. In some cases, updates to the patient visit profile may result in new match scores. And, in some cases, these new match scores may be result in changes to the visit, such as, assigning a different provider, reserving additional/different resources, triggering the visit to be rescheduled, or the like.

Next, in one or more of the various embodiments, control may be returned to a calling process.

Figure 18:
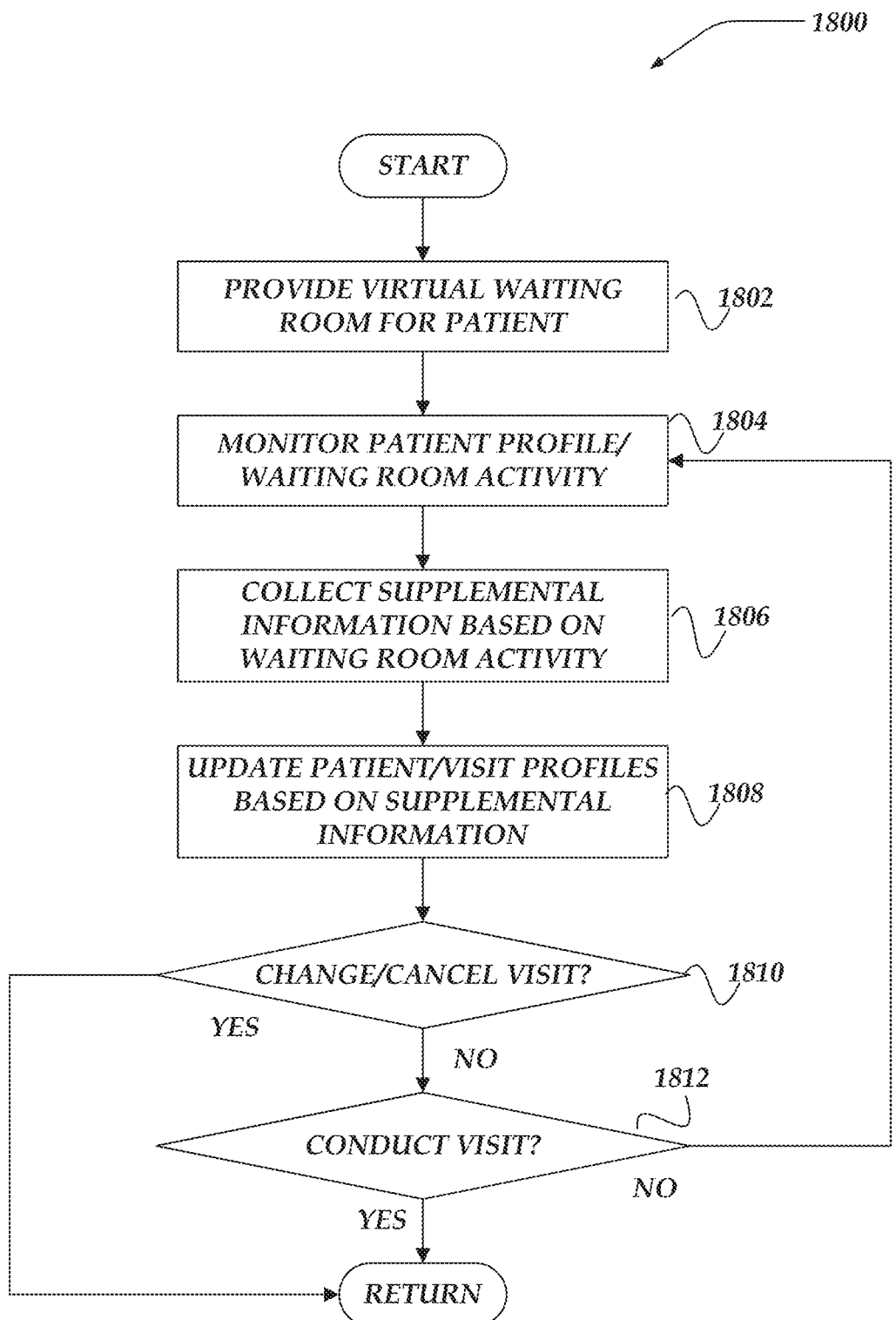
FIG. 18 illustrates a flowchart of a process for healthcare service platforms in accordance with one or more of the various embodiments.

FIG. 18 illustrates a flowchart of process 1800 for healthcare service platforms in accordance with one or more of the various embodiments. After a start block, at block 1802, in one or more of the various embodiments, healthcare service engines may be arranged to provide a virtual waiting room for the patient. In one or more of the various embodiments, healthcare service engines may be arranged to book patients for a virtual visit and then before the virtual visit begins, the patient may be provided access to one or more user interfaces that act as a virtual waiting room.

In some cases, in some embodiments, virtual waiting rooms may be configured to include one or more checklists of actions a patient should perform or information a patient should provide/confirm before going forward with a virtual visit. For example, in some embodiments, if the patient has not recently performed a technology system check, the healthcare service engines may offer to guide the patient through verifying that required systems, such as, video cameras, microphones, speakers/headphones, or the like, are configured correctly or otherwise sufficiently functioning before proceeding to the virtual visit.

In some embodiments, in some embodiments, healthcare service engines may be arranged to enable providers or provider organization representatives to view information associated with the virtual visit via a visit detail user interface, or the like. Thus, in some embodiments, authorized users may intervene and actively guide or encourage the patient to perform one or more desired actions or request that they supply requested information.

Likewise, in some embodiments, healthcare service engines may be configured to enable providers or provider organization representatives to actively engage with the queued patient via chat applications, video, audio, or the like, to confirm some or all of the information provided by the patient. Likewise, providers or provider organization representatives may be enabled resolve one or more information conflicts. For example, if demographic information provided by the patient may conflict with information stored in another data store (e.g., EMRs), healthcare service engines may flag the conflicts and enable a provider representative to take one or more actions to resolve or waive the conflict.

At block 1804, in one or more of the various embodiments, healthcare service engines may be arranged to monitor updates to the patient visit profile or waiting room activity.

In one or more of the various embodiments, healthcare service engines may be arranged to track if queued patients add or update information associated with visits while they may be in the virtual waiting room.

Likewise, in some embodiments, for various reasons, providers or provider organization representatives may modify/update, patient information, visit information, or the like, while the patient is in the virtual waiting room. Accordingly, in some embodiments, healthcare service engines may be arranged to detect such modifications and update patient visit profiles as needed.

Also, in one or more of the various embodiments, monitoring virtual waiting rooms may include monitoring the amount of time the patient is queued for the visit.

Further, in some embodiments, healthcare service engines may be arranged to monitor the status of providers that may be scheduled to conduct the visit. In one or more of the various embodiments, changes in provider status may cause a visit to be delayed or otherwise altered. For example, if the scheduled provider is called away for a higher priority activity (e.g., emergency response), the healthcare service engine may detect the provider status change and updated the visit information accordingly.

At block 1806, in one or more of the various embodiments, healthcare service engines may be arranged to collect supplemental information based on the waiting room activity. In some embodiments, supplemental information may be provided directly through patient or provider interaction within the virtual waiting.

Also, in some embodiments, healthcare service engines may be arranged to collect supplemental information from other sources based on direct interactions of patients or providers. In some embodiments, if a patient updates demographic information, a match with other records or information known to the healthcare service platform may be determined. For example, if the initial identity information provided by the patient does not match a known patient record, subsequent collection of information from the patient may enable a qualified match. Accordingly, in this example, a qualified match may enable healthcare service engines to collect supplemental information from an EMR, or the like, for the patient.

Likewise, in some embodiments, healthcare service engines may be arranged to interpret chat text, updates/clarifications to visit reasons, or the like, to generate supplemental information. For example, if a patient includes more details about the reasons for the visit in a chat with a medical assistant, healthcare service engines may be arranged to determine supplemental information based on updated details. In general, here supplemental information may be considered information that may be derived or determined based on monitored interactions/updates that may occur while the patient may be in the virtual waiting room or otherwise queued.

At block 1808, in one or more of the various embodiments, healthcare service engines may be arranged to update patient visit profiles based on the supplemental information. In one or more of the various embodiments, some or all of the supplemental information may be included in the patient visit profile. In some embodiments, meta-data about the supplemental information may be included in the patient visit profile. For example, the source of the supplemental information or the reason for the inclusion of the supplemental information may be included in the patient visit profile.

In some embodiments, healthcare service engines may be arranged to submit updated patient visit profiles to matching engines. Accordingly, in some embodiments, matching engines may be arranged to provide the updated profiles as inputs to one or more matching models.

At decision block 1810, in one or more of the various embodiments, if the visit may be canceled or changed, control may be returned to a calling process; otherwise, control may flow to decision block 1812. In one or more of the various embodiments, changes to patient visit profiles may result in changes to visit. In some embodiments, changes may include changing providers, changing/modifying the resources that may be reserved for the visit, requesting interpreters, scheduling a particular examination room that may have the necessary examination/diagnostic equipment, or the like.

In one or more of the various embodiments, if the visit may require changing, healthcare service engines may be arranged to re-queue or re-schedule the patient. In some cases, the information determined while the patient was in the virtual waiting room may result in updating the EMR, provider briefing, or the like, rather than requiring a visit to be rescheduled.

Also, in some embodiments, healthcare service engines may be arranged to determine if the visit may be transparently re-scheduled, such as, the visit may be conducted without delay. Accordingly, in some embodiments, if the necessary changes to visit can occur without delay the visit may proceed.

In some cases, for some embodiments, the supplemental information may indicate that a virtual visit may not be appropriate for the patient. Accordingly, in some embodiments, healthcare service engines may be arranged to cancel the virtual visit and request that the patient schedule an in-person visit. In some embodiments, if there may be sufficient information previously collected, another visit may be automatically scheduled.

Also, in some cases, for some embodiments, the supplemental information may indicate that the queued patient may be undergoing a medical emergency. Accordingly, in some embodiments, healthcare service engines may be arranged to cancel the visit, switch to an on-demand visit for immediate attention, and notify the provider organization to contact emergency services for the patient.

At decision block 1812, in one or more of the various embodiments, if the visit may be conducted, control be returned to a calling process; otherwise, control may loop back to block 1804.

Next, in one or more of the various embodiments, control may be returned to a calling process.

Figure 19:
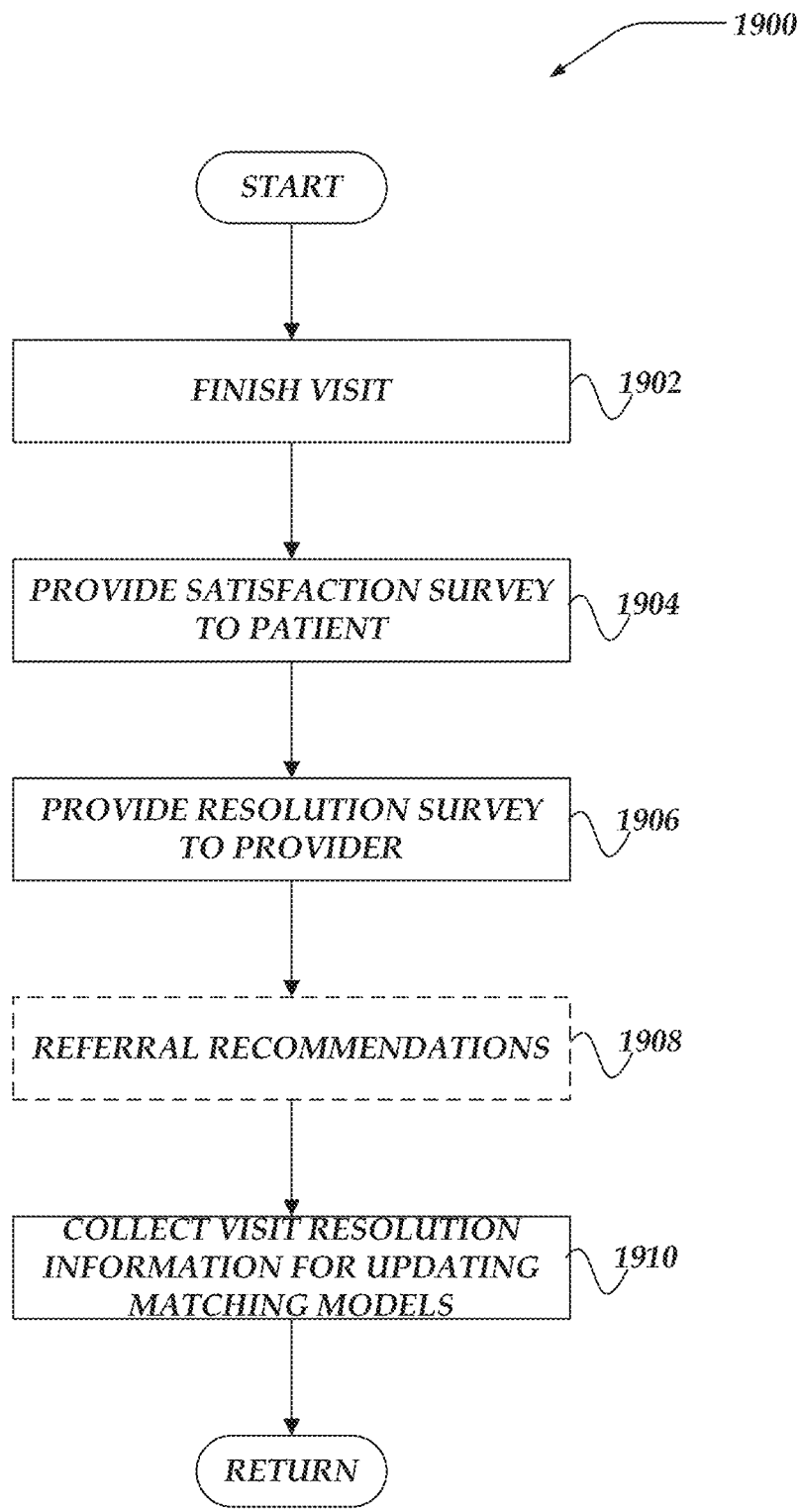
FIG. 19 illustrates a flowchart of a process for healthcare service platform in accordance with one or more of the various embodiments.

FIG. 19 illustrates a flowchart of process 1900 for healthcare service platform in accordance with one or more of the various embodiments. After a start block, at block 1902, in one or more of the various embodiments, healthcare service engines may be arranged to monitor visit information until the visit may be completed. As described above, healthcare service engines may be arranged to enable patients and providers to conduct a visit. In some embodiments, visits may be virtual visits that may be conducted using one or more of telephonic communication, video conferencing, voice-over-ip, text/chat, exchanged documents, remote diagnostic tools, or the like, or combination thereof.

Also, in some embodiments, healthcare service engines may be arranged to support in-person visits by monitoring electronic chart entries, check-in/check-out times, supplemental orders, lab reports, or the like, that may be associated with an in-person visit.

Accordingly, in some embodiments, if a visit may be completed, healthcare service engines may be arranged to collect visit resolution information.

At block 1904, in one or more of the various embodiments, healthcare service engines may be arranged to provide one or more user interfaces for collecting information related to the patient's satisfaction with the visit. In one or more of the various embodiments, if a virtual visit has completed, healthcare service engines may be arranged to automatically provide one or more user interfaces to the patient via the device/application that was used to conduct the virtual visit. For example, if the virtual visit was a video conference at a desktop computer, the user interfaces for collecting satisfaction information may be presented on the desktop computer. Likewise, in some embodiments, if the virtual visit was conducted using a mobile telephone application, the user interfaces for collecting satisfaction information may be displayed on the patient's mobile telephone.

In one or more of the various embodiments, healthcare service engines may be arranged to provide one or more user interfaces to collect categorical satisfaction information, such as, "star" ratings or "1-10" ratings. In some embodiments, healthcare service engines may be arranged to provide user interfaces to inquire about more than one part of the visit, such as, technology quality, timeliness, communication quality, or the like. In some embodiments, user interfaces may include a question asking if the patient thinks the reason for the visit has been resolved.

Also, in some embodiments, healthcare service engines may be arranged to provide user interfaces that collect text, voice, video feedback in the own words of the patient. Accordingly, in some embodiments, healthcare service engines may be arranged to employ NLP or other video analysis facilities to perform sentiment analysis, or the like, of the free form or other feedback.

In some embodiments, if the visit was an in-person visit, healthcare service engines may be arranged to provide notifications to patients via text/SMS, email, in-application notifications, or the like, that ask the patient to complete to the post visit survey. In some embodiments, provider organizations may provide computer kiosks or tablet computers that enable patients to provide post-visit feedback at clinics.

In some embodiments, if it may not be convenient for the patient to provide visit feedback immediately after the visit, healthcare service engines may be arranged to enable patients to delay or defer answering post-visit surveys.

In one or more of the various embodiments, healthcare service engines may be arranged to enable provider organizations to customize post-visit surveys. In some embodiments, healthcare service engines may be arranged to enable post-visit surveys to be selected or customized based on one or more factors, including, type of visit, type of provider (e.g., contractor, visiting professional, physician, medical assistant, nurse, or the like), type of patient (in-network, out-of-network, walk-in, other demographics, or the like), reason for visit, or the like. Accordingly, in some embodiments, healthcare service engines may be arranged to employ templates, rules, instructions, or the like, provided via configuration information to determine user interfaces for post-visit surveys or questions to include in post-visit surveys.

At block 1906, in one or more of the various embodiments, healthcare service engines may be arranged to provide one or more user interfaces to the provider to collect information related to the resolution of the visit. Similar to collecting post-visit information from patients, healthcare service engines may be arranged to collect post-visit information from providers.

In some embodiments, provider post-visit surveys may include asking about visit fee waivers/adjustments, rescheduling, followup visits, prescriptions, or the like.

Also, in some embodiments, visit resolution surveys may include a question that asks if the visit has resolved the reason for the visit. For example, in some embodiments, during a virtual visit, a provider may determine that an in-person visit may be necessary to properly diagnose or treat the patient's issue. Accordingly, in this example, the fee (if any) for the virtual visit may be waived and an in-person visit scheduled.

In one or more of the various embodiments, healthcare service engines may be arranged to enable provider organizations to customize post-visit provider surveys. In some embodiments, healthcare service engines may be arranged to enable post-visit surveys to be selected or customized based on one or more factors, including, type of visit, type of provider (e.g., contractor, visiting professional, physician, medical assistant, nurse, or the like), type of patient (in-network, out-of-network, walk-in, other demographics, or the like), reason for visit, or the like. Accordingly, in some embodiments, healthcare service engines may be arranged to employ templates, rules, instructions, or the like, provided via configuration information to determine user interfaces for post-visit surveys or questions to include in post-visit surveys.

At block 1908, in one or more of the various embodiments, optionally, healthcare service engines may be arranged to provide one or more user interfaces that enable the provider to issue one or more referrals to the patient.

In one or more of the various embodiments, during the course of a visit, a provider may determine that the patient should be referred to another provider.

In some embodiments, healthcare service engines may be arranged to recommend to provider if a referral should be considered. In one or more of the various embodiments, healthcare service engines may be arranged to determine to recommend providers based on an analysis of the patient visit profile or other visit metrics. For example, in some embodiments, one or more machine learning models may be trained to recognize/predict if a patient may require a referral based on metrics or inputs associated with the patient visit profile, the provider, one or more visit metrics, or the like. In some embodiments, healthcare service engines may be arranged to parse the "reason for the visit" submissions to determine if referrals to other providers should be considered. For example, if the reasons for the visit or text/chats indicate that the patient is having blurred vision, referrals with neurologists, vision specialists, or the like, may be automatically suggested.

Also, in some embodiments, healthcare service engines may be arranged to enforce one or more referral policies of the provider organization. For example, a provider organization may configure their healthcare service platform to always make referrals based on certain key words or key phrases being included in reasons-for-visit submissions. Likewise, for example, a provider organization may configure their healthcare service platform to always provide referral suggestions if one or more vital signs or other patient metrics may be out-of-range. For example, healthcare service engines may be configured to suggest referral to dietary consultants, or the like, for patients that have a BMI above a defined threshold.

Accordingly, in one or more of the various embodiments, healthcare service engines may be arranged to employ rules, instructions, machine learning models, or the like, provided or determine via configuration information to determine if referral should be recommended.

Note, this block is indicated as being optional because in some cases referrals to other providers or other care services may not be required or available.

At block 1910, in one or more of the various embodiments, healthcare service engines may be arranged to collect the visit resolution information for updating matching models.

In one or more of the various embodiments, healthcare service engines may be arranged to store post-visit survey information in a one or more data stores. Accordingly, in some embodiments, this information may be subsequently employed for data mining, machine learning model training, report generation, or the like.

Next, in one or more of the various embodiments, control may be returned to a calling process.

Figure 20:
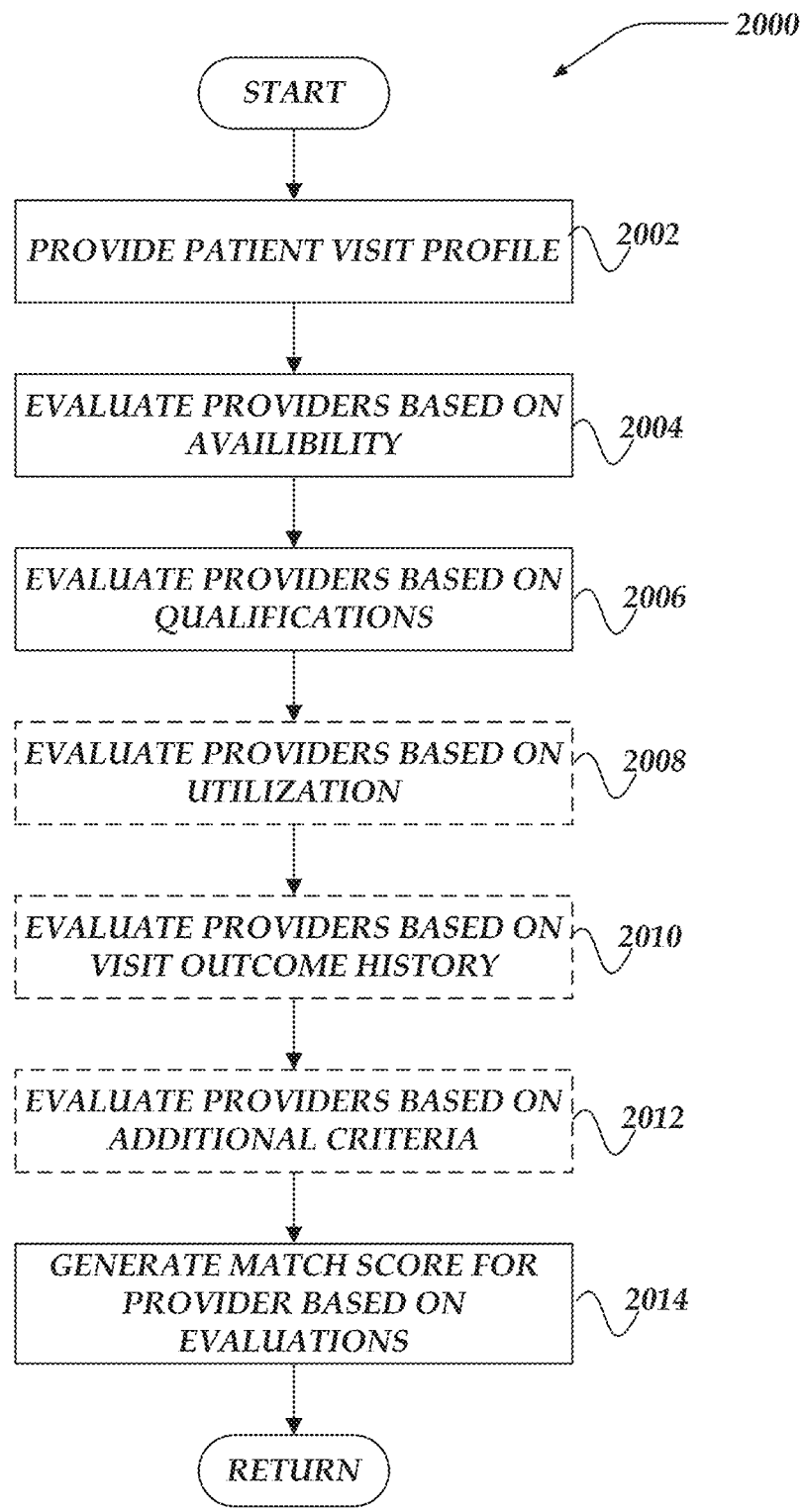
FIG. 20 illustrates a flowchart of a process for generating match scores for visits for healthcare service platforms in accordance with one or more of the various embodiments.

FIG. 20 illustrates a flowchart of process 2000 for generating match scores for visits for healthcare service platforms in accordance with one or more of the various embodiments. After a start block, at block 2002, in one or more of the various embodiments, matching engines may be provided a patient visit profile, one or more matching models, one or more provider profiles, or the like.

As described above, in some embodiments, healthcare service engines may generate patient visit profiles based on information collected from various sources, including booking flows, virtual waiting room interactions, history information, or the like. Also, in some embodiments, one or more provider profiles that represent providers in a provider organization may be provided. Also, in some embodiments, one or more matching models may be provided to determine match scores for the one or more providers and the visit.

At block 2004, in one or more of the various embodiments, matching engines may be arranged to evaluate the one or more providers based on availability. Similar, to requiring providers to be qualified, providers should be available for assignment before undergoing further consideration.

In some embodiments, healthcare service engines may be arranged to evaluate the availability of providers before providing them to a matching engine. In some embodiments, healthcare service engines may be arranged to integrate with one or more other scheduling services that may provide availability information about providers. For example, in some embodiments, providers that are on vacation, away for training, or the like, may be automatically excluded from consideration before determining match scores for them.

In one or more of the various embodiments, healthcare service engines may be arranged to consider availability in more than one context. In some cases, availability may represent that a provider is available 'now' for instant/on-demand virtual visits, walk-in patients, urgent visits, or the like. Also, in some embodiments, availability may be considered across of a range of time or days for visits that may be scheduled in the future.

In some embodiments, patients may be enabled to provide a range of date or times that would be suitable or proffered for a visit. Accordingly, in some embodiments, healthcare service engines or matching engines may exclude providers from consideration if they may be unavailable during those times or days.

At block 2006, in one or more of the various embodiments, matching engines may be arranged to employ the one or more matching models to evaluate the one or more providers based on provider qualifications.

In one or more of the various embodiments, before providers may be further considered for a given visit, matching engines (via matching models) may be arranged to determine if a provider may be legally/medically qualified to provide care for the visit. In some embodiments, this may include confirming that a provider meets regulatory requirements for a visit. Likewise, in some embodiments, this may include determining if professional qualifications of providers may be suitable for the visit.

In some cases, for some embodiments, professional qualifications may be required based on regulatory rules or internal rules for a provider organization. For example, provider organizations may be enabled to configure rules for determining if a provider may be qualified for a visit. For example, in some cases, a provider organization may restrict some professionals from some visits based on years in practice metrics, specialty certifications, or the like, that may not be regulatory restrictions.

In one or more of the various embodiments, matching models may include qualification rules that may exclude one or more providers from further consideration. In some cases, in some embodiments, healthcare service engine or matching engines may be arranged to provide qualification rules that may be executed before individual matching models may be considered or evaluated. However, in terms of these innovations, such filtering rules may be considered part of one or more matching models or a separate matching model.

In one or more of the various embodiments, healthcare service platforms may be arranged to enable provider organizations to establish provider qualifications based on rules, instructions, filter settings, matching models, or the like, that may be provided via configuration information to account for local circumstances or local requirements.

At block 2008, in one or more of the various embodiments, optionally, matching engines may be arranged to evaluate the one or more providers based on utilization.

In one or more of the various embodiments, provider organizations may desire to balance the workload of providers for various reasons. In some cases, providers that are dedicated to handling particular visit types, or those providers that may be underutilized may be preferred over others. Likewise, in some embodiments, permanent staff providers may be favored over contractors or temporary employees. Also, in some embodiments, one or more providers may be enabled to establish preferences that may be considered to limit assignments to some types of visits. For example, in some cases, a provider may prefer that no more than 20% of her cases be of a particular type.

Also, in some embodiments, healthcare service engines may be arranged to enable providers to provide preference scores for various types of visits that may be considered if utilization may be considered.

In one or more of the various embodiments, healthcare service platforms may be arranged to enable provider organizations to establish rules for considering utilization based on rules, instructions, filter settings, matching models, or the like, that may be provided via configuration information to account for local circumstances or local requirements.

Note, this block is indicated as being optional because in some cases for some embodiments provider organizations may not consider provider utilization for determining match scores.

At block 2010, in one or more of the various embodiments, optionally, matching engines may be arranged to evaluate the one or more providers based on visit outcome history.

As described above, in one or more of the various embodiments, healthcare service engines may be arranged to collect various metrics associated with conducted visits. In some embodiments, such metrics may include, duration of visit, patient satisfaction, visit resolution information, or the like.

Also, in some embodiments, healthcare service engines may be arranged to monitor other metrics including, number of return visits, long term outcomes, or the like.

Accordingly, healthcare service engines may be arranged to develop a historical record that may be evaluated to determine if particular providers may be better suited for particular visits or particular patients. In some embodiments, healthcare service engines may be arranged to train machine learning classifiers, predictive models, or the like, that may enable providers to be evaluated based on historical visit outcome information.

Accordingly, in one or more of the various embodiments, healthcare service platforms may be arranged to enable provider organizations to establish consideration historical visit outcomes based on rules, instructions, filter settings, matching models, or the like, that may be provided via configuration information to account for local circumstances or local requirements.

Note, this block is indicated as being optional because in some cases for some embodiments provider organizations may not consider historical visit outcomes for determining match scores.

At block 2012, in one or more of the various embodiments, optionally, matching engines may be arranged to evaluate the one or more providers based on additional criteria.

One of ordinary skill in the art will appreciate that different provider organizations may have different criteria for matching providers to visits based on one or more policies. Accordingly, in some embodiments, healthcare service engine may be arranged to enable provider organization representatives to set additional criteria. Likewise, in some embodiments, healthcare service engines may provide a list of collected metrics that a provider organization may be enabled to select for inclusion in the matching evaluation. Likewise, in some embodiments, healthcare service engines may be arranged to enable providers to associate weight values with criteria to represent the importance (to the provider organization) of a given criteria or metric.

In some embodiments, healthcare service engines may be arranged to enable provider organizations to assign different threshold values for various metrics that may be considered for matching scores.

Accordingly, in one or more of the various embodiments, healthcare service platforms may be arranged to enable provider organizations to establish consideration of one or more additional criteria based on rules, instructions, filter settings, matching models, or the like, that may be provided via configuration information to account for local circumstances or local requirements.

At block 2014, in one or more of the various embodiments, matching engines may be arranged to generate one or more match scores for the one or more providers based on the evaluations.

In one or more of the various embodiments, matching engines may be arranged to generating match scores that enable each of the one or more providers to be ranked based on the match scores. In some embodiments, match scores may be a single value determined from a known range, such as, a value between 0-100, 0.0-1.0, or the like. In some embodiments, matching engines may be arranged to provide match scores in the form of vectors or tuples that include one or more sub-scores that may correspond to different criteria. In some embodiments, if more than one or more matching model may be employed, each matching model may supply a portion of the final match score. Accordingly, in such cases, for some embodiments, match score vectors or tuples may include each score provided by each matching model.

In one or more of the various embodiments, healthcare service engines may be arranged to employ match scores to rank providers for assignment to a visit.

Next, in one or more of the various embodiments, control may be returned to a calling process.

It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware-based systems, which perform the specified actions or steps, or combinations of special purpose hardware and computer instructions. The foregoing example should not be construed as limiting or exhaustive, but rather, an illustrative use case to show an implementation of at least one of the various embodiments of the invention.

Further, in one or more embodiments (not shown in the figures), the logic in the illustrative flowcharts may be executed using an embedded logic hardware device instead of a CPU, such as, an Application Specific Integrated Circuit (ASIC), Field Programmable Gate Array (FPGA), Programmable Array Logic (PAL), or the like, or combination thereof. The embedded logic hardware device may directly execute its embedded logic to perform actions. In one or more embodiments, a microcontroller may be arranged to directly execute its own embedded logic to perform actions and access its own internal memory and its own external Input and Output Interfaces (e.g., hardware pins or wireless transceivers) to perform actions, such as System On a Chip (SOC), or the like.

What is claimed as new and desired to be protected by Letters Patent of the United States is:

1. A method for managing provisioning of healthcare services over a network, wherein the method is configured to cause one or more network computers that include one or more processors to perform actions, comprising:
generating one or more user interfaces for a patient to provide a visit profile and request a visit to obtain healthcare services from a provider organization, wherein the visit profile includes geo-location information for the patient and one or more of a reason for the visit, symptom of an illness, sociographic information, or patient information, and wherein the provider organization employs the visit profile to select one or more of an interface control or local information that is included in the one or more user interfaces generated for the patient;
generating a booking flow representing intermediate progress of the patient for a current process that includes a plurality of portions in booking the visit, wherein the booking flow is used by one or more health care service engines to continuously and simultaneously provide for starting and stopping progress in the plurality of portions for booking the same visit by the patient from a plurality of types of applications that provide remote access to one or more portions of the one or more user interfaces generated to guide the patient through the booking flow based on conforming to one or more of a health care setting or a modality that aligns with both the patient's interests and one or more policies of the provider organization, and wherein the plurality of application types include one or more of a mobile application, a desktop application or an online application;
dynamically generating one or more selected user interfaces for the patient during the intermediate progress based on information collected during one or more of the plurality of portions for the current process to complete booking the visit;
determining one or more providers that are associated with the provider organization and are locally available to provide the requested healthcare services and virtually available to provide the requested healthcare services;
generating one or more matching models based on a localized requirement for the requested healthcare services, an objective of the provider organization, one or more metrics for outcome histories associated with the one or more providers, and heuristic data for the requested healthcare services;
generating one or more match scores for the one or more providers based on the one or more matching models and the visit profile, wherein each match score represents a quality of a match for assigning the one or more providers to the visit requested by the patient;
assigning a provider that is locally available for the visit and assigning an alternate provider that is virtually available for the visit based on the one or more match scores;

providing a virtual waiting room for the patient based on the visit profile, wherein one or more user interfaces in the virtual waiting room enable one or more interactions between the patient and the virtual waiting room, and wherein the virtual waiting room includes an estimated travel time, a cost, and a wait time to meet in person with the locally available provider and further includes an alternate cost, and an alternate wait time to communicate with the virtually available alternate provider;

updating the visit profile with supplemental information based on one or more of an interaction between the patient and the virtual waiting room, patient information from one or more data stores, or visit information from the one or more data stores;

providing one or more updated match scores for the one or more providers based on the one or more matching models and the updated visit profile; and in response to an updated match score exceeding a previously determined higher match score, assigning one or more of another provider or another alternate provider to the visit based on the other provider or the other alternate provider being associated with the updated match score, wherein the visit is conducted by the other provider or the other alternate provider.

2. The method of claim 1, wherein the one or more interactions between the patient and the virtual waiting room, further comprise, one or more of:

exchanging text chat messages with the patient and the provider organization;

verifying that the patient has a technical capability to virtually conduct the visit;

collecting one or more audio samples or one or more video samples from the patient; or employing one or more survey questions to collect one or more responses from the patient.

3. The method of claim 1, wherein providing the one or more match scores for the one or more providers, further comprises:

determining one or more of the one or more providers that are qualified based on the visit profile and the one or more matching models;

determining an availability of each qualified provider based on the visit profile and schedule information; and providing the match score for each available qualified provider.

4. The method of claim 1, further comprising:

in response to a conclusion of the visit, performing further actions, including:

providing one or more user interfaces to the patient;

employing the one or more user interfaces to collect additional patient information that includes satisfaction information provided by the patient;

collecting additional visit information that include duration values for one or more portions of a visit from booking of the visit to conclusion of the visit; and updating the one or more matching models based on the patient satisfaction information.

5. The method of claim 1, further comprising:

in response to a conclusion of the visit, performing further actions, including:

providing one or more user interfaces to the provider; employing the one or more user interfaces to collect visit resolution information from the provider;

updating the one or more matching models based on the visit resolution information; and in response to the visit remaining unresolved, performing further actions, including:

reducing or waiving a fee associated with the visit;

recommending or scheduling one or more follow-on visits, including recommending or scheduling one or more follow-on visits with one or more specialized providers;

updating the updated visit profile based on the resolution information; or scheduling another visit based on the updated visit profile.

6. The method of claim 1, wherein generating the one or more match scores for the one or more providers, further comprises:

determining one or more first partial match scores based on a utilization metric associated with each provider, wherein the utilization is based on one or more of a utilization history associated with each provider, a defined goal associated with each provider, one or more other metrics associated with each provider;

determining one or more second partial match scores based on outcome information associated with the one or more providers and an equivalent visit type as the visit, wherein the outcome information includes one or more of outcome history, effectiveness, or other information associated with the one or more providers;

determining one or more third partial match scores based on one or more metrics associated with the visit and one or more policies of the provider organization, wherein the one or more metrics associated with the visit, include one or more of definitive issue resolution, high patient satisfaction, high provider satisfaction, reduced visit duration, reduced cost, greater efficiency of delivering care in the visit, alignment with stated or predicted patient preferences, and wherein the stated or predicted patient preferences include one or more of location, language, ethnicity, gender or other patient preferences; and providing the one or more match scores based on one or more of the one or more first partial match scores, the one or more second partial match scores, or the one or more third partial match score.

7. The method of claim 1, further comprising:

adding the patient to one or more visit queues;

monitoring a duration that the patient is in the one or more visit queues;

generating and sharing wait times or other feedback with the patient; and in response to the duration that the patient is in the one or more visit queues exceeding a threshold value, performing further actions, including:

generating one or more notifications to notify one or more representatives of the provider organization the queue duration is exceeding the threshold value;

updating the visit profile based on the queue duration exceeding the threshold value; and assigning the visit to another provider based on the updated visit profile.

8. The method of claim 1, further comprising:

determining the quality of the match based on a combination of an alignment of stated or predicted patient preferences, including one or more of location, language, ethnicity, gender, patient preference, or provider preference; and determining a greatest likelihood of achieving a particular goal, including, one or more of definitive issue resolution, positive clinical outcome, high patient satisfaction, high provider satisfaction, reduced visit duration, reduced costs, greater efficiency of delivering care in the visit, or greater or more balanced provider utilization.

9. A system for managing provisioning of healthcare services:
one or more network computers, comprising:
a memory that stores at least instructions; and
one or more processors that execute instructions that are configured to cause the one or more network computers to perform actions, including:
generating one or more user interfaces for a patient to provide a visit profile and request a visit to obtain healthcare services from a provider organization, wherein the visit profile includes geo-location information for the patient and one or more of a reason for the visit, symptom of an illness, sociographic information, or patient information, and wherein the provider organization employs the visit profile to select one or more of an interface control or local information that is included in the one or more user interfaces generated for the patient;
generating a booking flow representing intermediate progress of the patient for a current process that includes a plurality of portions in booking the visit, wherein the booking flow is used by one or more health care service engines to continuously and simultaneously provide for starting and stopping progress in the plurality of portions for booking the same visit by the patient from a plurality of types of applications that provide remote access to one or more portions of the one or more user interfaces generated to guide the patient through the booking flow based on conforming to one or more of a health care setting or a modality that aligns with both the patient's interests and one or more policies of the provider organization, and wherein the plurality of application types include one or more of a mobile application, a desktop application or an online application;
dynamically generating one or more selected user interfaces for the patient during the intermediate progress based on information collected during one or more of the plurality of portions for the current process to complete booking the visit;
determining one or more providers that are associated with the provider organization and are locally available to provide the requested healthcare services and virtually available to provide the requested healthcare services;
generating one or more matching models based on a localized requirement for the requested healthcare services, an objective of the provider organization, one or more metrics for outcome histories associated with the one or more providers, and heuristic data for the requested healthcare services;
generating one or more match scores for the one or more providers based on the one or more matching models and the visit profile, wherein each match score represents a quality of a match for assigning the one or more providers to the visit requested by the patient;
assigning a provider that is locally available for the visit and assigning an alternate provider that is virtually available for the visit based on the one or more match scores;
providing a virtual waiting room for the patient based on the visit profile, wherein one or more user interfaces in the virtual waiting room enable one or more interactions between the patient and the virtual waiting room, and wherein the virtual waiting room includes an estimated travel time, a cost, and a wait time to meet in person with the locally available provider and further includes an alternate cost, and an alternate wait time to communicate with the virtually available alternate provider;
updating the visit profile with supplemental information based on one or more of an interaction between the patient and the virtual waiting room, patient information from one or more data stores, or visit information from the one or more data stores;
providing one or more updated match scores for the one or more providers based on the one or more matching models and the updated visit profile; and
in response to an updated match score exceeding a previously determined higher match score, assigning one or more of another provider or another alternate provider to the visit based on the other provider or the other alternate provider being associated with the updated match score, wherein the visit is conducted by the other provider or the other alternate provider; and
one or more client computers, comprising:
a memory that stores at least instructions; and
one or more processors that execute instructions that are configured to cause the one or more client computers to perform actions, including:
providing one or more portions of the visit profile.

10. The system of claim 9, wherein the one or more interactions between the patient and the virtual waiting room, further comprise, one or more of:
exchanging text chat messages with the patient and the provider organization;
verifying that the patient has a technical capability to virtually conduct the visit;
collecting one or more audio samples or one or more video samples from the patient; or
employing one or more survey questions to collect one or more responses from the patient.

11. The system of claim 9, wherein providing the one or more match scores for the one or more providers, further comprises:
determining one or more of the one or more providers that are qualified based on the visit profile and the one or more matching models;
determining an availability of each qualified provider based on the visit profile and schedule information; and
providing the match score for each available qualified provider.

12. The system of claim 9, wherein the one or more network computer processors execute instructions that perform actions, further comprising:
in response to a conclusion of the visit, performing further actions, including:
providing one or more user interfaces to the patient;
employing the one or more user interfaces to collect additional patient information that includes satisfaction information provided by the patient; collecting additional visit information that include duration values for one or more portions of a visit from booking of the visit to conclusion of the visit; and
updating the one or more matching models based on the patient satisfaction information.

13. The system of claim 9, wherein the one or more network computer processors execute instructions that perform actions, further comprising:
in response to a conclusion of the visit, performing further actions, including:
providing one or more user interfaces to the provider;
employing the one or more user interfaces to collect visit resolution information from the provider;
updating the one or more matching models based on the visit resolution information; and
in response to the visit remaining unresolved, performing further actions, including:
reducing or waiving a fee associated with the visit;
recommending or scheduling one or more follow-on visits, including recommending or scheduling one or more follow-on visits with one or more specialized providers;
updating the updated visit profile based on the resolution information; or
scheduling another visit based on the updated visit profile.

14. The system of claim 9, wherein generating the one or more match scores for the one or more providers, further comprises:
determining one or more first partial match scores based on a utilization metric associated with each provider, wherein the utilization is based on one or more of a utilization history associated with each provider, a defined goal associated with each provider, one or more other metrics associated with each provider;
determining one or more second partial match scores based on outcome information associated with the one or more providers and an equivalent visit type as the visit, wherein the outcome information includes one or more of outcome history, effectiveness, or other information associated with the one or more providers;
determining one or more third partial match scores based on one or more metrics associated with the visit and one or more policies of the provider organization, wherein the one or more metrics associated with the visit, include one or more of definitive issue resolution, high patient satisfaction, high provider satisfaction, reduced visit duration, reduced cost, greater efficiency of delivering care in the visit, alignment with stated or predicted patient preferences, and wherein the stated or predicted patient preferences include one or more of location, language, ethnicity, gender or other patient preferences; and
providing the one or more match scores based on one or more of the one or more first partial match scores, the one or more second partial match scores, or the one or more third partial match score.

15. The system of claim 9, wherein the one or more network computer processors execute instructions that perform actions, further comprising:
adding the patient to one or more visit queues;
monitoring a duration that the patient is in the one or more visit queues;
generating and sharing wait times or other feedback with the patient; and
in response to the duration that the patient is in the one or more visit queues exceeding a threshold value, performing further actions, including:
generating one or more notifications to notify one or more representatives of the provider organization the queue duration is exceeding the threshold value;
updating the visit profile based on the queue duration exceeding the threshold value; and
assigning the visit to another provider based on the updated visit profile.

16. The system of claim 9, wherein the one or more network computer processors execute instructions that perform actions, further comprising:
determining the quality of the match based on a combination of an alignment of stated or predicted patient preferences, including one or more of location, language, ethnicity, gender, patient preference, or provider preference; and
determining a greatest likelihood of achieving a particular goal, including, one or more of definitive issue resolution, positive clinical outcome, high patient satisfaction, high provider satisfaction, reduced visit duration, reduced costs, greater efficiency of delivering care in the visit, or greater or more balanced provider utilization.

17. A network computer for managing provisioning of healthcare services, comprising:
a memory that stores at least instructions; and
one or more processors that execute instructions that are configured to cause the network computer to perform actions, including:
generating one or more user interfaces for a patient to provide a visit profile and request a visit to obtain healthcare services from a provider organization, wherein the visit profile includes geo-location information for the patient and one or more of a reason for the visit, symptom of an illness, sociographic information, or patient information, and wherein the provider organization employs the visit profile to select one or more of an interface control or local information that is included in the one or more user interfaces generated for the patient;
generating a booking flow representing intermediate progress of the patient for a current process that includes a plurality of portions in booking the visit, wherein the booking flow is used by one or more health care service engines to continuously and simultaneously provide for starting and stopping progress in the plurality of portions for booking the same visit by the patient from a plurality of types of applications that provide remote access to one or more portions of the one or more user interfaces generated to guide the patient through the booking flow based on conforming to one or more of a health care setting or a modality that aligns with both the patient's interests and one or more policies of the provider organization, and wherein the plurality of application types include one or more of a mobile application, a desktop application or an online application;
dynamically generating one or more selected user interfaces for the patient during the intermediate progress based on information collected during one or more of the plurality of portions for the current process to complete booking the visit;
determining one or more providers that are associated with the provider organization and are locally available to provide the requested healthcare services and virtually available to provide the requested healthcare services;
generating one or more matching models based on a localized requirement for the requested healthcare services, an objective of the provider organization, one or more metrics for outcome histories associated with the one or more providers, and heuristic data for the requested healthcare services;

generating one or more match scores for the one or more providers based on the one or more matching models and the visit profile, wherein each match score represents a quality of a match for assigning the one or more providers to the visit requested by the patient;

assigning a provider that is locally available for the visit and assigning an alternate provider that is virtually available for the visit based on the one or more match scores;

providing a virtual waiting room for the patient based on the visit profile, wherein one or more user interfaces in the virtual waiting room enable one or more interactions between the patient and the virtual waiting room, and wherein the virtual waiting room includes an estimated travel time, a cost, and a wait time to meet in person with the locally available provider and further includes an alternate cost, and an alternate wait time to communicate with the virtually available alternate provider;

updating the visit profile with supplemental information based on one or more of an interaction between the patient and the virtual waiting room, patient information from one or more data stores, or visit information from the one or more data stores;

providing one or more updated match scores for the one or more providers based on the one or more matching models and the updated visit profile; and in response to an updated match score exceeding a previously determined higher match score, assigning one or more of another provider or another alternate provider to the visit based on the other provider or the other alternate provider being associated with the updated match score, wherein the visit is conducted by the other provider or the other alternate provider.

18. The network computer of claim 17, wherein the one or more interactions between the patient and the virtual waiting room, further comprise, one or more of:

exchanging text chat messages with the patient and the provider organization;

verifying that the patient has a technical capability to virtually conduct the visit;

collecting one or more audio or one or more video samples from the patient; or employing one or more survey questions to collect one or more responses from the patient.

19. The network computer of claim 17, wherein providing the one or more match scores for the one or more providers, further comprises:

determining one or more of the one or more providers that are qualified based on the visit profile and the one or more matching models;

determining an availability of each qualified provider based on the visit profile and schedule information; and providing the match score for each available qualified provider.

20. The network computer of claim 17, wherein the one or more processors execute instructions that perform actions, further comprising:

in response to a conclusion of the visit, performing further actions, including:

providing one or more user interfaces to the patient;

employing the one or more user interfaces to collect additional patient information that includes satisfaction information provided by the patient;

collecting additional visit information that include duration values for one or more portions of a visit from booking of the visit to conclusion of the visit; and updating the one or more matching models based on the patient satisfaction information.

21. The network computer of claim 17, wherein the one or more processors execute instructions that perform actions, further comprising:

in response to a conclusion of the visit, performing further actions, including:

providing one or more user interfaces to the provider;

employing the one or more user interfaces to collect visit resolution information from the provider;

updating the one or more matching models based on the visit resolution information; and in response to the visit remaining unresolved, performing further actions, including:

reducing or waiving a fee associated with the visit;

recommending or scheduling one or more follow-on visits, including recommending or scheduling one or more follow-on visits with one or more specialized providers;

updating the updated visit profile based on the resolution information; or scheduling another visit based on the updated visit profile.

22. The network computer of claim 17, wherein generating the one or more match scores for the one or more providers, further comprises:

determining one or more first partial match scores based on a utilization metric associated with each provider, wherein the utilization is based on one or more of a utilization history associated with each provider, a defined goal associated with each provider, one or more other metrics associated with each provider;

determining one or more second partial match scores based on outcome information associated with the one or more providers and an equivalent visit type as the visit, wherein the outcome information includes one or more of outcome history, effectiveness, or other information associated with the one or more providers;

determining one or more third partial match scores based on one or more metrics associated with the visit and one or more policies of the provider organization, wherein the one or more metrics associated with the visit, include one or more of definitive issue resolution, high patient satisfaction, high provider satisfaction, reduced visit duration, reduced cost, greater efficiency of delivering care in the visit, alignment with stated or predicted patient preferences, and wherein the stated or predicted patient preferences include one or more of location, language, ethnicity, gender or other patient preferences; and providing the one or more match scores based on one or more of the one or more first partial match scores, the one or more second partial match scores, or the one or more third partial match score.

23. The network computer of claim 17, wherein the one or more processors execute instructions that perform actions, further comprising:

adding the patient to one or more visit queues;

monitoring a duration that the patient is in the one or more visit queues;

generating and sharing wait times or other feedback with the patient; and in response to the duration that the patient is in the one or more visit queues exceeding a threshold value, performing further actions, including:

generating one or more notifications to notify one or more representatives of the provider organization the queue duration is exceeding the threshold value;

updating the visit profile based on the queue duration exceeding the threshold value; and assigning the visit to another provider based on the updated visit profile.

24. A processor readable non-transitory storage media that includes instructions for managing provisioning of healthcare services over a network, wherein execution of the instructions are configured to cause one or more network computers perform the method comprising:

generating one or more user interfaces for a patient to provide a visit profile and request a visit to obtain healthcare services from a provider organization, wherein the visit profile includes geo-location information for the patient and one or more of a reason for the visit, symptom of an illness, sociographic information, or patient information, and wherein the provider organization employs the visit profile to select one or more of an interface control or local information that is included in the one or more user interfaces generated for the patient;

generating a booking flow representing intermediate progress of the patient for a current process that includes a plurality of portions in booking the visit, wherein the booking flow is used by one or more health care service engines to continuously and simultaneously provide for starting and stopping progress in the plurality of portions for booking the same visit by the patient from a plurality of types of applications that provide remote access to one or more portions of the one or more user interfaces generated to guide the patient through the booking flow based on conforming to one or more of a health care setting or a modality that aligns with both the patient's interests and one or more policies of the provider organization, and wherein the plurality of application types include one or more of a mobile application, a desktop application or an online application;

dynamically generating one or more selected user interfaces for the patient during the intermediate progress based on information collected during one or more of the plurality of portions for the current process to complete booking the visit;

determining one or more providers that are associated with the provider organization and are locally available to provide the requested healthcare services and virtually available to provide the requested healthcare services;

generating one or more matching models based on a localized requirement for the requested healthcare services, an objective of the provider organization, one or more metrics for outcome histories associated with the one or more providers, and heuristic data for the requested healthcare services;

generating one or more match scores for the one or more providers based on the one or more matching models and the visit profile, wherein each match score represents a quality of a match for assigning the one or more providers to the visit requested by the patient;

assigning a provider that is locally available for the visit and assigning an alternate provider that is virtually available for the visit based on the one or more match scores;

providing a virtual waiting room for the patient based on the visit profile, wherein one or more user interfaces in the virtual waiting room enable one or more interactions between the patient and the virtual waiting room, and wherein the virtual waiting room includes an estimated travel time, a cost, and a wait time to meet in person with the locally available provider and further includes an alternate cost, and an alternate wait time to communicate with the virtually available alternate provider;

updating the visit profile with supplemental information based on one or more of an interaction between the patient and the virtual waiting room, patient information from one or more data stores, or visit information from the one or more data stores;

providing one or more updated match scores for the one or more providers based on the one or more matching models and the updated visit profile; and in response to an updated match score exceeding a previously determined higher match score, assigning one or more of another provider or another alternate provider to the visit based on the other provider or the other alternate provider being associated with the updated match score, wherein the visit is conducted by the other provider or the other alternate provider.

25. The media of claim 24, wherein the one or more interactions between the patient and the virtual waiting room, further comprise, one or more of:

exchanging text chat messages with the patient and the provider organization;

verifying that the patient has a technical capability to virtually conduct the visit;

collecting one or more audio samples or one or more video samples from the patient; or employing one or more survey questions to collect one or more responses from the patient.

26. The media of claim 24, wherein providing the one or more match scores for the one or more providers, further comprises:

determining one or more of the one or more providers that are qualified based on the visit profile and the one or more matching models;

determining an availability of each qualified provider based on the visit profile and schedule information; and providing the match score for each available qualified provider.

27. The media of claim 24, further comprising:

in response to a conclusion of the visit, performing further actions, including:

providing one or more user interfaces to the patient;

employing the one or more user interfaces to collect additional patient information that includes satisfaction information provided by the patient;

collecting additional visit information that include duration values for one or more portions of a visit from booking of the visit to conclusion of the visit; and updating the one or more matching models based on the patient satisfaction information.

28. The media of claim 24, further comprising:

in response to a conclusion of the visit, performing further actions, including:

providing one or more user interfaces to the provider;

employing the one or more user interfaces to collect visit resolution information from the provider;

updating the one or more matching models based on the visit resolution information; and in response to the visit remaining unresolved, performing further actions, including:
- reducing or waiving a fee associated with the visit;
- recommending or scheduling one or more follow-on visits, including recommending or scheduling one or more follow-on visits with one or more specialized providers;
- updating the updated visit profile based on the resolution information; or
- scheduling another visit based on the updated visit profile.

29. The media of claim 24, wherein generating the one or more match scores for the one or more providers, further comprises:
- determining one or more first partial match scores based on a utilization metric associated with each provider, wherein the utilization is based on one or more of a utilization history associated with each provider, a defined goal associated with each provider, one or more other metrics associated with each provider;
- determining one or more second partial match scores based on outcome information associated with the one or more providers and an equivalent visit type as the visit, wherein the outcome information includes one or more of outcome history, effectiveness, or other information associated with the one or more providers;
- determining one or more third partial match scores based on one or more metrics associated with the visit and one or more policies of the provider organization, wherein the one or more metrics associated with the visit, include one or more of definitive issue resolution, high patient satisfaction, high provider satisfaction, reduced visit duration, reduced cost, greater efficiency of delivering care in the visit, alignment with stated or predicted patient preferences, and wherein the stated or predicted patient preferences include one or more of location, language, ethnicity, gender or other patient preferences; and
- providing the one or more match scores based on one or more of the one or more first partial match scores, the one or more second partial match scores, or the one or more third partial match score.

30. The media of claim 24, further comprising:
- adding the patient to one or more visit queues;
- monitoring a duration that the patient is in the one or more visit queues;
- generating and sharing wait times or other feedback with the patient; and
- in response to the duration that the patient is in the one or more visit queues exceeding a threshold value, performing further actions, including:
  - generating one or more notifications to notify one or more representatives of the provider organization the queue duration is exceeding the threshold value;
  - updating the visit profile based on the queue duration exceeding the threshold value; and
  - assigning the visit to another provider based on the updated visit profile.

* * * * *